(12) United States Patent
Omura et al.

(10) Patent No.: US 7,250,402 B2
(45) Date of Patent: Jul. 31, 2007

(54) AVERMECTIN DERIVATIVES

(75) Inventors: Satoshi Omura, Tokyo (JP); Kenichiro Nagai, Tokyo (JP); Toshiaki Sunazuka, Funabashi (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/997,869

(22) Filed: Nov. 29, 2004

(65) Prior Publication Data

US 2005/0148520 A1    Jul. 7, 2005

Related U.S. Application Data

(63) Continuation of application No. 10/343,972, filed as application No. PCT/JP01/06803 on Aug. 8, 2001, now abandoned.

(30) Foreign Application Priority Data

Aug. 9, 2000    (JP) .............................. 2000-240988

(51) Int. Cl.
*A61K 31/70* (2006.01)
*C07H 17/08* (2006.01)
(52) U.S. Cl. ......................... 514/30; 536/7.1
(58) Field of Classification Search ................. 536/7.1; 514/30
See application file for complete search history.

(56) References Cited

U.S. PATENT DOCUMENTS 4,200,581 A    4/1980  Fisher et al.

(Continued)

FOREIGN PATENT DOCUMENTS

EP    0008184    2/1980

(Continued)

OTHER PUBLICATIONS

English Language Abstract of JP 3-254678 (provided by esp@cenet).

(Continued)

*Primary Examiner*—Elli Peselev
(74) *Attorney, Agent, or Firm*—Connolly Bove Lodge & Hutz LLP

(57) ABSTRACT

A compound represented by the general formula (I) or a salt thereof:

(I)

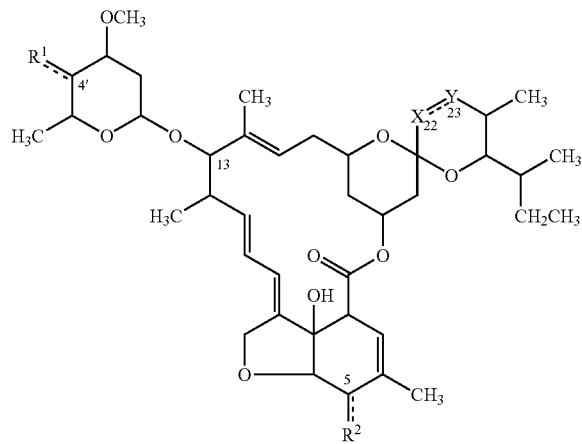

wherein

—X═Y— represents —CH═CH—, —CH$_2$—CH$_2$— or the like, between $R^1$ and the carbon atom at 4'-position represents a single bond or a double bond, between $R^2$ and the carbon atom at 5-position represents a single bond or a double bond, and for example, 1) when

—X═Y— represents —CH═CH— or —CH$_2$—CH$_2$—, and between $R^1$ and the carbon atom at 4'-position represents a double bond, $R^1$ represents ═C($R^{11}$)($R^{12}$) (wherein $R^{11}$ represents a lower alkyl group or the like and $R^{12}$ represents a hydrogen atom or the like) or the like, and $R^2$ represents a hydroxyl group or the like, or $R^2$ may be combined together with the carbon atom at 5-position to form a carbonyl group, and 2) when

—X═Y— represents —CH═CH— or —CH$_2$—CH$_2$—, and between $R^1$ and the carbon atom at 4'-position represents a single bond, $R^1$ represents —OCH($R^{1a}$)($R^{1b}$) (wherein $R^{1a}$ represents a lower alkyl or the like and $R^{1b}$ represents a hydrogen atom or the like) or the like, and $R^2$ represents a hydroxyl group or the like.

11 Claims, No Drawings

U.S. PATENT DOCUMENTS

| | | | |
|---|---|---|---|
| 4,427,663 | A | 1/1984 | Mrozik |
| 4,833,168 | A | 5/1989 | Wyvratt |
| 4,895,837 | A | 1/1990 | Mrozik et al. |
| 4,906,619 | A | 3/1990 | Eskola et al. |
| 5,030,622 | A | 7/1991 | Mrozik et al. |
| 5,169,839 | A | 12/1992 | Linn et al. |
| 5,206,155 | A | 4/1993 | Omura et al. |
| 5,208,222 | A | 5/1993 | Meinke et al. |
| 5,229,415 | A | 7/1993 | Linn et al. |
| 5,369,021 | A | 11/1994 | Satoshi et al. |
| 5,723,488 | A | 3/1998 | Walshe |
| 5,733,887 | A | 3/1998 | Walshe |
| 5,883,080 | A | 3/1999 | Dutton et al. |
| 6,605,595 | B1 * | 8/2003 | Omura et al. ............... 514/30 |

FOREIGN PATENT DOCUMENTS

| | | |
|---|---|---|
| EP | 0351923 | 1/1990 |
| EP | 0456509 | 11/1991 |
| EP | 0480693 | 4/1992 |
| EP | 0506331 | 9/1992 |
| JP | 3-74397 | 3/1991 |
| JP | 3-254678 | 11/1991 |
| JP | 6-33273 | 5/1994 |
| WO | WO-93/18778 | 9/1993 |
| WO | WO-94/29328 | 12/1994 |
| WO | WO-95/04746 | 2/1995 |
| WO | WO-95/22552 | 8/1995 |

OTHER PUBLICATIONS

English Language Abstract of JP 3-74397 (provided by esp@cenet).
English Language Abstract corresponding to JP 6-33273 (provided by esp@cenet).
Chabala, J.C. et al., "Ivermectin, a New Broad-Spectrum Antiparasitic Agent," J. Med. Chem., 1980, 23, pp. 1134-1136.
Mrozik, H. et al., "Avermectin Acyl Derivatives with Anthelmintic Activity," J. Med. Chem. 1982, 25, pp. 658-663.
U.S. Appl. No. 10/343,980, filed Feb. 6, 2003 (National Stage of PCT/JP01/06802, filed Aug. 8, 2001) having the title "Avermectin Derivatives" (Applicants: Satoshi Omura et al.).
Shin, et al., "Cleavage of the Spiroketal Portion of Avermectin $B_{2p}$," Tetrahedron Letters, 1990, pp. 3525-3528, vol. 31, No. 25, Pergamon Press.

\* cited by examiner

AVERMECTIN DERIVATIVES

This application is a continuation of U.S. application Ser. No. 10/343,972, filed Sep. 8, 2003, now abandoned which is hereby incorporated by reference in its entirety, which is a National Stage application of PCT/JP01/06803, filed Aug. 8, 2001.

TECHNICAL FIELD

The present invention relates to avermectin derivatives having antiparasitic activity.

BACKGROUND ART

Avermectins are antiparasitic antibiotics produced by *Streptomyces avermitilis*. Four main ingredients (A1a, A2a, B1a and B2a) have been known, and among them, avermectin B1a is known to have potent activity (Japanese Patent Unexamined Publication (KOKAI) No. (Hei) 3-254678/1991).

Various derivatives have been synthesized so far to provide avermectin derivatives having higher activity. However, these derivatives fail to have fully satisfactory antiparasitic activity. For example, a monosaccharide derivative as avermectin derivatives are known. However, these derivatives are known to have two to four fold weaker activity than corresponding disaccharide compounds (J. Med. Chem., 23, 1134-1136, 1980).

DISCLOSURE OF THE INVENTION

An object of the present invention is to provide avermectin derivatives having antiparasitic activity.

In order to find avermectin derivatives having higher antiparasitic activity, the inventors of the present invention synthesized various derivatives using avermectins B1a, B2a and ivermectin as starting materials. As a result, we succeeded in obtaining derivatives represented by the following general formula (I) which have high antiparasitic activity. The present invention was achieved on the basis of the findings.

The present invention thus provides compounds represented by the general formula (I) or salts thereof:

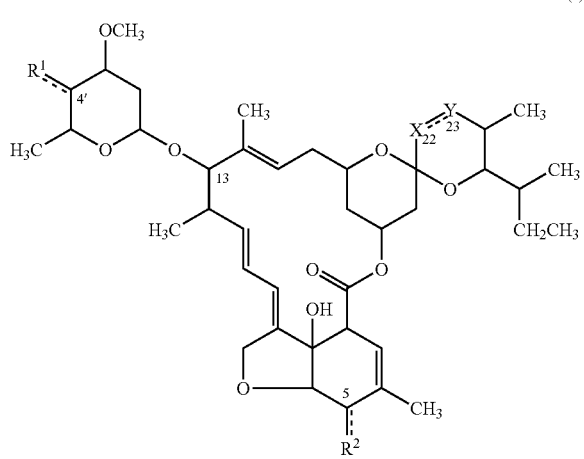

(I)

wherein

—X═Y— represents —CH═CH—, —CH$_2$—C(═O)—, —CH$_2$—CH$_2$—, or —CH$_2$—CH(R$^{13}$)— (wherein R$^{13}$ represents a hydroxyl group or a lower alkylcarbonyloxy group),

----- between R$^1$ and the carbon atom at 4'-position represents a single bond or a double bond,

----- between R$^2$ and the carbon atom at 5-position represents a single bond or a double bond, and
1) when

—X═Y— represents —CH═CH— or —CH$_2$—CH$_2$—, and

----- between R$^1$ and the carbon atom at 4'-position represents a double bond,
R$^1$ represents ═C(R$^{11}$)(R$^{12}$)<wherein R$^{11}$ represents a substituted or unsubstituted lower alkyl group, a formyl group, a lower alkoxycarbonyl group (wherein a lower alkyl moiety of said lower alkoxycarbonyl group may be substituted with a heterocyclic group), —CH═N—OR$^3$ (wherein R$^3$ represents a hydrogen atom or a lower alkyl group), a lower alkenylcarbonyl group, —CH═N—NH—CONH$_2$, a cyano group, —COR$^4$ {wherein R$^4$ represents a hydroxyl group, a lower alkenyloxy group, or —N(R$^5$)(R$^6$) (wherein R$^5$ and R$^6$ are combined together with the adjacent nitrogen atom to form a nitrogen-containing heterocyclic group)}, a vinyl group substituted with a lower alkenyloxycarbonyl group, —CO—S—CH$^2$—CH$_2$—NH—CO—R$^X$ (wherein R$^X$ represents a lower alkyl group), or —CH═CH—COOH, and R$^{12}$ represents a hydrogen atom, provided that when R$^{11}$ represents a cyano group, R$^{12}$ represents a hydrogen atom or a lower alkyl group>, or is combined together with the carbon atom at 4'-position to form a carbonyl group, and when

----- between R$^2$ and the carbon atom at 5-position represents a single bond, R$^2$ represents a hydroxyl group, a lower alkoxyl group, or a lower alkenyloxycarbonyloxy group, and when

----- between $R^2$ and the carbon atom at 5-position represents a double bond, $R^2$ is combined together with the carbon atom at 5-position to form a carbonyl group or a hydroxime group (—C(=NOH)—);
2) when

—X═Y— represents —CH=CH— or —CH$_2$—CH$_2$—, and

----- between $R^1$ and the carbon atom at 4'-position represents a single bond,
$R^1$ represents a hydroxyl group, —OCH($R^{1a}$)($R^{1b}$)<wherein $R^{1a}$ represents a substituted or unsubstituted lower alkyl group, a formyl group, a carboxyl group, a lower alkoxycarbonyl group (wherein a lower alkyl moiety of said lower alkoxycarbonyl group may be substituted with a heterocyclic group), —CH=N—OR$^7$ (wherein $R^7$ represents a hydrogen atom or a lower alkyl group), a lower alkenyloxycarbonyl group, —CH=N—NH—CONH$_2$, a cyano group, —COR$^8$ {wherein $R^8$ represents an arylalkyloxy group (wherein the aryl group may contain one or more heteroatoms as ring-constituting atoms) or —N($R^9$)($R^{10}$) (wherein $R^9$ and $R^{10}$ are combined together with the adjacent nitrogen atom to form a nitrogen-containing heterocyclic group)}, a vinyl group substituted with a lower alkenyloxycarbonyl group, —CO—S—CH$^2$—CH$_2$—NH—CO—R$^Y$ (wherein $R^Y$ represents a lower alkyl group), —CH=CH—COOH, or a substituted or unsubstituted aryl group, and $R^{1b}$ represents a hydrogen atom, provided that when $R^{1a}$ represents a carboxyl group or a lower alkoxycarbonyl group (wherein a lower alkyl moiety of said lower alkoxycarbonyl group may be substituted with a heterocyclic group), $R^{1b}$ may further represents a lower alkoxycarbonyl group (wherein a lower alkyl moiety of said lower alkoxycarbonyl group may be substituted with a heterocyclic group), a carboxyl group, a cyano group, or an aryl group>, a carboxymethyl group, or a cyanomethyl group, and
when

----- between $R^2$ and the carbon atom at 5-position represents a single bond, $R^2$ represents a hydroxyl group, a lower alkoxyl group, or a lower alkenyloxycarbonyloxy group, and when

----- between $R^2$ and the carbon atom at 5-position represents a double bond, $R^2$ is combined together with the carbon atom at 5-position to form a carbonyl group or a hydroxime group (—C(=NOH)—);
3) when

—X═Y— represents —CH$_2$—C(=O)—, and

----- between $R^1$ and the carbon atom at 4'-position represents a double bond,
$R^1$ represents =C($R^{11a}$)($R^{12a}$) (wherein $R^{11a}$ represents a lower alkoxycarbonyl group (wherein a lower alkyl moiety of said lower alkoxycarbonyl group may be substituted with a heterocyclic group) or —COOCH$_2$CH=CH$_2$, and $R^{12a}$ represents a hydrogen atom), or is combined together with the carbon atom at 4'-position to form carbonyl group,

----- between $R^2$ and the carbon atom at 5-position represents a single bond, and $R^2$ represents a hydroxyl group, a lower alkoxyl group, or a lower alkenyloxycarbonyloxy group;
4) when

—X═Y— represents —CH$_2$—C(=O)—, and

----- between $R^1$ and the carbon atom at 4'-position represents a single bond,
$R^1$ represents —OCH($R^{1aa}$)($R^{1ba}$)<wherein $R^{1aa}$ represents a substituted or unsubstituted lower alkyl group, a formyl group, a carboxyl group, a lower alkoxycarbonyl group (wherein a lower alkyl moiety of said lower alkoxycarbonyl group may be substituted with a heterocyclic group), —CH=N—OR$^{7a}$ (wherein $R^{7a}$ represents a hydrogen atom or a lower alkyl group), a lower alkenyloxycarbonyl group, —CH=N—NH—CONH$_2$, a cyano group, —COR$^{8a}$ {wherein $R^{8a}$ represents an arylalkyloxy group (wherein the aryl group may contain one or more heteroatoms as ring-constituting atoms), or —N($R^{9a}$)

($R^{10a}$) (wherein $R^{9a}$ and $R^{10a}$ are combined together with the adjacent nitrogen atom to form a nitrogen-containing heterocyclic group)}, a vinyl group substituted with a lower alkenyloxycarbonyl group, —CO—S—CH$^2$—CH$_2$—NH—CO—$R^{Ya}$ (wherein $R^{Ya}$ represents a lower alkyl group), —CH═CH—COOH, or a substituted or unsubstituted aryl group, and $R^{1ba}$ represents a hydrogen atom, provided that when $R^{1aa}$ represents a carboxyl group or a lower alkoxycarbonyl group (wherein a lower alkyl moiety of said lower alkoxycarbonyl group may be substituted with a heterocyclic group), $R^{1ba}$ may further represents a lower alkoxycarbonyl group (wherein a lower alkyl moiety of said lower alkoxycarbonyl group may be substituted with a heterocyclic group), a carboxyl group, a cyano group, or an aryl group>, and when

----- between $R^2$ and the carbon atom at 5-position represents a single bond, $R^2$ represents a hydroxyl group, a lower alkoxyl group, or a lower alkenyloxycarbonyloxy group, and when

----- between $R^2$ and the carbon atom at 5-position represents a double bond, $R^2$ is combined together with the carbon atom at 5-position to form a carbonyl group or a hydroxime group (—C(═NOH)—);

5) when

—X═Y— represents —CH$_2$—CH($R^{13}$)— (wherein $R^{13}$ has the same meaning as that defined above), and

-----

50 between $R^1$ and the carbon atom at 4'-position represents a double bond, $R^1$ represents ═C($R^{11b}$)($R^{12b}$) (wherein $R^{11b}$ represents a cyano group, a carboxyl group, a lower alkoxycarbonyl group, or a lower alkenyloxycarbonyl group, or is combined together with the carbon atom at 4'-position to form a carbonyl group, and $R^{12b}$ represents a hydrogen atom),

----- between $R^3$ and the carbon atom at 5-position represents a single bond, and $R^2$ represents a hydroxyl group, a lower alkoxyl group, or a lower alkenyloxycarbonyloxy group; and 6) when

—X═Y— represents —CH$_2$—CH($R^{13}$)— (wherein $R^{13}$ has the same meaning as that defined above), and

----- between $R^1$ and the carbon atom at 4'-position represents a single bond, $R^1$ represents —OCH($R^{1ab}$)($R^{1bb}$)<wherein $R^{1ab}$ represents a substituted or unsubstituted lower alkyl group, a formyl group, a carboxyl group, a lower alkoxycarbonyl group (wherein a lower alkyl moiety of said lower alkoxycarbonyl group may be substituted with a heterocyclic group), —CH═N—O$R^{7b}$ (wherein $R^{7b}$ represents a hydrogen atom or a lower alkyl group), a lower alkenyloxycarbonyl group, —CH═N—NH—CONH$_2$, a cyano group, —CO$R^{8b}$ {wherein $R^{8b}$ represents an arylalkyloxy group (wherein the aryl group may contain one or more heteroatoms as ring-constituting atoms), or —N($R^{9b}$)($R^{10b}$) (wherein $R^{9b}$ and $R^{10b}$ are combined together with the adjacent nitrogen atom to form a nitrogen-containing heterocyclic group)}, a vinyl group substituted with a lower alkenyloxycarbonyl group, —CO—S—CH$^2$—CH$_2$—NH—CO—$R^{Yb}$ (wherein $R^{Yb}$ represents a lower alkyl group), —CH═CH—COOH, or a substituted or unsubstituted aryl group, and $R^{1bb}$ represents a hydrogen atom, provided that when $R^{1ab}$ represents a carboxyl group or a lower alkoxycarbonyl group (wherein a lower alkyl moiety of said lower alkoxycarbonyl group may be substituted with a heterocyclic group), $R^{1bb}$ may further represents a lower alkoxycarbonyl group (wherein a lower alkyl moiety of said lower alkoxycarbonyl group may be substituted with a heterocyclic group), a carboxyl group, a cyano group, or an aryl group>, and when

----- between $R^2$ and the carbon atom at 5-position represents a single bond, $R^2$ represents a hydroxyl group, a lower alkoxyl group, or a lower alkenyloxycarbonyloxy group, and when

----- between $R^2$ and the carbon atom at 5-position represents a double bond, $R^2$ is combined together with the carbon atom at 5-position to form a carbonyl group or a hydroxime group (—C(═NOH)—).

According to the general formula (I) of the present invention, the compound or a salt thereof wherein $$-X\doteq Y-$$

is —CH=CH— is preferred. Among them, the compound wherein $R^{11}$ is a substituted or unsubstituted lower alkyl group, a formyl group, a lower alkoxycarbonyl group, a lower alkenylcarbonyl group, cyano group, or —COR$^4$ (wherein R$^4$ has the same meaning as that defined above), the compound {wherein R$^1$ is hydroxyl group or —OCH$^2$R$^{1ac}$ wherein R$^{1ac}$ represents a substituted or unsubstituted lower alkyl group, carboxyl group, or a lower alkoxycarbonyl group (the lower alkyl moiety of the lower alkoxycarbonyl group may be substituted with a heterocyclic group)} or the salts thereof are preferred.

According to the general formula (I) of the present invention, the compound or a salt thereof wherein $$-X\doteq Y-$$

is —CH$_2$—CH$_2$— is also preferred. Among them, the compound wherein R$^{11}$ is a substituted or unsubstituted lower alkyl group, a formyl group, a lower alkoxycarbonyl group, a lower alkenylcarbonyl group, cyano group, or —COR$^4$ (wherein R$^4$ has the same meaning as that defined above), the compound wherein R$^1$ is hydroxyl group or —OCH$^2$R$^{1ac}$ {wherein R$^{1ac}$ represents a substituted or unsubstituted lower alkyl group, carboxyl group, or a lower alkoxycarbonyl group (the lower alkyl moiety of the lower alkoxycarbonyl group may be substituted with a heterocyclic group)} or the salts thereof are preferred.

Also according to the general formula (I) of the present invention, the compound or a salt thereof wherein R$^2$ is hydroxyl group or a lower alkenyloxycarbonyloxy group is preferred.

According to another aspect of the present invention, there are provided medicaments which comprise as an active ingredient the compound represented by the aforementioned general formula (I) or the physiologically acceptable salt thereof. The medicaments can be administered as agents for therapeutic treatment of parasitosis to a mammal including a human.

According to further aspects of the present invention, there are provided a use of the compound represented by the aforementioned general formula (I) or the physiologically acceptable salt thereof for the manufacture of the aforementioned medicament; and a method for therapeutic treatment of parasitosis which comprises the step of administering a therapeutically effective amount of the compound represented by the aforementioned general formula (I) or the physiologically acceptable salt thereof to a mammal including a human.

BEST MODE FOR CARRYING OUT THE INVENTION

Hereinafter the compounds represented by the general formula (I) are referred to as the compounds (I). The compounds of other formula numbers are abbreviated in a similar manner.

In the compounds (I) of the present invention, $$-X\doteq Y-$$

represents —CH=CH—, —CH$_2$—C(=O)—, —CH$_2$—CH$_2$—, or —CH$_2$—CH(R$^{13}$)— (wherein R$^{13}$ has the same meaning as that defined above, and in each formula, the carbon atom on the left side corresponds to X.).

In the compounds (I) of the present invention, the compounds wherein $$-X\doteq Y-$$

is —CH=CH— and $$-----$$

between R$^1$ and a carbon atom at the 4'-position is a double bond are referred to as the compounds (Ia), and the compounds wherein $$-X\doteq Y-$$

is —CH=CH— and $$-----$$

between R$^1$ and a carbon atom at the 4'-position is a single bond are referred to as the compounds (Ic).

In the compounds (I) of the present invention, the compounds wherein $$-X\doteq Y-$$

is —CH$_2$—CH$_2$—, and $$-----$$

between R$^1$ and a carbon atom at the 4'-position is a double bond is referred to as the compounds (Ib), the compounds wherein $$-X\doteq Y-$$

is —CH$_2$—CH$_2$—, and between $R^1$ and a carbon atom at the 4'-position is a single bond is referred to as the compounds (Id).

In the compounds (I) of the present invention, the compounds wherein

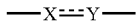

is —$CH_2$—C(=O)— are referred to as the compounds (Ie), and the compounds wherein

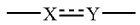

is —$CH_2$—CH($R^{13}$)— (wherein $R^{13}$ has the same meaning as that defined above) are referred to as the compounds (If).

In the definition of each group in the compounds (I), the lower alkyl group may be any of $C_1$-$C_8$ linear, branched, and cyclic alkyl groups or a combination thereof, preferably a $C_1$-$C_8$ linear or branched alkyl group. The lower alkyl group includes, for example, a methyl group, ethyl group, propyl group, isopropyl group, cyclopropyl group, butyl group, isobutyl group, sec-butyl group, tert-butyl group, cyclopropylmethyl group, cyclobutyl group, pentyl group, hexyl group, heptyl group, octyl group, and the like. A lower alkyl moiety in functional groups having the lower alkyl moiety, such as the lower alkoxycarbonyl group, lower alkoxyl group, and lower alkylcarbonyloxy group, has the same meaning as that defined in the aforementioned lower alkyl group, unless otherwise specifically mentioned.

The alkyl moiety of the arylalkyloxy group is a group wherein one of hydrogen atom is removed from an a lower alkyl group.

Examples of a lower alkenyl moiety in the lower alkenylcarbonyl group, the lower alkenyloxycarbonyl group, the lower alkenyloxy group, and the lower alkenyloxycarbonyloxy group include $C_2$-$C_6$ straight and branched alkenyl groups, for example, a vinyl group, allyl group, methacryl group, butenyl group, pentenyl group, hexenyl group and the like. Allyl group is particularly preferred. The number of double bonds present in the alkenyl group is not particularly limited, and preferably one.

Example of the aryl group and the aryl moiety of the arylalkyloxy group include phenyl group, and naphthyl group.

The heterocyclic group may be either an aromatic or aliphatic heterocyclic group. Examples of the aromatic heterocyclic group include, for example, a 5- or 6-membered monocyclic aromatic heterocyclic group which contains at least one heteroatom selected from the group consisting of nitrogen, oxygen, and sulfur atoms. More specifically, examples include a pyridyl group, pyrrolyl group, furyl group, thienyl group, thiazolyl group, pyrazinyl group, imidazolyl group, pyrazolyl group, triazolyl group, tetrazolyl group, and oxazolyl group. Examples of the aliphatic heterocyclic group include, for example, a 5- or 6-membered monocyclic aliphatic heterocyclic group which contains at least one heteroatom selected from the group consisting of nitrogen, oxygen, and sulfur atoms. More specifically, examples include a pyrrolidinyl group, tetrahydrofuryl group, and tetrahydropyranyl group.

The nitrogen containing heterocyclic group formed together with the adjacent nitrogen atom includes a morpholino group, thiomorpholino group, piperidino group, 1-piperazinyl group, and 1-pyrrolidinyl group.

The type and number of the substituent of the substituted lower alkyl group are not particularly limited. Preferably, the number of the substituent is from 1 to 3, and examples include a hydroxyl group, a halogen atom ("a halogen atom" used herein may be any of fluorine, chlorine, bromine, and iodine atoms), an amino group, a hydroxyamino group, a mono(lower alkyl)amino group, a mono(lower alkoxy)amino group, a lower alkanoylamino group, an azide group, a heterocyclic group (examples of the heterocyclic group include the groups exemplified for the aforementioned heterocyclic group and the nitrogen containing heterocyclic group formed together with the adjacent nitrogen atom), a lower alkanoyloxy group, a heterocyclic carbonyloxy group (i.e., heterocycle -C(=O)—O— wherein the heterocyclic moiety has the same meaning as that defined in the aforementioned heterocyclic group and the heterocyclic moiety may be substituted with a halogen atom or a lower alkoxycarbonyl group), a heterocyclic-oxy group such as tetrahydropyranyloxy group, an aryl group, a substituted or unsubstituted arylcarbonyloxy group (the type and number of the substituent on the aryl group of the substituted arylcarbonyloxy group is not particularly limited, and examples preferably include one to five substituents such as a halogen atom, an amino group, a hydroxyl group, and a nitro group), a substituted or unsubstituted arylsulfonyloxy group (the substituent of the substituted arylsulfonyloxy group may be the alkyl group having the same meaning as that defined above), a lower alkylsulfonyloxy group, a carboxyl group, a lower alkoxycarbonyl group, and a cyano group.

In the definition of the substituent of the substituted lower alkyl group, a lower alkyl moiety of the mono(lower alkyl) amino group, mono(lower alkoxy)amino group, lower alkanoylamino group, lower alkanoyloxy group, lower alkoxycarbonyl group, and lower alkylsulfonyloxy group has the same meaning as that defined in the aforementioned lower alkyl group.

In the definition of the substituents of the substituted lower alkyl group, the aryl group and an aryl moiety of the arylcarbonyloxy group and arylsulfonyloxy group has the same meaning as that defined in the aforementioned aryl group.

The type and number of the substituent of the substituted aryl group are not particularly limited. Preferably, examples include one to five substituents such as a nitro group, an amino group, a hydroxyl group, and a halogen atom.

Examples of the salt of the compounds (I) include acid-addition salts, metal salts, ammonium salts, and organic amine-addition salts. Examples of the acid-addition salts include inorganic acid salts such as hydrochlorides, sulfates, nitrates and phosphates, and organic acid salts such as acetates, maleates, fumarates and citrates. Examples of the metal salts include alkali metal salts such as sodium salts and potassium salts, alkaline-earth metal salts such as magnesium salts and calcium salts, aluminium salts, and zinc salts. Examples of the ammonium salts include ammonium salts and tetramethylammonium salts, and examples of the organic amine-addition salts include salts with morpholine and piperidine. When a salt of the compound (I) is used as an active ingredient of the medicament of the present invention, a physiologically acceptable salt is preferably used.

Preparations of the compounds (I) will be explained below.

Avermectin B1a monosaccharide, avermectin B2a monosaccharide, and ivermectin monosaccharide (22,23-dihydroavermectin B1a monosaccharide), which are used as intermediates for the compound (I) disclosed by the present invention, were prepared respectively from avermectin B1a and avermectin B2a according to the method described in the publication (J. Med. Chem., 23, 1134-1136, 1980).

Avermectins B1a and B2a, which are used as starting materials, are isolated from the culture of *Streptomyces avermitilis*, and they are known compounds (Japanese Patent Unexamined Publication (KOKAI) Nos. (Hei) 3-74397/1991 and 3-254678/1991, and U.S. Pat. No. 5,206,165 and the like).

Among the compound (I) of the present invention, the compound wherein

—X═Y— is —CH═CH— (the compound (Ia) and the compound (Ic)) can be prepared from the aforementioned intermediate avermectin B1a monosaccyaride, and the compound wherein

—X═Y— is —CH$_2$—CH$_2$— (the compound (Ib) and the compound (Id)) can be prepared from the aforementioned intermediate ivermectin monosaccyaride.

Among the compound (I) of the present invention, the compound (Ie) wherein

—X═Y— is —CH$_2$—C(═O) can be prepared from the compound obtained by oxidation of the hydroxyl group at the 23-position of the aforementioned intermediate avermectin B2a monosaccyaride, and the compound (If) wherein

—X═Y— is —CH$_2$—CH(R$^{13}$)— (wherein R$^{13}$ has the same meaning as that defined above) can be prepared from the aforementioned intermediate avermectin B2a monosaccyaride.

In the following preparations, when a defined group is changed under conditions for a method to be applied, or the group is unsuitable for carrying out the method, desired compound can be obtained by employing introduction and elimination of a protective group conventionally used in synthetic organic chemistry [see, for example, Protective Groups in Organic Synthesis, T. W. Greene, John Wiley & Sons Inc. (1981)].

Preparation 1

Among the compound (I), the compound wherein

—X═Y— is —CH═CH—, —CH$_2$—CH$_2$—, or —CH$_2$—C(═O)—, R$^1$ is a lower alkoxycarbonylmethylidene group optionally substituted with a heterocyclic group, a lower alkenyloxycarbonylmethylidene group, or ═CH—COOCH$_2$CH═CH$_2$, or a cyanomethylidene group, and R$^2$ is a lower alkenyloxycarbonyloxy group (the compound (Ia2), the compound (Ib2), and the compound (Ie2)) can be prepared by the process set out below:

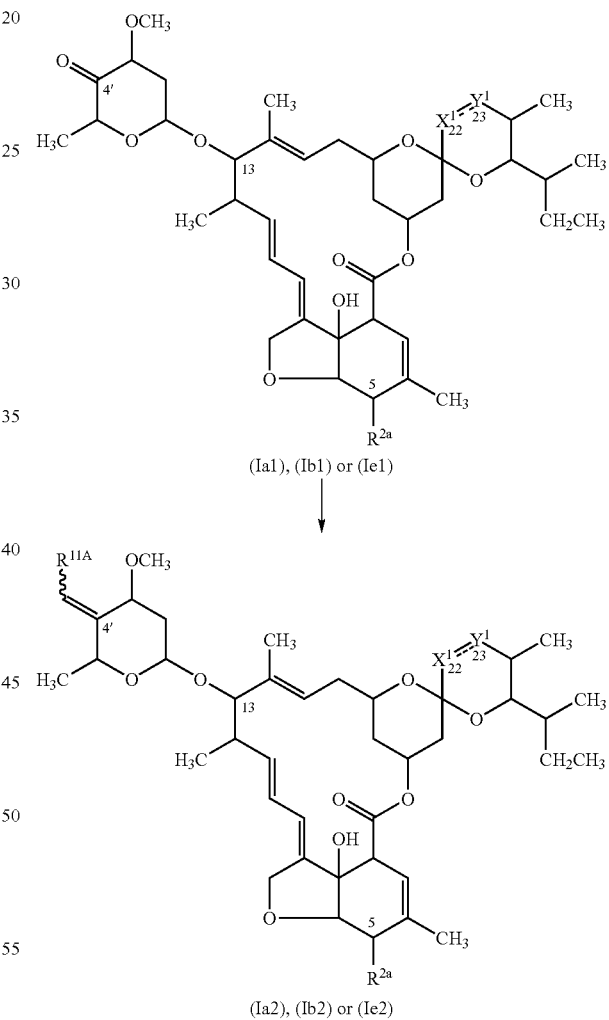

(In the scheme, R$^{11A}$ represents a lower alkoxycarbonyl group optionally substituted with a heterocyclic group, a lower alkenyloxycarbonyl group or —COOCH$_2$CH═CH$_2$, or a cyano group among the definition of R$^{11}$ or R$^{11a}$; R$^{2a}$ represents a lower alkenyloxycarbonyloxy group among the definition of R$^2$; and

—X¹⁼⁼⁼Y¹— represents —CH=CH—, —CH₂—CH₂—, or —CH₂—C(=O)—.)

The compound (Ia2), (Ib2), or (Ie2) can be obtained by reacting the compound (Ia1), (Ib1), or (Ie1) with 1 to 10 equivalents of the compound (II) represented by the formula: (RO)₂P(O)CH₂R$^{11A}$ wherein R represents a lower alkyl group having the same meaning as that defined above and R$^{11A}$ has the same meaning as that defined above, in the presence of 1 to 10 equivalents of a base in an inert solvent at a temperature ranging from −78° C. to a boiling point of a solvent used for 1 minute to 24 hours.

As the inert solvent, tetrahydrofuran, ether, benzene, toluene and the like can be used alone or as a mixture thereof. Examples of the base include potassium tert-butoxide, sodium hydride, potassium hydride, lithium hexamethyldisilazane, and lithium diisopropylamide.

And also the compound (Ia2-1) or (Ib2-1) wherein

—X⁼⁼⁼Y— is —CH=CH— or —CH₂—CH₂—, R¹¹ is a lower alkoxycarbonyl group optionally substituted with a heterocyclic group and R² is a lower alkenyloxycarbonyloxy group can also be obtained using as a starting material the compound wherein

—X⁼⁼⁼Y— is —CH=CH— or —CH₂—CH₂—, R¹¹ is a carboxyl group, and R² is a lower alkenyloxycarbonyloxy group (the compound (Ia5) or (Ib5)) which is obtained in Preparation 4 explained below.

The reaction can be carried out by reacting the compound (Ia5) or (Ib5) with a corresponding lower alcohol optionally substituted with a heterocyclic group or an ester of a corresponding lower alcohol optionally substituted with a heterocyclic group in the presence or absence of a base in an inert solvent at a temperature ranging from 0° C. to a boiling point of a solvent used for one minute to 3 days.

As the inert solvent, lower alcohols such as methanol, ethanol, propanol and tert-butanol, tetrahydrofuran, ether, chloroform, methylene chloride, 1,2-dichloroethane, and the like may be used. The corresponding lower alcohol optionally substituted with a heterocyclic group or the ester of the corresponding lower alcohol optionally substituted with a heterocyclic group may be used as a solvent instead of the aforementioned inert solvent.

As the base, diisopropylethylamine, triethylamine, pyridine, 4-dimethyl-aminopyridine and the like may be used.

Furthermore, the compound wherein R¹ is a cyanomethyl group or a carboxymethyl group, R² is a lower alkenyloxycarbonyloxy group, and

—X⁼⁼⁼Y— is —CH₂—CH₂— can be obtained by catalytic hydrogenation of the compound wherein

—X⁼⁼⁼Y— is —CH=CH— and R¹¹ is a cyano group which is obtained by Preparation 1, or the compound wherein

—X⁼⁼⁼Y— is —CH=CH— and R¹¹ is a carboxyl group which is obtained by Preparation 4 mentioned below in a solvent such as benzene in the presence of a catalyst such as triphenylphosphine rhodium chloride in the presence of a hydrogen source such as hydrogen gas, ammonium formate at a temperature ranging from 0° C. to a boiling point of a solvent used for 1 minute to 100 hours.

Preparation 2

Among the compound (I), the compound wherein

—X⁼⁼⁼Y— is —CH=CH— or —CH₂—CH₂—, R¹¹ is a hydroxymethyl group, and R² is a lower alkenyloxycarbonyloxy group (the compound (Ia3) or (Ib3)) can be obtained according to the process set out below:

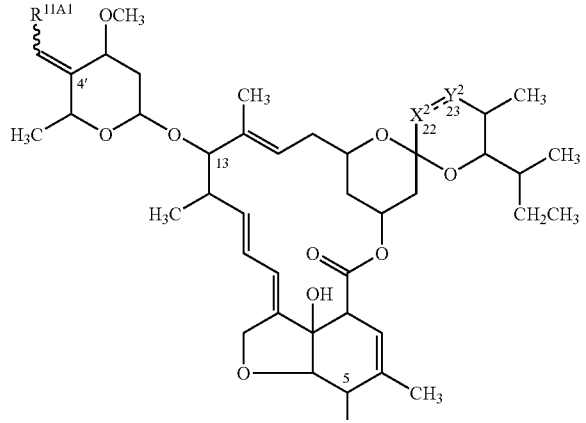

(Ia2-2) or (Ib2-2)

↓

(Ia3) or (Ib3)

(In the scheme, $R^{11A1}$ represents a lower alkoxycarbonyl group optionally substituted with a heterocyclic group, or a lower alkenyloxycarbonyl group among the definition of $R^{11A}$;

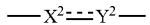

represents —CH=CH— or —CH$_2$—CH$_2$—, and $R^{2a}$ has the same meaning as that defined above.)

The compound (Ia3) or (Ib3) can be obtained by treating the compound, among the compound obtained in Preparation 1, wherein $R^{11A}$ is a lower alkoxycarbonyl group optionally substituted with a heterocyclic group, or a lower alkenyloxycarbonyl group, and

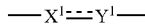

is —CH=CH— or —CH$_2$—CH$_2$— (compound (Ia2-2) or (Ib2-2)) with an equivalent to an excess amount of a reducing agent in an inert solvent at a temperature ranging from −78° C. to a boiling point of a solvent used for 1 minute to 24 hours.

As the inert solvent, methanol, ethanol, water, tetrahydrofuran, ether, benzene, toluene, pyridine, hexane, methylene chloride, chloroform, 1,2-dichloroethane, and the like may be used alone or as a mixture thereof. Examples of the reducing agent include sodium borohydride, lithium aluminium hydride, and diisobutylaluminium hydride.

Furthermore, the compound wherein $R^{11}$ is a halomethyl group can be obtained by treating the compound (Ia3) or (Ib3) obtained above wherein $R^{11}$ is a hydroxymethyl group with a halogenating agent in the presence or absence of a base in an inert solvent at a temperature ranging from −78° C. to a boiling point of a solvent used for 1 minute to 24 hours.

As the inert solvent, methylene chloride, chloroform, 1,2-dichloroethane, benzene, ether, tetrahydrofuran, and the like may be used alone or as a mixture thereof. As the halogenating agent, p-toluenesulfonyl chloride, thionyl chloride, thionyl bromide, and the like may be used.

As the base, diisopropylethylamine, triethylamine, pyridine, 4-dimethylaminopyridine, and the like may be used.

Furthermore, the compound wherein $R^{11}$ is an aminomethyl group can be obtained by reacting the compound wherein $R^{11}$ is a halomethyl group with an azide-formation agent in an inert solvent at a temperature ranging from −78° C. to a boiling point of a solvent used for 1 minute to 24 hours and then carrying out reduction in a conventional manner.

As the azide-formation agent, sodium azide, potassium azide, and the like may be used.

As the inert solvent, ether, tetrahydrofuran, and the like may be used alone or as a mixture thereof.

Preparation 3

Among the compound (I), the compound wherein

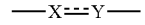

is —CH=CH— or —CH$_2$—CH$_2$—, $R^{11}$ is a formyl group, and $R^2$ is a lower alkenyloxycarbonyloxy group (the compound (Ia4) or (Ib4)) can be obtained by the process set out below:

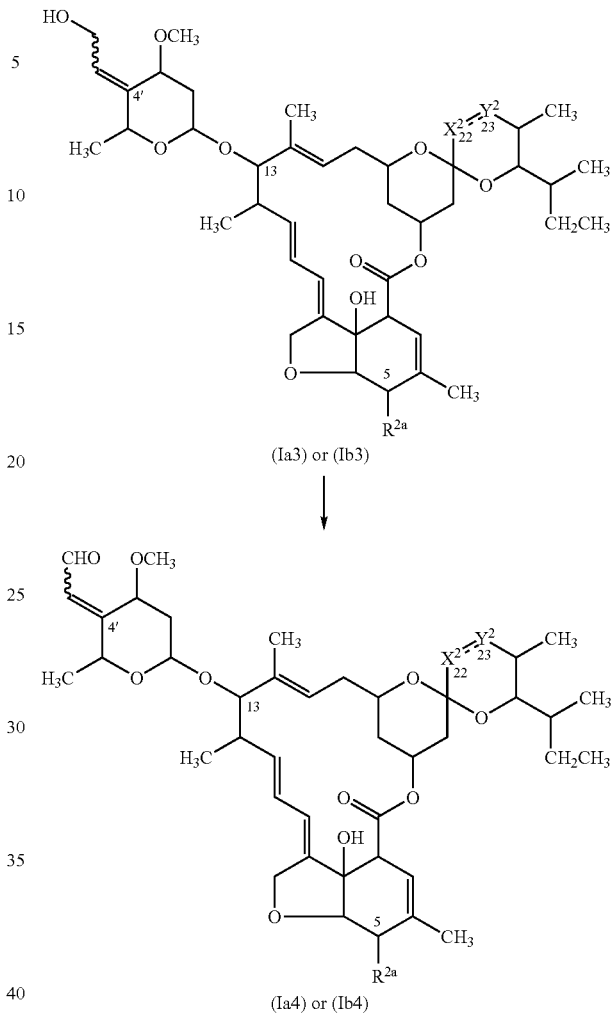

(In the scheme, $R^{2a}$ and

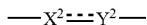

have the same meanings as those defined above, respectively.)

The compound (Ia4) or (Ib4) can be obtained by treating the compound (Ia3) or (Ib3) obtained in Preparation 2 with an equivalent to an excess amount of an oxidizing agent in an inert solvent at a temperature ranging from −78° C. to a boiling point of a solvent used for 1 minute to 24 hours.

As the inert solvent, water, tetrahydrofuran, ether, benzene, hexane, methylene chloride, chloroform, 1,2-dichloroethane, tert-butanol, and the like may be used alone or as a mixture thereof. Examples of the oxidizing agent include pyridinium chlorochromate, pyridinium dichromate, manganese dioxide, and potassium permanganate.

And also, the compound (Ia4) or (Ib4) can also be obtained from the compound (Ia2-2) or (Ib2-2), which is used as a starting material in Preparation 2, by controlling reaction conditions for reduction described in Preparation 2. Examples of the reaction solvent, the reducing agent, equivalents of the reducing agent, the reaction time, and the reaction temperature for the reduction of the compound (Ia2-2) or (Ib2-2) to obtain the compound (Ia4) or (Ib4) include those exemplified in Preparation 2.

Furthermore, the compound wherein $R^{11}$ is a vinyl group or a substituted vinyl group (for example, the compound wherein $R^{11}$ is —CH=CH—COOH) can be obtained by subjecting the compound (Ia4) or (Ib4), which is obtained above wherein $R^{11}$ is a formyl group, to the Wittig reaction.

Examples of the solvent, the reaction temperature, equivalents of the reagent, and the reaction time for the Wittig reaction are similar to those described in Preparation 1.

Preparation 4

Among the compound (I), the compound wherein

is —CH=CH— or —CH$_2$—CH$_2$—, $R^{11}$ is a carboxyl group, and $R^2$ is a lower alkenyloxycarbonyloxy group (the compound (Ia5) or (Ib5)) can be obtained by the process set out below:

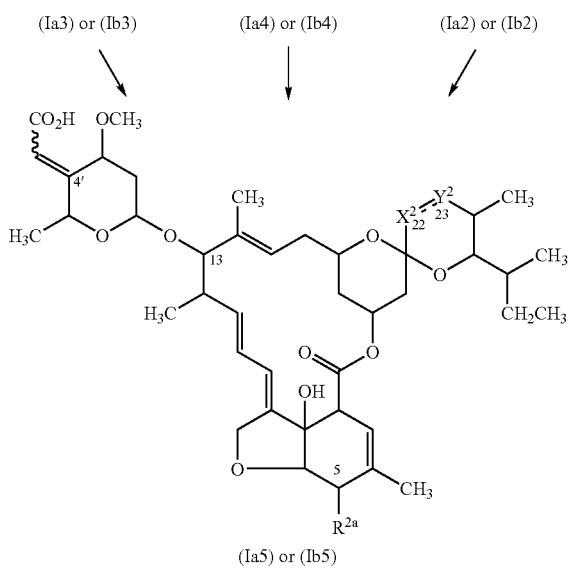

(In the scheme, $R^{2a}$ and

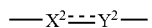

have the same meanings as those defined above, respectively.)

The compound (Ia5) or (Ib5) can be obtained by treating the compound (Ia3) or (Ib3) obtained in Preparation 2 with an equivalent to an excess amount of an oxidizing agent in an inert solvent at a temperature ranging from −78° C. to a boiling point of a solvent used for 1 minute to 24 hours.

As the inert solvent, water, tetrahydrofuran, ether, benzene, hexane, chloroform, methylene chloride, 1,2-dichloroethane, tert-butanol, and the like may be used alone or as a mixture thereof. Examples of the oxidizing agent include pyridinium dichromate, pyridinium chlorochromate, Jones reagent, chromium trioxide, and potassium permanganate.

The compound (Ia5) or (Ib5) can also be obtained, according to the aforementioned method for preparing the compound (Ia5) or (Ib5) from the compound (Ia3) or (Ib3), by oxidizing the formyl group of the compound (Ia4) or (Ib4) obtained in Preparation 3.

The compound (Ia5) or (Ib5) can also be obtained by hydrolyzing the compound (Ia2) or (Ib2) obtained in Preparation 1 in the presence of an equivalent to an excess amount of an acid or a base in an inert solvent.

Examples of the inert solvent include methanol, ethanol, water, tetrahydrofuran, ether, and acetonitrile. Examples of the acid include hydrochloric acid, sulfuric acid, and nitric acid, and examples of the base include sodium hydroxide, potassium hydroxide, and lithium hydroxide.

The compound (Ia5) or (Ib6) can also be obtained by treating the compound, wherein $R^{11A}$ is a lower alkenyloxycarbonyl group among the compound (Ia2) or (Ib2) obtained in Preparation 1, with an equivalent to an excess amount of a reducing agent in the presence of a palladium catalyst in an inert solvent at a temperature ranging from −78° C. to a boiling point of a solvent used for 1 minute to 24 hours.

Examples of the inert solvent include methanol and ethanol, and examples of the reducing agent include sodium borohydride, formic acid, and hydrazine. Examples of the palladium catalyst include tetrakis(triphenylphosphono)palladium.

The compound wherein $R^{11}$ is —CO—S—CH$_2$—CH$_2$—NH—CO—$R^x$ ($R^x$ has the same meaning as that defined above) can be obtained by further reacting the compound (Ia5) or (Ib5) obtained above wherein $R^{11}$ is a carboxyl group with HS—CH$_2$—CH$_2$—NH—CO—$R^x$ ($R^x$ has the same meaning as that defined above).

For the preparation of the compound wherein $R^{11}$ is —CO—S—CH$_2$—CH$_2$—NH—CO—$R^x$ ($R^x$ has the same meaning as that defined above) from the compound (Ia5) or (Ib5), reaction is generally carried out in the presence of a condensing agent and a base.

Examples of the solvent and the base used in the preparation of the compound wherein $R^{11}$ is —CO—S—CH$_2$—CH$_2$—NH—CO—$R^x$ ($R^x$ has the same meaning as that defined above) from the compound (Ia5) or (Ib5) include the inert solvents and the bases used in the reaction of the compound (Ia5) or (Ib5) with the compound (V) in Preparation 9 explained below.

As the condensing agent, benzotriazol-1-yloxytripyrrolidinophosphonium hexafluorophosphate and the like may be used, as well as the condensing agents used in the reaction of the compound (Ia5) or (Ib5) and compound (V) in Preparation 9 explained below.

Examples of the reaction time, the reaction temperature, equivalents of the reagent and the like for the preparation of the compound wherein $R^{11}$ is —CO—S—CH$_2$—CH$_2$—NH—CO—$R^x$ ($R^x$ has the same meaning as that defined above) from the compound (Ia5) or (Ib5) are similar to those exemplified in the reaction of the compound (Ia5) or (Ib5) with the compound (V) in Preparation 9 explained below.

Preparation 5

Among the compound (I), the compound wherein

—X===Y— is —CH=CH— or —CH$_2$—CH$_2$—, $R^{11}$ is a lower alkanoyloxymethyl group, a substituted or unsubstituted arylcarbonyloxymethyl group, or a heterocyclic carbonyloxymethyl group, and $R^2$ is a lower alkenyloxycarbonyloxy group (the compound (Ia6) or (Ib6)) can be obtained by the following method.

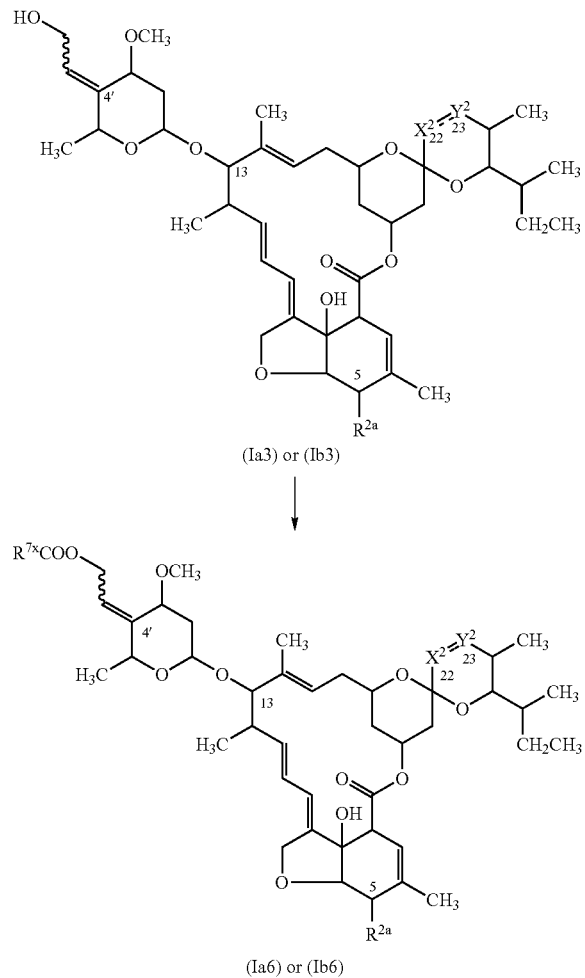

[In the scheme, $R^{7X}$ represents a lower alkyl group, a substituted or unsubstituted aryl group (the type and number of the substituent of the substituted aryl group are not particularly limited, and preferably, examples include from 1 to 5 substituents such as a halogen atom, an amino group, a hydroxyl group, and a nitro group), or a heterocyclic group (wherein the heterocyclic group may be substituted with a halogen atom or a lower alkoxycarbonyl group); $R^{2a}$ and

—X$^2$==Y$^2$— have the same meanings as those defined above, respectively. The lower alkyl group, aryl group, heterocyclic group, halogen atom, and lower alkoxycarbonyl group in the definition of $R^{7X}$ have the same meanings as those defined above, respectively.]

The compound (Ia6) or (Ib6) can be obtained by reacting the compound (Ia3) or (Ib3) obtained in Preparation 2 with an equivalent to an excess amount of the compound (IIIa) represented by the formula: $R^{7X}$COCl wherein $R^{7X}$ has the same meaning as that defined above, in the presence or absence of an equivalent to an excess amount of a base in an inert solvent at a temperature ranging from –78° C. to a boiling point of a solvent used for 1 minute to 24 hours.

Examples of the inert solvent include chloroform, methylene chloride, 1,2-dichloroethane and pyridine, and examples of the base include triethylamine, diisopropylethylamine, pyridine, and dimethylaminopyridine.

The desired compound (Ia6) or (Ib6) can also be obtained by reacting the compound (Ia3) or (Ib3) with an equivalent to an excess amount of the compound (IIIb) represented by the formula: $(R^{7X}CO)_2O$ wherein $R^{7X}$ has the same meaning as that defined above, in the presence or absence of an equivalent to an excess amount of a base in an inert solvent at a temperature ranging from –78° C. to a boiling point of a solvent used for 1 minute to 24 hours.

Examples of the inert solvent and the base used include those used in the reaction of the compound (Ia3) or (Ib3) and compound (IIIa).

The desired compound (Ia6) or (Ib6) can alternatively be obtained by reacting the compound (Ia3) or (Ib3) with an equivalent to an excess amount of the compound (IIIc) represented by the formula: $R^{7X}$COOH wherein $R^{7X}$ has the same meaning as that defined above, for 1 minute to 24 hours in the presence or absence of an equivalent to an excess amount of a base and in the presence of an equivalent to an excess amount of a condensing agent in an inert solvent at a temperature ranging from –78° C. to a boiling point of a solvent used.

Examples of the inert solvent and the base used include those used in the reaction of the compound (Ia3) or (Ib3) with the compound (IIIa). Examples of the condensing agent include 1-ethyl-3-(3-dimethylaminopropyl)carbodiimide (WSCI) hydrochloride and 1,3-dicyclohexylcarbodiimide.

Preparation 6

Among the compound (I), the compound wherein

—X===Y— is —CH=CH— or —CH$_2$—CH$_2$—, $R^{11}$ is —CH=N—OR$^3$ wherein $R^8$ has the same meaning as that defined above, or —CH=N—NH—CONH$_2$, and $R^2$ is a lower alkenyloxycarbonyloxy group (the compound (Ia7) or (Ib7)) can be obtained by using the compound (Ia4) or (Ib4) obtained in Preparation 3 as a starting material by the following method.

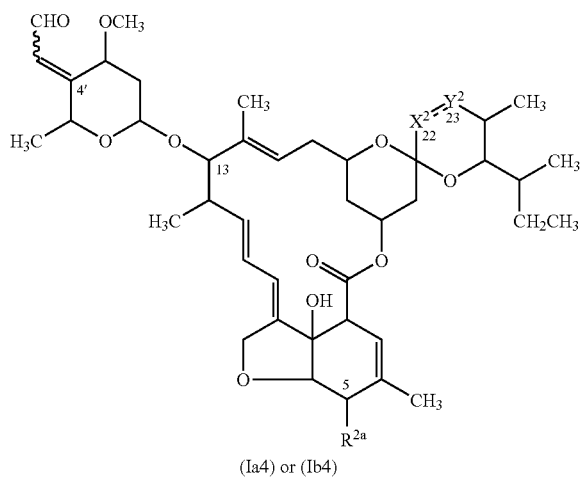

(Ia4) or (Ib4)

↓

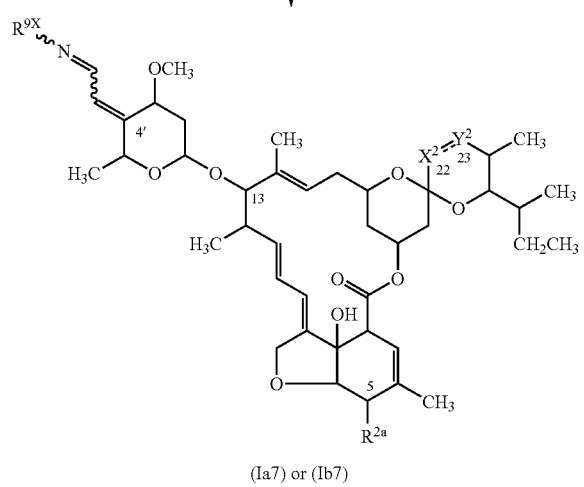

(Ia7) or (Ib7)

[In the scheme, $R^{9X}$ represents $OR^3$ wherein $R^3$ has the same meaning as that defined above, or —NH—CONH$_2$, and $R^{2a}$ and

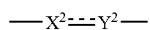

have the same meanings as those defined above, respectively.]

The compound (Ia7) or (Ib7) can be obtained by reacting the compound (Ia4) or (Ib4) with an equivalent to an excess amount of the compound (IV) represented by the formula: H$_2$N—OR$^8$ wherein $R^3$ has the same meaning as that defined above or a salt thereof (examples of the salt include acid addition salts having the same meaning as that defined above), or an equivalent to an excess amount of a semicarbazide or a salt thereof (examples of the salt include acid addition salts having the same meaning as that defined above) for 1 minute to 24 hours in the presence or absence of an equivalent to an excess amount of a base in an inert solvent at a temperature ranging from −78° C. to a boiling point of a solvent used.

Examples of the inert solvent include methanol and ethanol. Examples of the base include pyridine, triethylamine, and dimethylaminopyridine.

The compound wherein $R^{11}$ is —CH$_2$—NH—OR$^3$ can be obtained by reducing the compound obtained above wherein $R^{11}$ is —CH=N—OR$^3$.

The reduction can be carried out, for example, using a reducing reagent such as diisobutylaluminium hydride in an inert solvent such as methylene chloride, chloroform, and tetrahydrofuran.

Preparation 7

Among the compound (I), the compound wherein

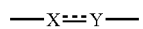

is —CH=CH— or —CH$_2$—CH$_2$—, $R^{11}$ is a tetrahydropyranyloxymethyl group, and $R^2$ is a lower alkenyloxycarbonyloxy group (the compound (Ia8) or (Ib8)) can be obtained by using the compound (Ia3) or (Ib3) obtained in Preparation 2 by the following method.

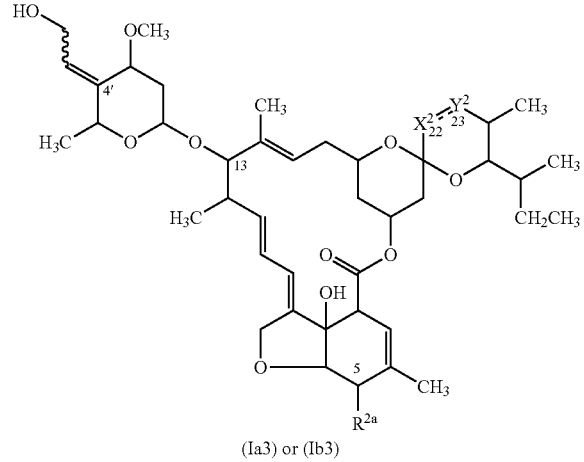

(Ia3) or (Ib3)

↓

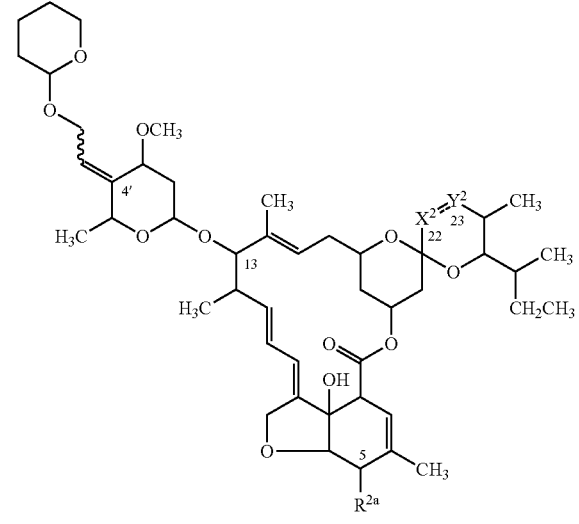

(Ia8) or (Ib8)

(In the scheme, $R^{3a}$ and

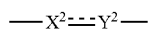

have the same meanings as those defined above, respectively.)

The compound (Ia8) or (Ib8) can be obtained by reacting the compound (Ia3) or (Ib3) obtained in Preparation 2 with an equivalent to an excess amount of dihydropyran in the presence of an acid catalyst in an inert solvent.

Examples of the acid catalyst include hydrochloric acid, p-toluenesulfonic acid, and pyridinium p-toluenesulfonate. Examples of the inert solvent include chloroform and methylene chloride.

Preparation 8

Among the compound (I), the compound wherein

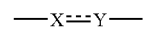

is —CH=CH— or —CH$_2$—CH$_2$—, $R^{11}$ is an aminomethyl group or a methylaminomethyl group, and $R^2$ is a lower alkenyloxycarbonyloxy group (the compound (Ia9) or (Ib9)) can be obtained by using the compound (Ia4) or (Ib4) obtained in Preparation 3 as a starting material by the following method.

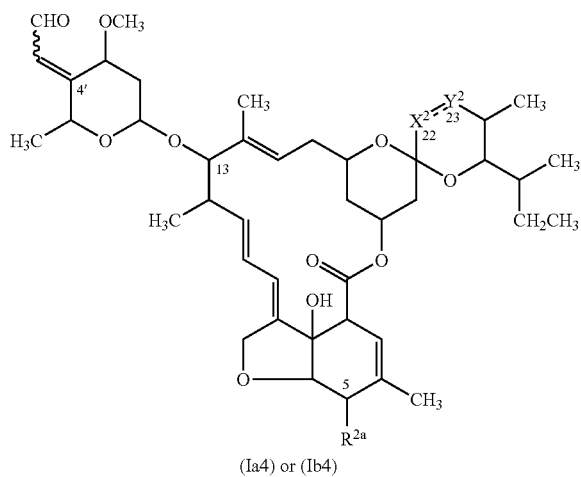

(Ia4) or (Ib4)

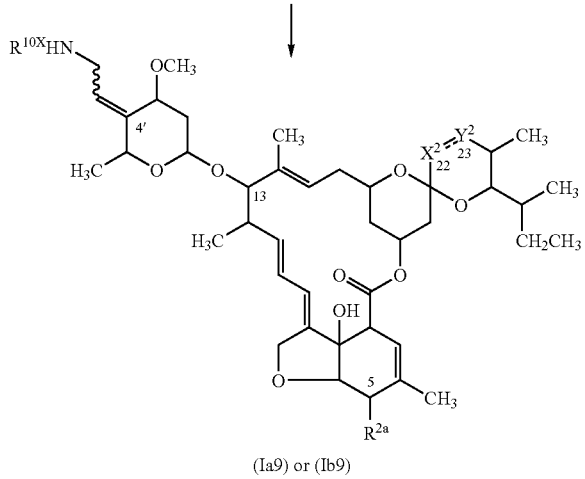

(Ia9) or (Ib9)

(In the scheme, $R^{10X}$ represents a hydrogen atom or a methyl group, and $R^{2a}$ and

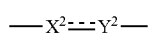

have the same meanings as those defined above, respectively.)

Among the compound (Ia9) or (Ib9), the compound wherein $R^{10X}$ is a hydrogen atom can be obtained by reacting the compound (Ia4) or (Ib4) with an equivalent to an excess amount of hexamethyldisilazane in the presence of a catalytic amount to an excess amount of a metal salt in an inert solvent at a temperature ranging from −78° C. to a boiling point of a solvent used for 1 minute to 24 hours, and then adding an equivalent to an excess amount of a reducing agent.

Examples of the inert solvent include methyl acetate, ethyl acetate, propyl acetate, isopropyl acetate, methanol, and ethanol.

Examples of the metal salt include zinc chloride, and examples of the reducing agent include sodium borohydride, formic acid, hydrogen gas, and lithium aluminium hydride.

Among the compound (Ia9) or (Ib9), the compound wherein $R^{10X}$ is a methyl group can be obtained by using heptamethyldisilazame instead of hexamethyldisilazane described above.

Preparation 9

Among the compound (I), the compound wherein

is —CH=CH— or —CH$_2$—CH$_2$—, $R^{11}$ is CON($R^5$)($R^6$) wherein $R^5$ and $R^6$ have the same meanings as those defined above, respectively, and $R^2$ is a lower alkenyloxycarbonyloxy group (the compound (Ia10) or (Ib10)) can be obtained by using the compound (Ia5) or (Ib5) obtained in Preparation 4 as a starting material by the following method.

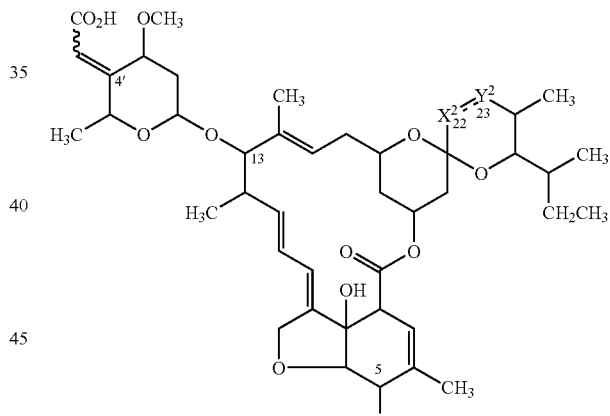

(Ia5) or (Ib5)

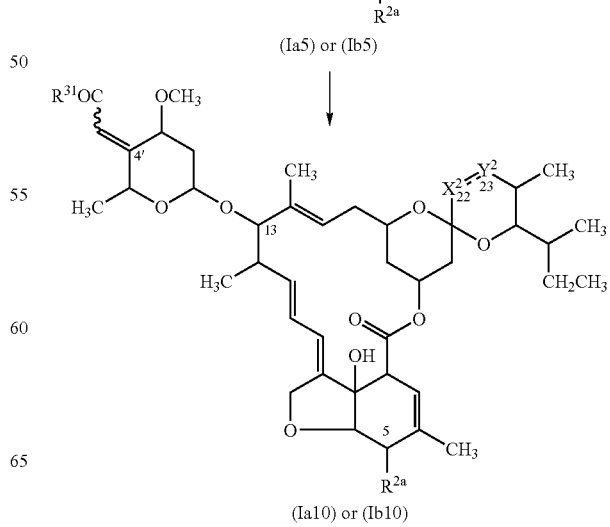

(Ia10) or (Ib10)

[In the scheme, $R^{31}$ represents —$N(R^5)(R^6)$ wherein $R^5$ and $R^6$ have the same meanings as those defined above, respectively, and $R^{2a}$ and

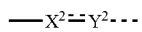

have the same meanings as those defined above, respectively.]

The compound (Ia10) or (Ib10) can be obtained by reacting the compound (Ia5) or (Ib5) with an equivalent to an excess amount of the compound (V) represented by the formula: $R^{31}H$ wherein $R^{31}$ has the same meaning as that defined above, for 1 minute to 24 hours in the presence of a base and a condensing agent in an inert solvent at a temperature ranging from −78° C. to a boiling point of a solvent used.

Examples of the inert solvent include chloroform, methylene chloride, methyl acetate, ethyl acetate, propyl acetate, isopropyl acetate, methanol, and ethanol.

Examples of the condensing agent include 1-ethyl-3-(3-dimethylaminopropyl)-carbodiimide (WSCI) hydrochloride, and 1,3-dicyclohexylcarbodiimide. Examples of the base include triethylamine, diisopropylethylamine, dimethylaminopyridine, and pyridine.

The compound (Ia10) or (Ib10) can also be obtained by treating the compound (Ia5) or (Ib5) with a chlorinating agent in an inert solvent or in the absence of a solvent at a temperature ranging from an ice-cooling temperature to a boiling point of a solvent used (at a boiling temperature of the chlorinating agent when no solvent is used) to convert the compound into a corresponding acid chloride, and reacting the resulting product with the compound (V) represented by the formula: $R^{31}H$ wherein $R^{31}$ has the same meaning as that defined above, in an inert solvent in the presence of a base at a temperature ranging from an ice-cooling temperature to a boiling point of a solvent used.

Examples of the chlorinating agent include phosphorus oxychloride, phosphorus pentachloride, phosphorus trichloride, thionyl chloride, and thionyl bromide.

Examples of the inert solvent for the chlorination include chloroform, methylene chloride, 1,2-dichloroethane, toluene, and benzene.

Examples of the inert solvent for the condensation reaction include chloroform, methylene chloride, methyl acetate, ethyl acetate, propyl acetate, isopropyl acetate, tetrahydrofuran, methanol, and ethanol.

Examples of the base include triethylamine, diisopropylethylamine, dimethylaminopyridine, and pyridine.

Preparation 10

Among the compound (I), the compound wherein $R^2$ is a lower alkenyloxycarbonyloxy group, or the compound as a synthetic intermediate for the compound (I) wherein the position corresponding to 5-position of the compound (I) is a tri(lower alkyl)silyloxy group such as tert-butyldimethylsilyloxy group (wherein the lower alkyl moiety of the tri(lower alkyl)silyloxy group has the same meaning as that defined in the aforementioned lower alkyl group and each of the lower alkyl group moiety may be the same or different) can be prepared by the method described in the Japanese Patent Publication (KOKOKU) No. (Hei)6-33273/1994, the Japanese Patent Unexamined Publication (KOKAI) No. (Hei)3-74397/1991 and the like, or a similar method thereto by using avermectin B1a monosaccharide, avermectin B2a monosaccharide, ivermectin monosaccharide and the like.

The compound wherein $R^1$ and the carbon atom at 4'-position combine to each other to form a carbonyl group in the compound (I) can be prepared by oxidizing the hydroxyl group at 4'-position of the compound (I) wherein 4'-position is a hydroxyl group by the method described in the Japanese Patent Publication (KOKOKU) No. (Hei)6-33273/1994, the Japanese Patent Unexamined Publication (KORAI) No. (Hei)3-74397/1991, or a similar method thereto.

Examples of oxidizing methods described in the Japanese Patent Publication (KOKOKU) No. (Hei)6-33273/1994, the Japanese Patent Unexamined Publication (KOKAI) No. (Hei)3-74397/1991 or the like include oxidation using phenyldichlorophosphate ($C_6H_5OPOCl_2$)/triethylamine (TEA)/dimethyl sulfoxide (DMSO), oxidation using tetrapropylammonium perruthenate ($(C_3H_7)_4NRuO_4$)/4-methylmorpholine-N-oxide (NMO) in methylene chloride in the presence of molecular sieves 4A (MS4A), oxidation using sulfur trioxide pyridine complex in dimethyl sulfoxide (DMSO) and the like.

Preparation 11

Among the compound (I), the compound wherein

is —CH=CH—, —$CH_2$—$CH_2$—, or —$CH_2$—C(=O)—, the bond between $R^1$ and the carbon atom at 4'-position is a double bond, and $R^2$ is a hydroxyl group (the compound (Ia11), the compound (Ib11), or the compound (Ie11)) can be prepared by deprotection at 5-position of the compound (the compound (A)), which is obtained by Preparations 1 to 10 and the like from the compound wherein the hydroxyl group at 5-position of the compound (Ia), the compound (Ib), or the compound (Ie) wherein 5-position is a hydroxyl group is protected with a tri(lower alkyl)silyl group such as tert-butyldimethylsilyl group (in which the lower alkyl moiety of the tri(lower alkyl)silyl group has the same meaning as that defined in the aforementioned lower alkyl group and each of the lower alkyl group moiety may be the same or different), or the compound (the compound (IA)) wherein $R^2$ is a lower alkenyloxycarbonyl group obtained by Preparations 1 to 10 and the like.

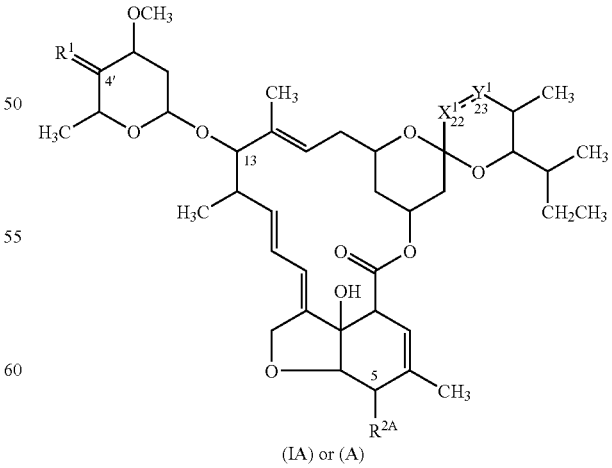

(IA) or (A)

-continued

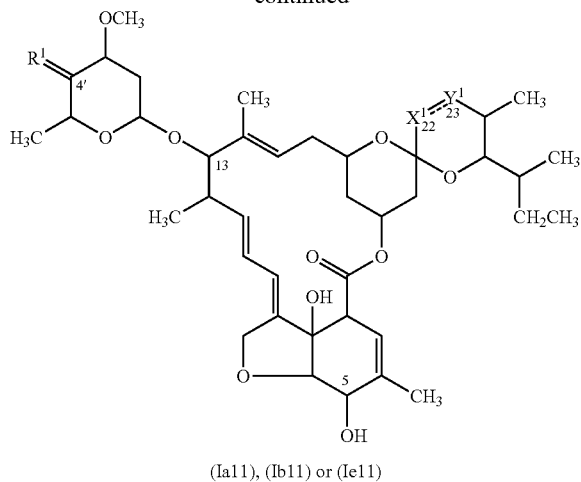

(Ia11), (Ib11) or (Ie11)

[In the scheme, $R^1$ and

—$X^1 \text{---} Y^1$— have the same meanings as those defined above, respectively, $R^{2A}$ represents a lower alkenyloxycarbonyloxy group wherein the lower alkyl moiety of the lower alkenyloxycarbonyloxy group has the same meaning as that defined in the aforementioned lower alkyl group, or a tri(lower alkyl) silyloxy group wherein the lower alkyl moiety of the tri (lower alkyl)silyloxy group has the same meaning as that defined in the aforementioned lower alkyl group and each of the lower alkyl group moiety may be the same or different.]

The lower alkenyloxycarbonyl group can be eliminated by reducing the compound (IA) obtained by Preparations 1 to 10 or the like in an inert solvent in the presence of a palladium compound such as tetrakis(triphenylphosphine) palladium by using sodium borohydride and the like as a hydrogen source.

The reaction is generally completed for 1 minute to 24 hours at a temperature ranging from −78° C. to a boiling point of a solvent used.

As the inert solvent, an etheric solvent such as tetrahydrofuran and ether, an alcoholic solvent such as ethanol, and the like may be used alone or as a mixture thereof.

The lower alkenyloxycarbonyloxy group at 5-position may sometimes be converted to a hydroxyl group depending on a reaction condition for carrying out a conversion of a functional group in other position.

And also the tri(lower alkyl)silyl group can be eliminated by treating the compound (A) obtained by the method according to Preparations 1 to 10 or the like in an inert solvent for 1 minute to 24 hours with a catalytic amount to an amount serving as a solvent of a desilylating agent at a temperature ranging from −78° C. to a boiling point of a solvent used.

As the inert solvent, tetrahydrofuran, ether, benzene, toluene, pyridine, isopropyl acetate, and the like may be used alone or as a mixture thereof. Examples of the desilylating agent include hydrogen fluoride, hydrochloric acid, hydrogen bromide, sulfuric acid, and hydrogen fluoride/pyridine complex.

The tri(lower alkyl)silyloxy group at 5-position may sometimes be converted to a hydroxyl group depending on a reaction condition for carrying out a conversion of a functional group in other position.

Preparation 12

The compound (IC) wherein $R^2$ and the carbon atom at 5-position are combined to form a carbonyl group can be prepared by oxidizing the compound (IB) wherein $R^2$ is a hydroxyl group among the compound (I) obtained by Preparation 11 or Preparations 13 to 15.

The compound (IC) can be obtained by treating the compound (IB) in an inert solvent with one equivalent to excess amount of an oxidizing agent at a temperature ranging from −78° C. to a boiling point of a solvent used. The reaction is generally completed for one minutes to two days.

Examples of the inert solvent include chloroform, methylene chloride, and 1,2-dichloromethane, and examples of the oxidizing agent include manganese dioxide, pyridinium chlorochromate, chromium trioxide, and pyridinium dichromate.

Furthermore, the compound wherein $R^2$ and the carbon atom at 5-position are combined to form a hydroxime group can be obtained by reacting the compound (IC) with hydroxylamine or a salt thereof (examples of the salt include acid addition salts having the same meaning as those defined above).

The reaction between the compound (IC) and hydroxylamine or a salt thereof can be carried out in an inert solvent in the presence of absence of a base at a temperature ranging from −78° C. to a boiling point of a solvent used, The hydroxyl amine or a salt thereof and the base can be used in an equivalent to an excess amount. The reaction is generally completed in 1 minute to 2 days.

Examples of the inert solvent include lower alcohols such as methanol, ethanol and propanol, ethers such as ether and tetrahydrofuran, and halogenated hydrocarbons such as chloroform, methylene chloride and 1,2-dichloroethane.

Examples of the base include pyridine, 2,6-dimethylpyridine, dimethylaminopyridine, triethylamine, and diisopropylamine.

Preparation 13

The compound (If1) wherein $R^2$ is a lower alkenyloxycarbonyloxy group,

—$X\text{---}Y$— is —$CH_2$—$CH(OH)$—, and $R^{11b}$ is a cyano group, a carboxyl group, a lower alkoxycarbonyl group, or a lower alkenyloxycarbonyl group can be obtained by treating, in the same manner as Preparation 1 or 4, the compound among the compound obtained in the above Preparation 10 wherein $R^2$ is a lower alkenyloxycarbonyloxy group, —$X\text{---}Y$— is —$CH_2$—$CH(OH)$—, and $R^1$ and the carbon atom at 4'-position are combined to form a carbonyl group.

The compound (If2) wherein $R^3$ is a hydroxyl group,

is —$CH_2$—CH(OH)—, and $R^{11b}$ is a cyano group, a carboxyl group, a lower alkoxycarbonyl group, or a lower alkenyloxycarbonyl group can be obtained from the compound (If1) according to the method described in Preparation 11.

Preparation 14

Among the compound (I), the compound (If3) wherein

is —$CH_2$—CH($R^{13a}$)— (wherein $R^{13a}$ represents a lower alkylcarbonyloxy group and wherein the lower alkylcarbonyloxy group has the same meaning as that defined above), $R^2$ is a lower alkenyloxycarbonyloxy group, and $R^{11b}$ is a cyano group, a lower alkoxycarbonyl group, or a lower alkenyloxycarbonyl group can be prepared by the method similar to Preparation 5 by using, as a raw material, the compound wherein $R^{11b}$ is a cyano group, a lower alkoxycarbonyl group, or a lower alkenyloxycarbonyl group among the compound (If1) obtained in Preparation 13.

Furthermore, the compound (If4) wherein $R^2$ is a hydroxyl group,

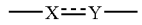

is —$CH_2$—CH($R^{13a}$)— (wherein $R^{13a}$ has the same meaning as that defined above), and $R^{11b}$ is a cyano group, a lower alkoxycarbonyl group, or a lower alkenyloxycarbonyl group can be obtained from the compound (If3) according to the method described in Preparation 11.

Preparation 15

Among the compound (I), the compound (If5) wherein

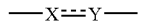

is —$CH_2$—CH($R^{13}$)— (wherein $R^{13}$ has the same meaning as that defined above), $R^2$ is a hydroxyl group or a lower alkenyloxycarbonyloxy group, and $R^{11b}$ is a carboxyl group can be obtained by hydrolyzing, in an ordinary manner, the compound wherein

is —$CH_2$—CH($R^{13}$)— (wherein $R^{13}$ has the same meaning as that defined above), and $R^{11b}$ is a cyano group, a lower alkoxycarbonyl group, or a lower alkenyloxycarbonyl group among the compound (I) obtained in Preparation 13 or 14.

Furthermore, the compound (If5-i) wherein $R^2$ is a lower alkenyloxycarbonyl group among the compound (If5) can be converted, according to the method described in Preparation 11, to the compound (If5-ii) wherein $R^2$ is a hydroxyl group among the compound (If5).

Preparations of the compound wherein

between $R^1$ and the carbon atom at 4'-position is a single bond (compound (ID)) among the compound (I) will be explained below.

Preparation 16

Compound (ID2) wherein $R^2$ is a lower alkenyloxycarbonyloxy group and $R^1$ is a methoxy group substituted with a lower alkoxycarbonyl group (wherein the lower alkyl moiety of the lower alkoxycarbonyl group may be substituted with a heterocyclic group) can be obtained by reacting the compound (ID1) wherein $R^2$ is a lower alkenyloxycarbonyloxy group and $R^1$ is a hydroxyl group among the compound (I) with a lower alkyl diazoacetate derivative such as ethyl diazoacetate and diethyl diazomalonate.

Furthermore, the compound (ID3) wherein $R^2$ is a lower alkenyloxycarbonyloxy group and $R^1$ is a methoxy group substituted with a carboxyl group can be obtained by treating the resulting compound (ID2) with a base such as alcoholic potassium hydroxide.

And also the compound (ID4) wherein $R^2$ is a lower alkenyloxycarbonyloxy group and $R^1$ is a methoxy group substituted with a cyano group and a lower alkoxycarbonyl group (wherein the lower alkyl moiety of the lower alkoxycarbonyl group may be substituted with a heterocyclic group) can be obtained by reacting the compound (ID1) with a lower alkyl diazocianoacetate derivative such as ethyl diazocianoacetate.

And also, the compound (ID5) wherein $R^2$ is a lower alkenyloxycarbonyloxy group and $R^1$ is a methoxy group substituted with an aryl group and a lower alkoxycarbonyl group (wherein the lower alkyl moiety of the lower alkoxycarbonyl group may be substituted with a heterocyclic group) can be obtained by reacting the compound (ID1) with a lower alkyl diazoarylacetate derivative such as ethyl diazophenylacetate.

Furthermore, the compound wherein $R^2$ is a lower alkenyloxycarbonyloxy group and $R^1$ is a methoxy group substituted with a cyano group and a carboxyl group or with an aryl group and a carboxyl group can be obtained by reacting the compound (ID4) or the compound (ID5) with a base such as alcoholic potassium hydroxide.

Preparation 17

The compound (ID6) wherein $R^2$ is a lower alkenyloxycarbonyloxy group and $R^1$ is a methoxy group substituted with —CON($R^{9X}$)($R^{10X}$) (wherein $R^{9X}$ and $R^{10X}$ have the same meaning as those of the aforementioned $R^9$ and $R^{10}$, respectively) can be obtained by reacting the compound (ID3) obtained in Preparation 16, wherein $R^2$ is a lower alkenyloxycarbonyloxy group and $R^1$ is a methoxy group substituted with a carboxyl group, with a cyclic amine compound such as piperazine or morpholine in the presence of a condensing agent.

Examples of the condensing agent include 1-ethyl-3-(3-dimethylaminopropyl)-carbodiimide (WSCI) hydrochloride and 1,3-dicyclohexylcarbodiimide.

And also the compound (ID7) wherein $R^2$ is a lower alkenyloxycarbonyloxy group and $R^1$ is a methoxy group substituted with —COR$^{8d}$ (wherein R$^{8d}$ represents an arylalkyloxy group wherein said aryl group may contain one or more hetero atoms as ring-constituting atoms) can be obtained by reacting the compound (ID3) with an arylalkylalcohol (wherein said aryl group may contain one or more hetero atoms as ring-constituting atoms) in the presence of a condensing agent.

Preparation 18

The compound (ID8) wherein R$^2$ is a lower alkenyloxycarboyloxy group and R$^1$ is a methoxy group substituted with a formyl group can be obtained by reducing the compound (ID3) wherein R$^2$ is a lower alkenyloxycarbonyloxy group and R$^1$ is a methoxy group substituted with a carboxyl group, or the compound (ID2) wherein R$^2$ is a lower alkenyloxycarbonyloxy group and R$^1$ is a methoxy group substituted with a lower alkoxycarbonyl group, which is obtained in Preparation 16.

Examples of a reducing agent include sodium borohydride, lithium aluminium hydride, and diisobutylaluminium hydride.

Furthermore, the compound (ID8) can be converted to the oxime compound wherein R$^2$ is a lower alkenyloxycarbonyloxy group (a hydroxime compound or an alkoxime compound) by reaction with a compound represented by H$_2$N—OR$^7$X wherein R$^7$X has the same meaning as that of the aforementioned R$^7$.

And also the compound (ID9) wherein R$^2$ is a lower alkenyloxycarbonyloxy group and R$^1$ is a methoxy group substituted with hydroxymethyl group can be obtained by treating the compound (ID3) or the compound (ID2) with a stronger reducing agent.

As the reducing agent, lithium triethylborohydride may be used.

Preparation 19

The compound (ID10) wherein R$^2$ is a lower alkenyloxycarbonyloxy group and R$^1$ is a methoxy group substituted with a p-nitrophenyl group can be obtained by reacting the compound (ID1) with p-nitrobenzyl bromide.

The compound (ID11) wherein R$^2$ is a lower alkenyloxycarbonyloxy group and R$^1$ is a methoxy group substituted with a p-aminophenyl group can be obtained by reducing the compound (ID10).

The reduction can be carried out, for example, by catalytic hydrogenation in the presence of palladium carbon catalyst.

Preparation 20

Another compound (ID) can be obtained by using the compound (ID9), as a starting material, wherein R$^2$ is a lower alkenyloxycarbonyloxy group and R$^1$ is a methoxy group substituted with a hydroxymethyl group, which is obtained in Preparation 18.

The compound (ID11) wherein R$^2$ is a lower alkenyloxycarbonyloxy group and R$^1$ is a methoxy group substituted with a substituted or unsubstituted arylsulfonyloxymethyl group can be obtained by reacting the compound (ID9) with a substituted or unsubstituted arylsulfonyl chloride or the like in the presence of a base.

And also the compound (ID12) wherein R$^2$ is a lower alkenyloxycarbonyloxy group and R$^1$ is a methoxy group substituted with a halogenated methyl group can be obtained by halogenating the moiety of a hydroxyl group of the methoxy group at 4'-position of the compound (ID9) which is substituted with the hydroxymethyl group.

Examples of conditions for the halogenation include a reaction with triphenylphosphine/carbon tetrabromide in the presence of a base, and triphenylphosphine/iodine in the presence of a base.

Furthermore, by reacting the compound (ID12) with HNR$^{9Y}$R$^{10Y}$ (wherein R$^{9Y}$ and R$^{10Y}$ have the same meanings as those of the aforementioned R$^9$ and R$^{10}$, respectively) optionally in the presence of a base, the compound (ID13) can be obtained wherein R$^2$ is a lower alkenyloxycarbonyloxy group and R$^1$ is a methoxy group substituted with CH$_2$NR$^{9Y}$R$^{10Y}$ (wherein R$^{9Y}$ and R$^{10Y}$ hare the same meaning as those defined above).

And also the compound wherein R$^2$ is a lower alkenyloxycarbonyloxy group and R$^1$ is a methoxy group substituted with an azide methyl group can be obtained by azide formation of the compound (ID12) which is obtained in Preparation 20.

Examples of conditions for the azide formation include reactions with an alkali azide such as sodium azide, potassium azide in a polar solvent.

Furthermore, the compound (ID15) wherein R$^2$ is a lower alkenyloxycarbonyloxy group and R$^1$ is a methoxy group substituted with an aminomethyl group can be obtained by reducing the compound (ID14).

Examples of conditions for the reduction include reduction by catalytic hydrogenation in the presence of a hydrogen source such as hydrogen gas or hydrazine or reduction using triphenylphosphine, which are ordinarily used.

Furthermore, the compound (ID16) wherein R$^2$ is a lower alkenyloxycarbonyloxy group and R$^1$ is a methoxy group substituted with a lower alkanoylaminomethyl group can be obtained by lower-alkanoylation of the compound (ID15).

Examples of the method for the lower-alkanoylation include reaction of the compound (ID15) with a halogenated lower alkanoyl compound or a method comprising reaction with an acid anhydride.

Preparation 21

The compound (ID17) wherein R$^2$ is a lower alkenyloxycarbonyloxy group, and R$^1$ is a methoxy group substituted with a lower alkenyloxycarbonyl group, and the compound (ID18) wherein R$^2$ is a lower alkenyloxycarbonyloxy group, and R$^1$ is a a methoxy group substituted with a cyano group can be obtained according to the method described in Preparation 16, which is for preparation of the compound (ID2) wherein R$^2$ is a lower alkenyloxycarbonyloxy group and R$^1$ is a methoxy group substituted with a lower alkoxycarbonyl group (wherein the lower alkyl moiety of the lower alkoxycarbonyl group may be substituted with a heterocyclic group).

The compound (ID19) wherein R$^2$ is a lower alkenyloxycarbonyloxy group and R$^1$ is substituted with —CH=N—NH—CONH$_2$ can be obtained by the compound (ID8) obtained by Preparation 18 wherein R$^2$ is a lower alkenyloxycarbonyloxy group and R$^1$ is a methoxy group substituted with a formyl group, and H$_2$N—NH—CONH$_2$ or a salt thereof such as an acid addition salt.

And also the compound (ID20) wherein R$^2$ is a lower alkenyloxycarbonyloxy group and R$^1$ is a methoxy group substituted with a vinyl group substituted with a lower alkenyloxycarbonyl group can be obtained by reacting the compound (ID8) with an appropriate Wittig reagent such as that prepared from allyldiethylphosphonoacetate.

Furthermore, the compound (ID21) wherein R$^2$ is a lower alkenyloxycarbonyloxy group and R$^1$ is a methoxy group substituted with —CH=CH—COOH can be prepared by treating the compound (ID20) under an appropriate deprotection condition such as deprotection by an acid, or deprotection by a hydrogen source such as sodium borohydride, hydrogen gas, and hydrazine in the presence of a metal catalyst such as tetrakis(triphenylphosphono)palladium.

And also the compound (ID22) wherein $R^2$ is a lower alkenyloxycarbonyloxy group and $R^1$ is a methoxy group substituted with —CO—S—$CH_2$—$CH_2$—NH—CO—$R^Y$ (wherein Y has the same meaning as that defined above) can be obtained by reacting the compound (ID3) obtained by Preparation 16, wherein $R^2$ is a lower alkenyloxycabonyloxy group and $R^1$ is a methoxy group substituted with a carboxyl group, with HS—$CH_2$—$CH_2$—NH—CO—$R^Y$ (wherein $R^Y$ has the same meaning as that defined above).

Preparation 22

The compound (ID23) wherein $R^1$ is —$OCHR^{1a}R^{1b}$, —$OCHR^{1aa}R^{1ba}$, or —$OCHR^{1ab}R^{1bb}$, and $R^2$ is a hydroxyl group can be obtained can be obtained by deprotection at 5-position of the compound according to Preparation 11 from the compound obtained according to Preparations 16 to 21 from the compound wherein $R^1$ is —$OCHR^{1a}R^{1b}$, —$OCHR^{1aa}R^{1ba}$, or —$OCHR^{1ab}R^{1bb}$, and the position corresponding to $R^2$ is tri(lower alkyl)silyloxy group such as tert-butyldimethylsilyloxy group (wherein the moiety of the lower alkyl group hydroxyl group of the tri(lower alkyl) silyloxy group has the same meaning as that defined above and each of the lower alkyl group may be the same or different), or of the compound obtained by Preparations 16 to 21.

Preparation 23

The compound (ID24) wherein $R^1$ is —$OCHR^{1a}R^{1b}$, —$OCHR^{1aa}R^{1ba}$, or —$OCHR^{1ab}R^{1bb}$, and $R^2$ and the carbon atom at 5-position are combined to form a carbonyl group can be obtained by oxidation of a hydroxyl group as $R^2$ of the compound (ID23) obtained by the aforementioned Preparation 22, in an ordinary manner.

Furthermore, the compound (ID25) wherein $R^2$ and the carbon atom at 5-position are combined to form a hydroxime group can be obtained by reacting the resulting compound (ID24) wherein $R^2$ and the carbon atom at 5-position are combined to form a carbonyl group with hydroxylamine or a salt thereof (examples of the salt include acid addition salts such as hydrochloride), in an ordinary manner.

The aforementioned methods are typical examples of the preparations of the compound (I), and the preparations of the compound (I) are not limited to those explained above. It can be easily understood by a person skilled in the art that the compound of the present invention can be obtained by other methods and the compound (I) can also be obtained by carrying out the above methods in an appropriate combination or with an appropriate modification or alteration, if necessary.

In addition, the compound (I) can also be obtained by an appropriate combination of the methods for converting a functional group which are usually used in the field of synthetic organic chemistry. For example, the compound (I) wherein $R^2$ is a methoxy group can be obtained by a conventional methylation of the hydroxyl group of the corresponding compound wherein $R^2$ is a hydroxyl group. Similarly, the compound (I) wherein $R^2$ is a lower alkoxyl group can be obtained by a conventional alkylation of the hydroxyl group of the corresponding compound wherein $R^2$ is a hydroxyl group.

For converting functional groups, desired conversions of functional groups can efficiently be made by protecting appropriate functional groups by methods for protection conventionally used in the field of synthetic organic chemistry [e.g. see Protective Groups in Organic Synthesis, T. W. Greene, John Wiley & Sons Inc. (1981)] and the like, if necessary.

Specific examples of the aforementioned preparation and other preparations are described in Examples, and accordingly, a person skilled in the art can prepare any compounds falling within the compound (I) by referring to the above general explanations and specific explanations in Examples, and by appropriately choosing starting materials, reagents and reaction conditions and adding an appropriate alteration or modification, if necessary.

Purification of the desired compounds in the aforementioned preparations can be made by an appropriate combination of methods ordinarily used in the filed of synthetic organic chemistry, for example, filtration, extraction, washing, drying, concentration, crystallization, and various chromatography and the like. Synthetic intermediates may be subjected to a next reaction without purification.

Isomers such as region isomers, geometrical isomers, tautomers and optical isomers may exist as the compounds (I). Any possible isomers and mixtures thereof in any proportion fall within the scope of the present invention. When a bond of a functional group that substitutes on a carbon atom forming a double bond is represented by a waved line in the specification, it means that the compound is an E- or Z-compound, or a mixture thereof.

For the preparation of a salt of the compound (I), a resulting salt, per se, may be purified when the compound (I) is obtained in the form of a salt. When a product is obtained in a free form, a salt may be isolated and purified after dissolving or suspending the product in a suitable solvent, and adding an acid or a base thereto to form a salt. The compounds (I) and salts thereof may exist in the forms of adducts with water or various solvents (i.e., hydrates or solvates), and these adducts also fall into the scope of the present invention. Moreover, any forms of crystal also fall into the scope of the present invention.

Specific examples of the compounds (I) obtained according to the present invention are shown in Tables 1 to 5. However, the compounds of the present invention are not limited to these examples.

TABLE 1

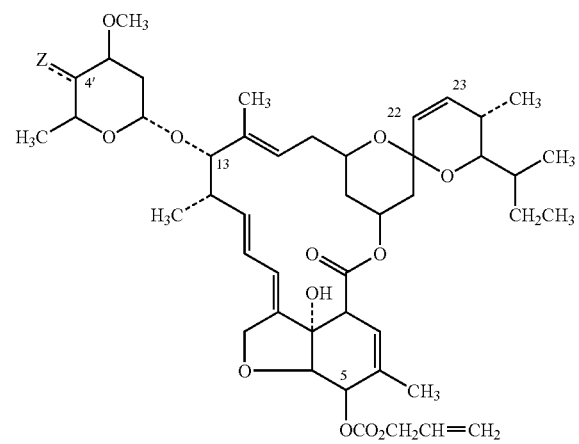

| Compound No. | Z | 4' |
|---|---|---|
| 1 | OH | Single bond |
| 2 | O | Double bond |

TABLE 1-continued

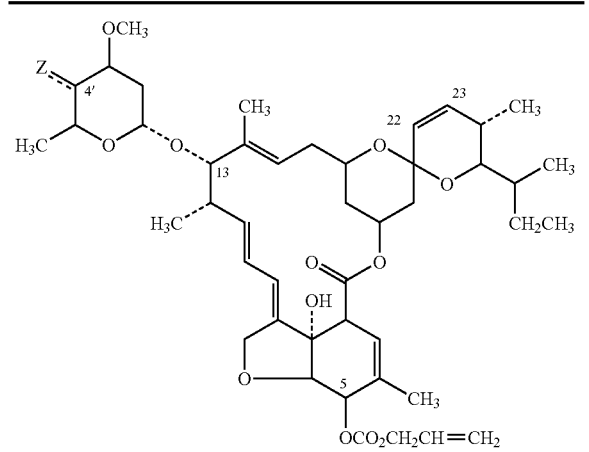

| Compound No. | Z | 4' |
|---|---|---|
| 3 | CHCO$_2$CH$_2$CH=CH$_2$ | Double bond |
| 4 | CHCN | Double bond |
| 5 | OCH$_2$CO$_2$CH$_2$CH$_3$ | Single bond |

TABLE 2

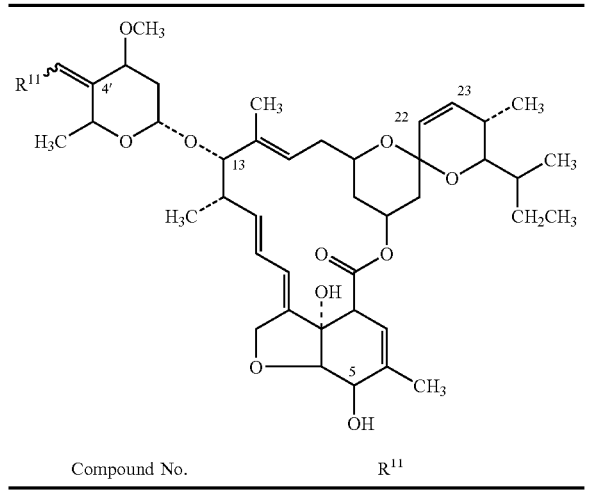

| Compound No. | R$^{11}$ |
|---|---|
| 6 | CO$_2$H |
| 7 | CN |
| 8 | CO$_2$CH$_2$CH=CH$_2$ |
| 9 | CO$_2$CH$_2$CH$_3$ |
| 10 | CH$_2$OH |
| 11 | CH$_2$Cl |
| 12 | CO$_2$C(CH$_3$)$_3$ |
| 13 | CON(morpholine) |
| 14 | CH$_2$N(morpholine) |
| 15 | CHO |
| 16 | CH$_2$OCO-(3-pyridyl) |

TABLE 2-continued

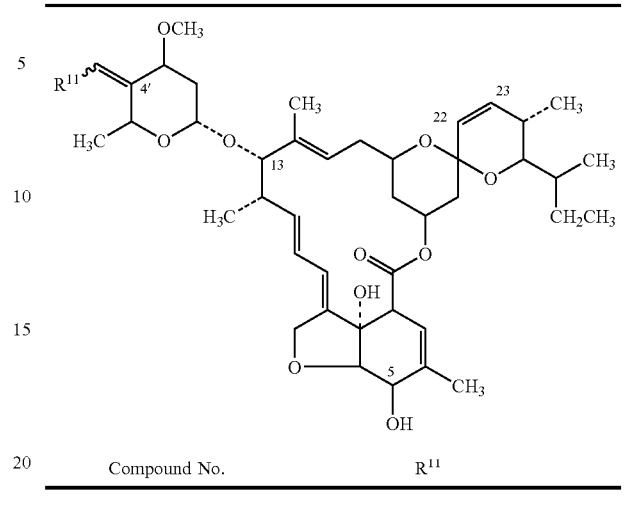

| Compound No. | R$^{11}$ |
|---|---|
| 17 | CH$_2$OCO-(4-pyridyl) |
| 18 | CH$_2$OCO-(4-nitrophenyl) |

TABLE 3

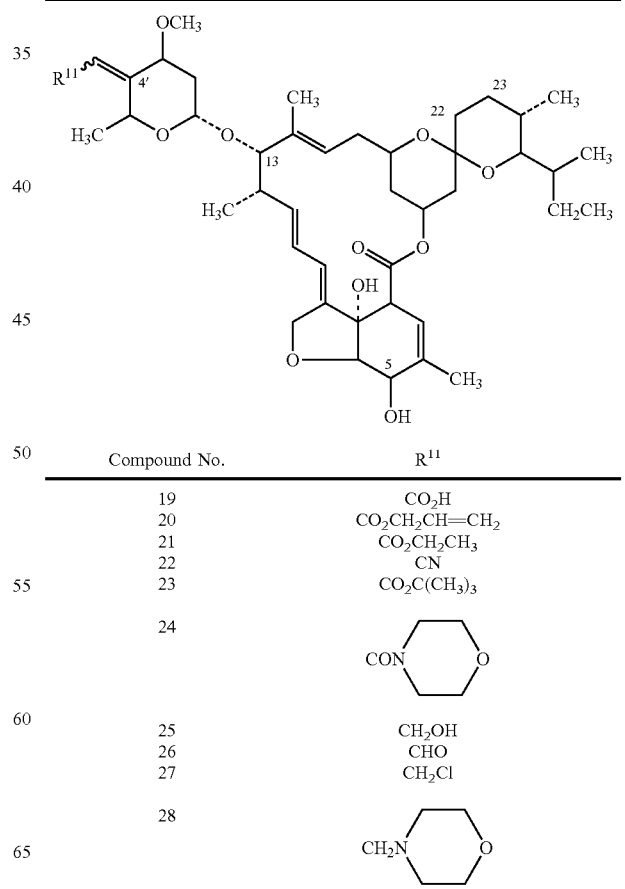

| Compound No. | R$^{11}$ |
|---|---|
| 19 | CO$_2$H |
| 20 | CO$_2$CH$_2$CH=CH$_2$ |
| 21 | CO$_2$CH$_2$CH$_3$ |
| 22 | CN |
| 23 | CO$_2$C(CH$_3$)$_3$ |
| 24 | CON(morpholine) |
| 25 | CH$_2$OH |
| 26 | CHO |
| 27 | CH$_2$Cl |
| 28 | CH$_2$N(morpholine) |

TABLE 3-continued

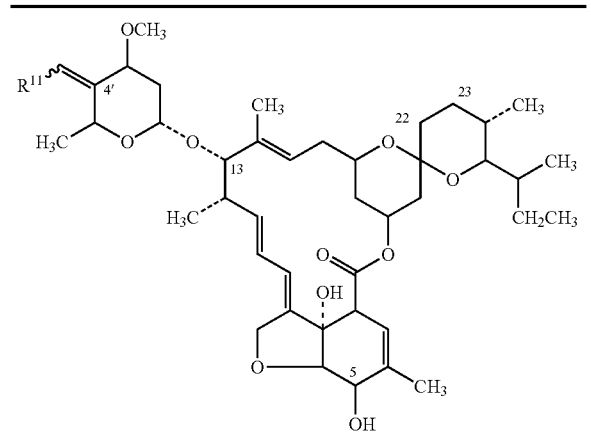

| Compound No. | $R^{11}$ |
|---|---|
| 29 | CH₂OCO-(3-pyridyl) |
| 30 | CH₂OCO-(4-pyridyl) |
| 31 | CH₂OCO-(4-NO₂-phenyl) |
| 32 | CO-piperidinyl |
| 33 | CO-piperazinyl |

TABLE 4

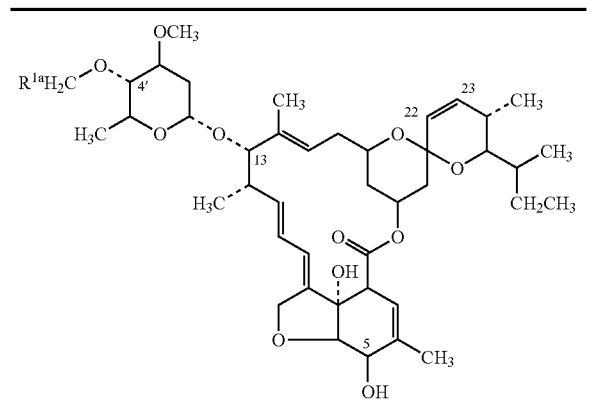

| Compound No. | $R^{1a}$ |
|---|---|
| 34 | $CO_2CH_2CH_3$ |
| 35 | $CO_2H$ |
| 36 | $CH_2OH$ |
| 37 | $CH_2Br$ |

TABLE 5

| Compound No. | $R^{1a}$ |
|---|---|
| 38 | $CO_2CH_2CH_3$ |
| 39 | $CO_2H$ |
| 40 | $CH_2OH$ |
| 41 | $CH_2Br$ |

As the active ingredient of the medicament of the present invention, one or more substances selected from the group consisting of the compounds represented by the general formula (I) in the free form and physiologically acceptable salts thereof, and hydrates thereof and solvates thereof can be used. Any mixture of isomers or an isomer in a pure form may be used. The medicament of the present invention is generally provided in the form of a pharmaceutical composition which comprises one or more pharmaceutical additives and the aforementioned substance as an active ingredient. The route of administration is not particularly limited, and the medicament can be orally administered using preparations such as tablets, granules, capsules, syrups and powders, or parenterally administered by means of injection, intrarectal administration, transdermal administration or the like. Pharmaceutical formulations suitable for oral or parenteral administration are well-known to persons skilled in the art, and they can appropriately choose pharmaceutical additives suitable for the manufacture of the pharmaceutical formulations.

The medicament of the present invention may be applied to various parasitic diseases, and the kinds of the parasitic disease are not particularly limited. The medicament of the present invention may be applied to a human or a mammal other than a human. When the medicament is applied to a mammal other than a human, the medicament may be administered as a pharmaceutical composition, or alternatively, a pharmaceutical composition or the aforementioned active ingredient per se may be added to a feed. The compound of the present invention may be applied as pesticides such as an agent for controlling injurious insects such as blowflies, cockroaches, fleas and the like.

EXAMPLES

The present invention will be explained more specifically with reference to the following examples. However, the present invention is not limited to these examples. Analytical data of the compounds described in the examples were measured by using the following apparatuses. The number and structure of the compounds are the same as those described in Table 1 to 5 set out above.

IR: Horiba FT-210
NMR: JEOL (Nippon Denshi) JMN-EX270
MS: JEOL (Nippon Denshi) JMS-AX505

Example 1

Compound 1

Under nitrogen atmosphere, Intermediate 1 (1.0 g) obtained in Reference Example 1 was dissolved in tetrahydrofuran (6.9 mL), and tetramethylethylenediamine (0.50 mL) and allyl chloroformate (0.17 mL) were successively added to the solution. The mixture was stirred for 30 minutes at −20° C. After purified water was added to the mixture, the mixture was extracted with ethyl acetate. The organic layer was washed with saturated brine and dried over anhydrous sodium sulfate. The solvent was evaporated under reduced pressure to give a crude product. The resulting crude product was purified by silica gel column chromatography with eluting solvents of hexane/ethyl acetate=4/1, 3/1, and 2/1 to give Compound 1 (0.80 g, 72%).

HRFABMS: Calcd. for $C_{45}H_{64}O_{13}$ $[M+Na]^+$ 835.4245. Found 835.4250.

IR (KBr) $\lambda_{max}(cm^{-1})$ 3473, 2966, 2933, 1747, 1716, 1464, 1379, 1344, 1308, 1254, 1184, 1161, 1116, 1080, 1051, 993

$^1$H NMR (270 MHz, $CDCl_3$, partial data) δ (ppm): 5.86 (5H, m), 5.57 (1H, m), 5.55 (1H, dd, J=9.9, 2.3 Hz), 5.38 (3H, m), 5.26 (1H, d, J=10.5 Hz), 4.98 (1H, m), 4.81 (1H, d, J=3.3 Hz), 4.64 (4H, m), 4.12 (1H, d, J=6.2 Hz), 3.96 (1H, br), 3.86 (2H, m), 3.52 (2H, m), 3.48 (3H, s), 3.37 (1H, d, J=2.3 Hz), 3.16 (1H, d, J=9.0 Hz), 2.51 (1H, m), 2.29 (4H, m), 2.02 (1H, dd, J=12.3, 3.6 Hz), 1.81 (3H, s), 1.49 (3H, s), 1.27 (3H, d, J=6.3 Hz), 1.15 (3H, d, J=6.9 Hz)

$^{13}$C NMR (67.8 MHz, $CDCl_3$) δ (ppm): 173.4, 154.8, 139.2, 138.0, 136.2, 135.1, 183.0, 131.4, 127.7, 124.7, 121.5, 120.4, 118.7, 118.2, 95.7, 95.0, 81.7, 80.8 (×2), 78.3, 76.0, 74.8, 73.5, 68.7, 68.5, 68.4, 68.3, 68.1, 56.6, 45.7, 40.4, 39.7, 36.5, 35.1, 34.2, 33.8, 30.5, 27.6, 20.1, 19.6, 17.7, 16.3, 15.1, 12.9, 12.0

Example 2

Compound 2

Under nitrogen atmosphere, Compound 1 (0.10 g) obtained in Example 1 was dissolved in dimethyl sulfoxide (1.2 mL). After triethylamine (54 μL) was added to the solution, a solution of sulfur trioxide/pyridine complex (97 mg) in dimethyl sulfoxide (1.2 mL) was slowly added dropwise to the mixture, and the mixture was stirred at 0° C. for 1 hour. After purified water was added to the reaction mixture, the reaction mixture was extracted with ethyl acetate. The organic layer was washed successively with purified water and saturated brine and dried over anhydrous sodium sulfate. The solvent was evaporated under reduced pressure to give a crude product. The resulting crude product was purified by silica gel column chromatography with eluting solvents of hexane/ethyl acetate=5/1 and 2/1 to give Compound 2 (0.67 g, 68%).

HRFABMS: Calcd. for $C_{45}H_{62}O_{13}$ $[M+Na]^+$ 833.4088. Found 833.4087.

IR (KBr) $\lambda_{max}(cm^{-1})$: 3471, 2966, 2933, 1743, 1456, 1379, 1344, 1308, 1254, 1182, 1161, 1118, 1076, 1051, 997

$^1$H NMR (270 MHz, $CDCl_3$, partial data) δ (ppm): 5.89 (5H, m), 5.57 (1H, m), 5.55 (1H, dd, J=9.9, 2.3 Hz), 5.37 (3H, m), 5.27 (1H, d, J=10.5 Hz), 5.05 (1H, m), 4.96 (1H, d, J=2.3 Hz), 4.65 (4H, m), 4.50 (1H, dd, J=12.8, 6.6 Hz), 4.25 (1H, dd, J=12.5, 6.3 Hz), 4.12 (1H, d, J=5.9 Hz), 4.07 (1H, br), 3.89 (1H, m), 3.56 (3H, s), 3.48 (1H, d, J=9.9 Hz), 3.37 (1H, d, J=2.0 Hz), 2.58 (1H, m), 2.50 (1H, dd, J=12.2, 6.2 Hz), 2.31 (3H, m), 2.09 (2H, m), 1.82 (3H, s), 1.53 (3H, s), 1.27 (3H, d, J=6.6 Hz), 1.17 (3H, d, J=6.9 Hz)

$^{13}$C NMR (67.8 MHz, $CDCl_3$) δ (ppm): 205.6, 173.3, 154.7, 139.6, 137.3, 136.3, 134.8, 133.0, 131.4, 127.7, 125.1, 121.5, 120.2, 118.7, 118.6, 95.7, 94.6, 82.2, 80.8 (×2), 78.1, 77.4, 74.8, 73.5, 70.7, 68.7, 68.4, 68.2, 58.5, 45.6, 40.4, 39.6, 39.0, 36.6, 36.1, 34.2, 30.5, 27.4, 20.1, 19.6, 16.3, 15.1, 13.9, 13.0, 12.0

Example 3

Compound 3

Under nitrogen atmosphere, allyl diethylphosphonoacetate (54 μL) was added to a 1.0 mol/L solution of lithium hexamethyldisilazane in tetrahydrofuran (0.17 mL) at 0° C., and the mixture was stirred at 0° C. for 1 hour. Then, a solution of Compound 2 (67 mg) obtained in Example 2 in tetrahydrofuran (1.0 mL) was slowly added dropwise to the mixture, and the mixture was further stirred at 0° C. for 1 hour. After a saturated aqueous ammonium chloride solution was added to the reaction mixture, the reaction mixture was extracted with ethyl acetate. The organic layer was washed successively with a saturated aqueous sodium hydrogencarbonate solution and saturated brine and dried over anhydrous sodium sulfate. The solvent was evaporated under reduced pressure to give a crude product. The resulting crude product was purified by silica gel column chromatography with eluting solvents of hexane/ethyl acetate=5/1 and 2/1 to give Compound 3 (0.43 g, 58%).

$^1$H NMR (270 MHz, $CDCl_3$, partial data) δ (ppm): 5.95 (2H, m), 5.88 (1H, s), 5.75 (4H, m), 5.56 (1H, m), 5.54 (1H, dd, J=9.6, 2.3 Hz), 5.35 (4H, m), 5.26 (2H, d, J=10.2 Hz), 5.16 (1H, brs), 5.03 (1H, m), 4.90 (1H, t, J=6.4 Hz), 4.63 (7H, m), 4.10 (1H, dd, J=5.3 Hz), 4.03 (1H, br), 3.84 (1H, m), 3.48 (2H, m), 3.36 (3H, s), 2.51 (1H, m), 2.33 (4H, m), 2.01 (1H, m), 1.80 (3H, s), 1.47 (3H, s), 1.39 (3H, d, J=6.3 Hz), 1.11 (3H, d, J=6.6 Hz)

Example 4

Compound 4

Under nitrogen atmosphere, diethylphospbonocyanomethyl (80 μL) was added to a 1.0 mol/L solution of lithium hexamethyldisilazane in tetrahydrofuran (0.49 mL) at 0° C., and the mixture was stirred at 0° C. for 1 hour. Then, a solution of Compound 2 (0.20 g) obtained in Example 2 in tetrahydrofuran (2.5 mL) was slowly added dropwise to the mixture, and the mixture was further stirred at 0° C. for 1 hour. After a saturated aqueous ammonium chloride solution was added to the reaction mixture, the reaction mixture was extracted with ethyl acetate. The organic layer was washed successively with a saturated aqueous sodium hydrogencarbonate solution and saturated brine and dried over anhydrous sodium sulfate. The solvent was evaporated under reduced pressure to give a crude product of Compound 4. The resulting crude product was purified by short silica gel column chromatography and used for the reaction in Example 7.

Example 5

Compound 5

Under nitrogen atmosphere, Compound 1 (0.30 g) obtained in Example 1 was dissolved in methylene chloride (0.60 mL), and diacetyl rhodium dimer (1.0 mg) was added to the solution. The mixture was stirred for 10 minutes at room temperature. Then, a solution of ethyl diazoacetate (43 µL) in methylene chloride (0.60 mL) was slowly added dropwise to the mixture, and the mixture was stirred at room temperature for 6 hours. After a saturated aqueous sodium hydrogencarbonate solution was added to the mixture, the mixture was extracted with methylene chloride. The organic layer was washed with saturated brine and dried over anhydrous magnesium sulfate. The solvent was evaporated under reduced pressure to give a crude product. The resulting crude product was purified by silica gel column chromatography with eluting solvents of hexane/ethyl acetate=6/1, 5/1, 4/1, and 2/1 to give Compound 5 (91 mg, 27%).

$^1$H NMR (270 MHz, CDCl$_3$, partial data) δ (ppm): 5.95 (5H, m), 5.55 (1H, dd, J=9.9, 2.3 Hz), 5.39 (3H, m), 5.27 (1H, d, J=10.5 Hz), 4.99 (1H, m), 4.76 (1H, d, J=3.0 Hz), 4.65 (4H, m), 4.40 (2H, d, J=2.0 Hz), 4.21 (2H, m), 4.12 (1H, d, J=6.3 Hz), 3.99 (3H, m), 8.78 (1H, m), 3.48 (1H, d, J=9.9 Hz), 3.44 (3H, 9), 3.37 (1H, d, J=2.3 Hz), 2.97 (1H, t, J=9.1 Hz), 2.51 (1H, m), 2.24 (4H, m), 2.02 (1H, m), 1.82 (3H, s), 1.49 (3H, s), 1.30 (6H, m), 1.12 (3H, d, J=6.9 Hz)

Example 6

Compound 6

Compound 3 (42 mg) obtained in Example 3 was dissolved in ethanol (500 µL), tetrakis(triphenylphosphine) palladium (1.0 mg) was added to the solution, and the mixture was stirred at 0° C. for 10 minutes. Then, sodium borohydride (5.0 mg) was added to the mixture, and then the mixture was stirred for 1 hour. After a saturated aqueous ammonium chloride solution was added to the reaction mixture, the reaction mixture was extracted with ethyl acetate. The organic layer was washed successively with a saturated aqueous sodium hydrogencarbonate solution and saturated brine and dried over anhydrous sodium sulfate. The solvent was evaporated under reduced pressure to give a crude product. The resulting crude product was purified by plate silica gel column chromatography with eluting solvents of chloroform/methanol=10/1 to give the desired compound (43 mg, 58%).

$^1$H NMR (270 MHz, CDCl$_3$, partial data) δ (ppm): 5.89 (1H, 9), 5.84 (1H, m), 5.76 (1H, d, J=9.9 Hz), 5.70 (1H, m), 5.55 (1H, dd, J=9.9, 2.3 Hz), 5.41 (1H, bra), 5.37 (1H, m), 5.08 (1H, brs), 5.04 (1H, m), 4.91 (1H, t, J=6.1 Hz), 4.67 (2H, brs), 4.59 (1H, m), 4.29 (1H, d, J=6.0 Hz), 4.04 (1H, brs), 3.96 (1H, d, J=6.3 Hz), 3.85 (1H, m), 3.49 (1H, d, J=9.9 Hz), 3.40 (3H, s), 3.28 (1H, d, J=2.0 Hz), 2.52 (1H, m), 2.31 (4H, m), 2.01 (1H, dd, J=11.9, 4.0 Hz), 1.86 (3H, s), 1.48 (3H, s), 1.40 (3H, d, J=6.2 Hz), 1.12 (3H, d, J=6.9 Hz)

$^{13}$C NMR (67.8 MHz, CDCl$_3$) δ (ppm): 173.6, 169.5, 158.4, 139.4, 138.2, 137.8, 136.3, 135.3, 127.7, 124.6, 120.4, 118.1, 117.9, 116.4, 96.7, 93.5, 81.2, 80.3, 79.1, 74.8, 70.6, 68.4 (x3), 67.7, 67.2, 56.6, 45.7, 40.5, 39.7, 36.5, 35.1, 34.3, 33.0, 30.5, 27.5, 19.9, 19.5, 19.1, 16.3, 14.9, 13.0, 12.0

Example 7

Compound 7

Compound 4 obtained in Example 4 (0.15 g) was dissolved in ethanol (1.8 mL), and tetrakis(triphenylphosphine) palladium (1.0 mg) was added to the solution. The mixture was stirred for 10 minutes at 0° C. Then, sodium borohydride (7.0 mg) was added to the mixture, and the mixture was stirred for 5 minutes. After a saturated aqueous ammonium chloride solution was added to the reaction mixture, the reaction mixture was extracted with ethyl acetate. The organic layer was washed successively with a saturated aqueous sodium hydrogencarbonate solution and saturated brine and dried over anhydrous sodium sulfate. The solvent was evaporated under reduced pressure to give a crude product. The resulting crude product was purified by silica gel column chromatography with eluting solvents of hexane/ethyl acetate=5/1 and 1/1 to give Compound 7 (0.13 g, 100%).

$^1$H NMR (270 MHz, CDCl$_3$, partial data) δ (ppm): 5.86 (1H, in), 5.75 (3H, m), 5.55 (1H, dd, J=9.9, 2.3 Hz), 5.45 (1H, s), 5.40 (1H, m), 5.37 (1H, s), 5.01 (1H, m), 4.88 (1H, t, J=4.2 Hz), 4.67 (2H, s), 4.56 (1H, m), 4.36 (1H, t, J=6.3 Hz), 4.29 (1H, d, J=6.0 Hz), 4.00 (1H, s), 3.96 (1H, d, J=6.3 Hz), 3.96 (1H, m), 3.53 (3H, s), 3.48 (1H, d, J=10.2 Hz), 3.29 (1H, d, J=2.3 Hz), 2.53 (1H, m), 2.29 (4H, m), 1.87 (3H, 9), 1.49 (3H, s), 1.34 (6H, d, J=6.6 Hz), 1.13 (3H, d, J=6.9 Hz)

Example 8

Compound 8

Intermediate 7 (49 mg, 53.0 µmol) obtained in Reference Example 7 was dissolved in tetrahydrofuran (1.6 mL). Hydrogen fluoride/pyridine complex (60 µL) was added to the solution, and the mixture was stirred at room temperature for 12 hours. After the reaction mixture was cooled to 0° C., a saturated aqueous sodium hydrogencarbonate solution (10 mL) was added for neutralization, and the mixture was extracted with ethyl acetate (10 mL×3). The organic layer was washed successively with a saturated aqueous sodium hydrogencarbonate solution (10 mL) and saturated brine (10 mL) and dried over anhydrous sodium sulfate. The solvent was evaporated under reduced pressure to give a crude product. The resulting crude product was purified on a silica gel plate with development solvents of chloroform/methanol=15/1 to give Compound 8 (41.0 mg, 84%).

HRFABMS: Calcd. for C$_{46}$H$_{64}$O$_{12}$ [M+Na]$^+$ 831.4295. Found 831.4296.

IR (KBr) λ$_{max}$(cm$^{-1}$): 3475, 2966, 2933, 1722, 1658, 1466, 1377, 1340, 1242, 1186, 1159, 1117, 1082, 1036, 995

$^1$H NMR (270 MHz, CDCl$_3$, partial data) δ (ppm): 5.94 (ddt, J=17.2, 10.2, 5.6 Hz, 1H), 5.88 (s, 1H), 5.83 (m, 1H), 5.75 (dd, J=9.9, 1.7 Hz, 1H), 5.72 (m, 2H), 5.54 (dd, J=9.9, 2.8 Hz, 1H), 5.40 (s, 1H), 5.35 (m, 1H), 5.33 (dd, J=17.2, 1.7 Hz, 1H), 5.25 (dd, J=10.2, 1.7 Hz, 2H), 5.16 (t, J=3.1 Hz, 1H), 5.03 (m, 1H), 4.89 (t, J=6.3 Hz, 1H), 4.69 (dd, J=14.5, 2.3 Hz, 1H), 4.63 (dd, J=14.5, 2.3 Hz, 1H), 4.62 (d, J=5.6 Hz, 2H), 4.58 (dq, J=6.6, 1.3 Hz, 1H), 4.27 (d, J=6.3 Hz, 1H), 4.03 (brs, 1H), 3.94 (d, J=6.3 Hz, 1H), 3.84 (m, 1H), 3.48 (d, J=9.6 Hz, 1H), 3.36 (s, 3H), 2.27 (q, J=2.3 Hz, 1H), 1.85 (s, 3H), 1.47 (s, 3H), 1.38 (d, J=6.6 Hz, 3H), 1.11 (d, J=6.6 Hz, 3H)

$^{13}$C NMR (67.8 MHz, CDCl$_3$) δ (ppm): 173.6, 165.4, 157.3, 139.5, 138.3, 137.8, 136.2, 135.3, 132.0, 127.8, 124.5, 120.4, 118.5, 118.0, 117.9, 116.5, 95.7, 93.5, 81.2, 80.3, 79.1, 74.8, 70.0, 68.4, 68.3 (×2), 67.7, 67.2, 65.0, 56.3, 45.7, 40.5, 39.7, 36.5, 35.1, 34.3, 32.8, 30.5, 27.5, 19.9, 19.4, 19.3, 16.4, 14.8, 13.0, 12.0

Example 9

Compound 9

In the manner similar to that of Example 8, Compound 9 (61.2 mg, 100%) was obtained from Intermediate 8 (70.0 mg, 76.8 µmol) obtained in Reference Example 8.

HRFABMS: Calcd. for $C_{45}H_{64}O_{12}$ [M+Na]$^+$ 819.4295. Found 819.4297.

IR (KBr) $\lambda_{max}$(cm$^{-1}$): 3448, 2966, 2933) 1720, 1655, 1460, 1379, 1340, 1244, 1186, 1159, 1116, 1082, 1084, 989

Example 10

Compound 10

In the manner similar to that of Example 8, Compound 10 (63.7 mg, 100%) was obtained from Intermediate 9 (70.0 mg, 80.5 µmol) obtained in Reference Example 9.

HRFABMS: Calcd. for $C_{43}H_{77}O_{11}$ [M+Na]$^+$ 777.4190. Found 777.4180.

IR (KBr) $\lambda_{max}$(cm$^{-1}$): 3453, 2966, 2931, 1735, 1714, 1456, 1376, 1340, 1244, 1184, 1160, 1117, 1080, 1038, 995

Example 11

Compound 11

In the manner similar to that of Example 8, Compound 11 (77.4 mg, 92%) was obtained from Intermediate 14 (97.0 mg, 80.5 µmol) obtained in Reference Example 14.

HRFABMS: Calcd. for $C_{43}H_{61}ClO_{10}$ [M+Na]$^+$ 795.3851, Found 795.3833.

IR (KBr) $\lambda_{max}$(cm$^{-1}$): 3455, 2966, 2933, 1712, 1456, 1376, 1340, 1255, 1184, 1159, 1116, 1080, 1038, 997

Example 12

Compound 12

Intermediate 10 (70.0 mg, 79.2 µmol) obtained in Reference Example 10 was dissolved in tert-butanol (0.8 mL). 4-Dimethylaminopyridine (3 mg, 23.7 µmol) and di-tert-butyl carbonate (25 mg, 118 µmol) were successively added, and the mixture was stirred at room temperature for 2 hours. After a saturated aqueous ammonium chloride solution (0.5 mL) was added to the reaction mixture, the reaction mixture was extracted with ethyl acetate (3 mL×3). The organic layer was washed with saturated brine (5 mL) and dried over anhydrous sodium sulfate. The solvent was evaporated under reduced pressure to give a crude product. Then, from the resulting crude product, Compound 12 (46.4 mg, 53% for the two steps) was obtained in the manner similar to that of Example 8.

HRFABMS: Calcd. for $C_{47}H_{68}O_{12}$ [M+Na]$^+$ 847.4608. Found 847.4599.

IR (KBr) $\lambda_{max}$(cm$^{-1}$): 3475, 2964, 2929, 1716, 1456, 1396, 1340, 1307, 1248, 1169, 1117, 1080, 1038, 997

Example 13

Compound 13

Intermediate 10 (70.0 mg, 79.2 µmol) obtained in Reference Example 10 was dissolved in methylene chloride (0.8 mL). Morpholine (10 µL, 103 µmol), anhydrous 1-hydroxybenzotriazol (20 mg, 103 µmol) and 1-ethyl-3-(3-dimethyl-aminopropyl)carbodiimide hydrochloride (20 mg, 103 µmol) were successively added to the solution, and the mixture was stirred at room temperature for 12 hours. After purified water (0.5 mL) was added to the reaction mixture, the reaction mixture was extracted with methylene chloride (5 mL×3). The organic layer was washed with saturated brine (3 mL) and dried over anhydrous sodium sulfate. The solvent was evaporated under reduced pressure to give a crude product. Then, from the resulting crude product, Compound 13 (66.3 mg, 100%, for the two steps) was obtained in the manner similar to that of Example 8.

HRFABMS: Calcd. for $C_{47}H_{67}NO_{12}$ [M+Na]$^+$ 860.4561. Found 860.4512.

IR (KBr) $\lambda_{max}$(cm$^{-1}$): 3456, 2964, 2927, 1735, 1735, 1648, 1460, 1379, 1338, 1244, 1182, 1161, 1117, 1074, 1045, 999

Example 14

Compound 14

Intermediate 14 (70.0 mg, 79.8 µmol) obtained in Reference Example 14 was dissolved in ethanol (1 mL). Morpholine (10 µL, 103 µmol) was added to the solution, and the mixture was stirred at 40° C. for 12 hours. After a saturated aqueous ammonium chloride solution (0.5 mL) was added to the reaction mixture, the reaction mixture was extracted with ethyl acetate (5 mL×3). The organic layer was washed with saturated brine (3 mL) and dried over anhydrous sodium sulfate. The solvent was evaporated under reduced pressure to give a crude product. Then, from the resulting crude product, Compound 14 (50.0 mg, 77%, for the two steps) was obtained in the manner similar to that of Example 8.

HRFABMS: Calcd. for $C_{47}H_{70}NO_{11}$ [M+Na]$^+$ 824.4949. Found 824.4938.

IR (KBr) $\lambda_{max}$(cm$^{-1}$): 3458, 2964, 2929, 1731, 1718, 1456, 1377, 1338, 1311, 1270, 1182, 1161, 1117, 1080, 1038, 995

Example 15

Compound 15

Intermediate 9 (70.0 mg, 80.5 µmol) obtained in Reference Example 9 was dissolved in methylene chloride (1 mL). Manganese dioxide (70.0 mg) was added to the solution, and the mixture was stirred at room temperature for 10 hours. After the reaction mixture was filtered by using Cerite®, the solvent was evaporated under reduced pressure to give a crude product. Then, from the resulting crude product, Compound 15 (86.2 mg, 65%, for the two steps) was obtained in the manner similar to that of Example 8.

Example 16

Compound 16

Intermediate 9 (50.0 mg, 57.5 µmol) obtained in Reference Example 9 was dissolved in methylene chloride (0.6 mL). Nicotinoyl chloride hydrochloride (15.0 mg, 86.2 µmol), diisopropylethylamine (15 µL, 86.2 µmoL), 1-ethyl-3-(3-dimethyl-aminopropyl)carbodiimide hydrochloride (17.0 mg, 86.2 µmol) and 4-dimethylaminopyridine (3 mg, 23.7 µmol) were successively added to the solution, and the mixture was stirred at room temperature for 4 hours. After a saturated aqueous ammonium chloride solution (0.5 mL) was added to the reaction mixture, the reaction mixture was extracted with methylene chloride (3 mL×3). The organic layer was washed with saturated brine (5 mL) and dried over anhydrous sodium sulfate. The solvent was evaporated under reduced pressure to give a crude product. Then, from the resulting crude product, Compound 16 (40.0 mg, 66%, for the two steps) was obtained in the manner similar to that of Example 8.

HRFABMS: Calcd. for $C_{49}H_{65}NO_{12}$ [M+Na]$^+$ 882.4404. Found 882.4399.

IR (KBr) $\lambda_{max}$(cm$^{-1}$): 3454, 2962, 2929, 1735, 1456, 1377, 1344, 1244, 1196, 1171, 1119, 1074, 1038, 993

Example 17

Compound 17

Intermediate 9 (70.0 mg, 80.5 μmol) obtained in Reference Example 9 was dissolved in methylene chloride (0.8 mL). Isonicotinoyl chloride hydrochloride (22.0 mg, 120 μmol), diisopropylethylamine (21 μL, 120 μmoL), 1-ethyl-3-(3-dimethyl-aminopropyl)carbodiimide hydrochloride (23.0 mg, 120 μmol) and 4-dimethylaminopyridine (5.00 mg, 40.0 μmol) were successively added to the solution, and the mixture was stirred at room temperature for 4 hours. After a saturated aqueous ammonium chloride solution (0.5 mL) was added to the reaction mixture, the reaction mixture was extracted with methylene chloride (3 mL×3). The organic layer was washed with saturated brine (5 mL) and dried over anhydrous sodium sulfate. The solvent was evaporated under reduced pressure to give a crude product. Then, from the resulting crude product, Compound 17 (60.0 mg, 87%, for the two steps) was obtained in the manner similar to that of Example 8.

HRFABMS: Calcd. for $C_{49}H_{65}NO_{12}$ [M+Na]$^+$ 882.4404. Found 882.4438.

IR (KBr) $\lambda_{max}$(cm$^{-1}$): 3458, 2964, 2931, 1732, 1456, 1377, 1326, 1279, 1182, 1159, 1119, 1084, 1039, 997

Example 18

Compound 18

Intermediate 9 (70.0 mg, 80.5 μmol) obtained in Reference Example 9 was dissolved in methylene chloride (0.8 mL). 4-Nitrobenzoyl chloride hydrochloride (22.0 mg, 120 μmol), diisopropylethylamine (21 μL, 120 μmoL), 1-ethyl-3-(3-dimethylaminopropyl)carbodiimide hydrochloride (23.0 mg, 120 μmol) and 4-dimethylaminopyridine (5.00 mg, 40.0 μmol) were successively added to the solution, and the mixture was stirred at room temperature for 4 hours. After a saturated aqueous ammonium chloride solution (0.5 mL) was added to the reaction mixture, the reaction mixture was extracted with methylene chloride (3 mL×3). The organic layer was washed with saturated brine (5 mL) and dried over anhydrous sodium sulfate. The solvent was evaporated under reduced pressure to give a crude product. Then, from the resulting crude product, Compound 18 (70.5 mg, 97%, for the two steps) was obtained in the manner similar to that of Example 8.

HRFABMS: Calcd. for $C_{50}H_{65}NO_{14}$ [M+Na]$^+$ 926.4303. Found 926.4338.

IR (KBr) $\lambda_{max}$(cm$^{-1}$): 3482, 2966, 2931, 1726, 1529, 1458, 1348, 1271, 1182, 1161, 1117, 1086, 1039, 997

Example 19

Compound 19

In the manner similar to that of Example 8, Compound 19 (48.8 mg, 80%) was obtained from Intermediate 16 (70.0 mg, 79.1 μmol) obtained in Reference Example 16.

HRFABMS: Calcd. for $C_{43}H_{62}O_{12}$ [M+Na]$^+$ 793.4139. Found 793.4185.

IR (KBr) $\lambda_{max}$(cm$^{-1}$): 3455, 2962, 2931, 1712, 1655, 1458, 1377, 1340, 1243, 1198, 1171, 1119, 1082, 1036, 993

Example 20

Compound 20

In the manner similar to that of Example 8, Compound 20 (61.1 mg, 100%) was obtained from Intermediate 11 (70.0 mg, 75.6 μmol) obtained in Reference Example 11.

HRFABMS: Calcd. for $C_{46}H_{66}O_{12}$ [M+Na]$^+$ 833.4452. Found 833.4457.

IR (KBr) $\lambda_{max}$(cm$^{-1}$): 3456, 2962, 2929, 1722, 1456, 1379, 1340, 1243, 1196, 1165, 1119, 1080, 1037, 993

Example 21

Compound 21

In the manner similar to that of Example 8, Compound 21 (61.1 mg, 100%) was obtained from Intermediate 12 (70.0 mg, 75.6 μmol) obtained in Reference Example 12.

HRFABMS: Calcd. for $C_{46}H_{66}O_{12}$ [M+Na]$^+$ 833.4452. Found 833.4457.

IR (KBr) $\lambda_{max}$(cm$^{-1}$): 3456, 2962, 2929, 1722, 1456, 1379, 1340, 1243, 1196, 1165, 1119, 1080, 1037, 993

Example 22

Compound 22

In the manner similar to that of Example 8, Compound 22 (123 mg, 92%) was obtained from Intermediate 13 (154 mg, 177 μmol) obtained in Reference Example HRFABMS: Calcd. for $C_{43}H_{61}NO_{10}$ [M+Na]$^+$ 774.4193. Found 774.4222.

IR (KBr) $\lambda_{max}$(cm$^{-1}$): 3483, 2960, 2931, 2221, 1712, 1458, 1377, 1340, 1243, 1196, 1174, 1119, 1086, 1027, 993

Example 23

Compound 23

In the manner similar to that of Example 12, Compound 23 (53.0 mg, 81%, for the two steps) was obtained from Intermediate 16 (70.0 mg, 79.1 μmol) obtained in Reference Example 16.

HRFABMS: Calcd. for $C_{47}H_{70}O_{12}$ [M+Na]$^+$ 849.4765. Found 849.4727.

IR (KBr) $\lambda_{max}$(cm$^{-1}$): 3479, 2964, 2931, 1716, 1456, 1377, 1339, 1248, 1171, 1119, 1035, 993

Example 24

Compound 24

In the manner similar to that of Example 13, Compound 24 (66.4 mg, 100%, for the two steps) was obtained from Intermediate 16 (70.0 mg, 79.1 μmol) obtained in Reference Example 16.

HRFABMS: Calcd. for $C_{47}H_{69}NO_{12}$ [M+Na]$^+$ 862.4717. Found 862.4731.

IR (KBr) $\lambda_{max}$(cm$^{-1}$): 3461, 2962, 2929, 1731, 1713, 1633, 1456, 1377, 1338, 1244, 1172, 1117, 1072, 1043, 996

Example 25

Compound 25

In the manner similar to that of Example 8, Compound 25 (34.0 mg, 65%) was obtained from Intermediate 15 (60.0 mg, 68.8 i<mol) obtained in Reference Example 15.

HRFABMS: Calcd. for $C_{48}H_{64}O_{11}$ [M+Na]$^+$ 779.4346. Found 779.4361.

IR (KBr) $\lambda_{max}$(cm$^{-1}$): 3455, 2962, 2929, 1722, 1456, 1379, 1340, 1306, 1244, 1196, 1165, 1119, 1072, 1036, 993

Example 26

Compound 26

In the manner similar to that of Example 15, Compound 26 (48.0 mg, 79%, for the two steps) was obtained from Intermediate 15 (70.0 mg, 80.3 µmol) obtained in Reference Example 15.

HRFABMS: Calcd. for $C_{43}H_{62}O_{11}$ [M+Na]$^+$ 777.4190. Found 777.4179.

IR (KBr) $\lambda_{max}$(cm$^{-1}$): 3473, 2962, 2931, 1713, 1674, 1456, 1377, 1338, 1244, 1174, 1119, 1074, 1041, 995.

Example 27

Compound 27

In the manner similar to that of Example 8, Compound 27 (42.0 mg, 80%) was obtained from Intermediate 19 (60.0 mg, 67.4 µmol) obtained in Reference Example 19.

HRFABMS: Calcd. for $C_{48}H_{62}ClO_{10}$ [M+Na]$^+$ 797.4007. Found 797.3985.

IR (KBr) $\lambda_{max}$(cm$^{-1}$): 3471, 2962, 2929, 1713, 1456, 1377, 1338, 1243, 1195, 1172, 1119, 1074, 1038, 997

Example 28

Compound 28

In the manner similar to that of Example 14, Compound 28 (53.0 mg, 80%, for the two steps) was obtained from Intermediate 19 (70.0 mg, 80.5 µmol) obtained in Reference Example 19.

HRFABMS: Calcd. for $C_{47}H_{71}NO_{11}$ [M+Na]$^+$ 848.4925. Found 848.4913.

IR (KBr) $\lambda_{max}$(cm$^{-1}$): 3440, 2962, 2929, 1734, 1713, 1456, 1377, 1346, 1243, 1172, 1119, 1074, 1038, 993

Example 29

Compound 29

In the manner similar to that of Example 16, Compound 29 (41.0 mg, 38%, for the two steps) was obtained from Intermediate 15 (70.0 mg, 80.5 µmol) obtained in Reference Example 15.

HRFABMS: Calcd. for $C_{49}H_{67}NO_{12}$ [M+Na]$^+$ 844.4561. Found 844.4595.

IR (KBr) $\lambda_{max}$(cm$^{-1}$): 3457, 2962, 2929, 1728, 1456, 1375, 1336, 1279, 1173, 1119, 1087, 1038, 995

Example 30

Compound 30

In the manner similar to that of Example 17, Compound 30 (68.0 mg, 84%, for the two steps) was obtained from Intermediate 15 (60.0 mg, 69.0 µmol) obtained in Reference Example 15.

HRFABMS: Calcd. for $C_{49}H_{67}NO_{12}$ [M+Na]$^+$ 844.4561. Found 844.4561.

IR (KBr) $\lambda_{max}$(cm$^{-1}$): 3454, 2962, 2929, 1731, 1456, 1375, 1327, 1279, 1173, 1119, 1087, 1039, 993

Example 31

Compound 31

In the manner similar to that of Example 18, Compound 31 (58.0 mg, 93%, for the two steps) was obtained from Intermediate 15 (60.0 mg, 69.0 µmol) obtained in Reference Example 15.

HRFABMS: Calcd. for $C_{50}H_{67}NO_{14}$ [M+Na]$^+$ 928.4459. Found 928.4433.

IR (KBr) $\lambda_{max}$(cm$^{-1}$): 3444, 2962, 2931, 1726, 1531, 1456, 1375, 1348, 1270, 1173, 1119, 1087, 1039, 995

Example 32

Compound 32

Intermediate 16 (70.0 mg, 79.1 µmol) obtained in Reference Example 16 was dissolved in methylene chloride (0.8 mL). Piperidine (10 µL, 158 µmol), anhydrous 1-hydroxybenzotriazol (13.0 mg, 103 µmol) and 1-ethyl-3-(3-dimethyl-aminopropyl)carbodiimide hydrochloride (18.0 mg, 103 µmol) were added to the solution, and the mixture was stirred at room temperature for 23 hours. After purified water (0.5 mL) was added to the reaction mixture, the reaction mixture was extracted with methylene chloride (5 mL×3). The organic layer was washed with saturated brine (5 mL) and dried over anhydrous sodium sulfate. The solvent was evaporated under reduced pressure to give a crude product. Then, from the resulting crude product, Compound 32 (59.0 mg, 89%, for the two steps) was obtained in the manner similar to that of Example 8.

HRFABMS: Calcd. for $C_{48}H_{71}NO_{11}$ [M+Na]$^+$ 860.4925. Found 860.4951.

IR (KBr) $\lambda_{max}$(cm$^{-1}$): 3454, 2960, 2931, 1735, 1712, 1628, 1446, 1375, 1340, 1265, 1173, 1119, 1036, 997

Example 33

Compound 33

Intermediate 16 (70.0 mg, 79.1 µmol) obtained in Reference Example 16 was dissolved in methylene chloride (0.8 mL). Piperazine (14 mg, 158 µmol), anhydrous 1-hydroxybenzotriazol (13.0 mg, 103 µmol) and 1-ethyl-3-(3-dimethylaminopropyl)-carbodiimide hydrochloride (18.0 mg, 103 µmol) were added to the solution, and the mixture was stirred at room temperature for 23 hours. After purified water (0.5 mL) was added to the reaction mixture, the reaction mixture was extracted with methylene chloride (5 mL×3). The organic layer was washed with saturated brine (5 mL) and dried over anhydrous sodium sulfate. The solvent was evaporated under reduced pressure to give a crude product. Then, from the resulting crude product, Compound 33 (28.0 mg, 42%, for the two steps) was obtained in the manner similar to that of Example 8.

HRFABMS: Calcd. for $C_{47}H_{70}N_2O_{11}$ [M+Na]$^+$ 861.4877. Found 861.4888.

IR (KBr) $\lambda_{max}$(cm$^{-1}$): 3448, 2960, 2929, 1735, 1716, 1628, 1466, 1377, 1338, 1244, 1173, 1119, 1039, 997

Example 34

Compound 34

Compound 5 (91 mg) obtained in Example 5 was dissolved in ethanol (1.0 ml), tetrakistriphenylphosphine palladium (1.2 mg) was added to the solution, and the mixture was stirred for 10 minutes at 0° C. Then, sodium borohydride (3.8 mg) was added to the mixture, and the mixture was stirred for 5 minutes. After a saturated aqueous ammonium chloride solution was added to the reaction mixture, the reaction mixture was extracted with ethyl acetate. The organic layer was washed successively with a saturated aqueous sodium hydrogencarbonate solution and saturated brine and dried over anhydrous sodium sulfate. The solvent was evaporated under reduced pressure to give a crude product. The resulting crude product was purified by silica gel column chromatography with eluting solvents of hexane/ethyl acetate=5/1, 2/1, and 1/1 to give Compound 34 (67 mg, 82%).

$^1$H NMR (270 MHz, CDCl$_3$, partial data) δ (ppm): 5.84 (1H, m), 5.72 (3H, m), 5.53 (1H, dd, J=9.9, 2.3 Hz), 5.40 (1H, s), 5.37 (1H, m), 4.96 (1H, m), 4.74 (1H, d, J=3.3 Hz), 4.65 (2H, brs), 4.37 (2H, d, J=2.0 Hz), 4.27 (1H, m), 4.20 (2H, q, J=7.3 Hz), 3.94 (1H, d, J=6.3 Hz), 3.91 (1H, brs), 3.87 (2H, m), 3.70 (1H, m), 3.46 (1H, d, J=8.9 Hz), 3.41 (3H, s), 3.27 (1H, d, J=2.0 Hz), 2.94 (1H, t, J=9.1 Hz), 2.47 (2H, m), 2.24 (4H, m), 2.00 (1H, dd, J=12.2, 4.3 Hz), 1.85 (3H, s), 1.47 (3H, s), 1.80 (6H, m), 1.12 (3H, d, J=6.9 Hz)

$^{13}$C NMR (67.8 MHz, CDCl$_3$) δ (ppm): 173.3, 170.5, 139.5, 138.0, 137.9, 136.2, 135.1, 127.7, 124.7, 120.4, 118.3, 118.0, 95.7, 94.8, 84.7, 82.0, 80.3, 79.1, 78.7, 74.8, 70.0, 68.4, 68.3 (×2), 67.6, 67.2, 60.6, 56.4, 45.6, 40.4, 39.7, 36.5, 35.1, 34.5, 34.2, 30.5, 27.4, 20.1, 19.9, 17.9, 16.3, 15.0, 14.2, 12.9, 12.0

Example 35

Compound 35

Intermediate 20 (100 mg, 99.9 µmol) obtained in Reference Example 20 was dissolved in tetrahydrofuran (2.0 mL), a 1 mol/L aqueous potassium hydroxide solution (50 µL) was added to the solution, and the mixture was stirred at room temperature for 5 hours. The reaction mixture was neutralized with a saturated aqueous ammonium chloride solution (5 mL) and extracted with ethyl acetate (5 mL×3). The organic layer was washed with a saturated aqueous ammonium chloride solution (5 mL) and saturated brine (5 mL) and dried over anhydrous sodium sulfate. The solvent was evaporated under reduced pressure to give a crude product. Then, from the resulting crude product, Compound 35 (55.8 mg, 71%, for the two steps) was obtained from the resulting crude product in the manner similar to that of Example 8.

HRFABMS: Calcd. for $C_{43}H_{61}O_{13}$ [M+Na]$^+$ 831.3908. Found 831.3970.

IR (KBr) $\lambda_{max}$(cm$^{-1}$): 3470, 2968, 2933, 1760, 1737, 1713, 1452, 1381, 1342, 1308, 1273, 1192, 1161, 1124, 1070, 1038, 993

Example 36

Compound 36

In the manner similar to that of Example 8, Compound 36 (49.0 mg, 76%) was obtained from Intermediate 21 (80.0 mg, 83.3 µmol) obtained in Reference Example 21.

HRFABMS: Calcd. for $C_{48}H_{64}O_{12}$ [M+Na]$^+$ 795.4295. Found 795.4298.

IR (KBr) $\lambda_{max}$(cm$^{-1}$): 3450, 2966, 2933, 1733, 1716, 1456, 1381, 1340, 1309, 1272, 1193, 1161, 1124, 1066, 989

Example 37

Compound 37

In the manner similar to that of Example 8, Compound 37 (35.9 mg, 88%) was obtained from Intermediate 22 (50.2 mg, 49.1 µmol) obtained in Reference Example 22.

HRFABMS: Calcd. for $C_{43}H_{63}BrO_{11}$ [M+Na]$^+$ 857.3451. Found 857.3463.

IR (KBr) $\lambda_{max}$(cm$^{-1}$): 3465, 2964, 2931, 1737, 1718, 1456, 1377, 1340, 1309, 1273, 1184, 1161, 1122, 1072, 995

Example 38

Compound 38

In the manner similar to that of Example 8, Compound 38 (57.1 mg, 70%) was obtained from Intermediate 24 (100 mg, 99.7 µmol) obtained in Reference Example 24.

HRFABMS: Calcd. for $C_{45}H_{68}O_{18}$ [M+Na]$^+$ 839.4558. Found 839.4663.

IR (KBr) $\lambda_{max}$(cm$^{-1}$): 3473, 2962, 2931, 1759, 1736, 1716, 1456, 1379, 1340, 1306, 1275, 1244, 1198, 1173, 1120, 1066, 1086, 991

Example 39

Compound 39

In the manner similar to that of Example 35, Compound 39 (33.6 mg, 51%, for the two steps) was obtained from Intermediate 24 (83.2 mg, 82.9 µmol) obtained in Reference Example 24.

HRFABMS: Calcd. for $C_{48}H_{68}O_{18}$ [M−H]$^+$ 787.4269. Found 787.4231.

IR (KBr) $\lambda_{max}$(cm$^{-1}$): 3456, 2962, 2931, 1763, 1736, 1716, 1456, 1379, 1342, 1308, 1273, 1244, 1198, 1173, 1120, 1070, 1036, 991

Example 40

Compound 40

In the manner similar to that of Example 8, Compound 40 (46.2 mg, 75%) was obtained from Intermediate 25 (76.8 mg, 79.8 µmol) obtained in Reference Example 25.

HRFABMS: Calcd. for $C_{43}H_{66}O_{12}$ [M+Na]$^+$ 797.4452. Found 797.4448.

IR (KBr) $\lambda_{max}$(cm$^{-1}$): 3450, 2962, 2931, 1732, 1718, 1456, 1379, 1340, 1308, 1273, 1244, 1196, 1171, 1120, 1066, 1010, 989

Example 41

Compound 41

In the manner similar to that of Example 8, Compound 41 (61.7 mg, 80%) was obtained from Intermediate 26 (93.9 mg, 91.6 µmol) obtained in Reference Example 26.

HRFABMS: Calcd. for $C_{43}H_{65}BrO_{11}$ [M+Na]$^+$ 859.3698. Found 859.3686.

IR (KBr) $\lambda_{max}$(cm$^{-1}$): 3482, 2962, 2931, 1716, 1458, 1379, 1340, 1308, 1275, 1244, 1196, 1171, 1120, 1072, 1036, 989

Reference Example 1

Intermediate 1 (avermectin B1a monosaccharide)

Intermediate 1 (15.5 g, 93%) was obtained from avermectin B1a (20.0 g, 22.9 mmol) according to the method given in literature (J. Med. Chem., 23, 1134-1136 (1980)).

HRFABMS: Calcd. for $C_{41}H_{60}O_{11}$ [M+Na]$^+$ 751.4033. Found 751.4062.

IR (KBr) $\lambda_{max}$(cm$^{-1}$): 3467, 2967, 2931, 1741, 1633, 1456, 1378, 1338, 1308, 1193, 1161, 1120, 1078, 1053, 989

$^1$H NMR (270 MHz, CDCl$_3$) δ (ppm): 5.86 (m, 1H), 5.75 (m, 3H), 5.54 (dd, J=9.9, 2.7 Hz, 1H), 5.42 (s, 1H), 5.39 (m, 1H), 4.98 (m, 1H), 4.81 (d, J=3.3 Hz, 1H), 4.67 (brs, 2H), 4.29 (d, J=6.6 Hz, 1H), 4.01 (s, 1H), 3.96 (d, J=6.6 Hz, 1H), 3.95 (brs, 1H), 3.85 (m, 2H), 3.55 (ddd, J=11.5, 8.9, 4.6 Hz, 1H), 3.48 (d, J=10.3 Hz, 1H), 3.47 (s, 3H), 3.29 (q, J=2.3 Hz, 1H), 3.15 (t, J=9.2 Hz, 1H), 2.65 (brs, 1H), 2.58 (m, 1H), 2.43 (brs, 1H), 2.26 (m, 4H), 2.01 (dd, J=11.9, 3.3 Hz, 1H), 1.86 (s, 3H), 1.78 (dd, J=12.5, 2.3 Hz, 1H), 1.48 (s, 3H), 1.45 (m, 5H), 1.26 (d, J=6.3 Hz, 3H), 1.14 (d, J=6.9 Hz, 3H), 0.93 (m, 9H), 0.84 (m, 1H)

$^{13}$C NMR (67.8 MHz, CDCl$_3$) δ (ppm): 173.7, 139.6, 138.0, 137.9, 136.3, 135.1, 127.7, 124.7, 120.4, 118.3, 118.0, 95.8, 95.1, 81.8, 80.4, 79.1, 78.3, 76.1, 74.9, 68.4, 68.3 (×2), 68.1, 67.7, 56.6, 45.7, 40.5, 39.7, 36.6, 35.1, 34.2, 33.9, 30.5, 27.7, 20.2, 19.9, 17.7, 16.4, 15.1, 12.9, 12.0

Reference Example 2

Intermediate 2

Under nitrogen atmosphere, Intermediate 1 (3.50 g, 4.80 mmol) obtained in Reference Example 1 was dissolved in N,N-dimethylformamide (9.6 mL). Imidazole (0.78 g, 5.76 mmol) and tert-butyldimethylsilyl chloride (0.78 g, 11.5 mmol) were successively added to the solution, and the mixture was stirred at room temperature for 2 hours. After purified water (20 mL) was added to the reaction mixture, the reaction mixture was extracted with ethyl acetate (20 mL×3). The organic layer was washed with purified water (20 mL×3) and saturated brine (20 mL) and dried over anhydrous sodium sulfate. The solvent was evaporated under reduced pressure to give a crude product. The crude product was purified by silica gel column chromatography with eluting solvents of hexane/ethyl acetate=5/1 to give Intermediate 2 (2.50 g, 62%).

HRFABMS: Calcd. for $C_{47}H_{74}O_{11}Si$ [M+Na]$^+$ 865.4898. Found 865.4901.

IR (KBr) $\lambda_{max}$(cm$^{-1}$): 3467, 2962, 2931, 1716, 1628, 1463, 1379, 1336, 1251, 1194, 1160, 1124, 1082, 1051, 989

$^1$H NMR (270 MHz, CDCl$_3$) δ (ppm) 5.82 (m, 1H), 5.73 (m, 2H), 5.71 (dd, J=9.9, 2.6 Hz, 1H), 5.54 (dd, J=9.9, 2.3 Hz, 1H), 5.35 (m, 1H), 5.32 (m, 1H), 4.98 (m, 1H), 4.80 (d, J=3.3 Hz, 1H), 4.68 (dd, J=14.5, 2.0 Hz, 1H), 4.57 (dd, J=14.5, 2.0 Hz, 1H), 4.41 (d, J=5.6 Hz, 1H), 4.08 (brs, 1H), 3.94 (brs, 1H), 3.87 (m, 2H), 3.81 (d, J=5.6 Hz, 1H), 3.55 (ddd, J=11.5, 8.6, 4.2 Hz, 1H), 3.48 (s, 3H), 3.46 (m, 1H), 3.38 (q, J=2.2 Hz, 1H), 3.15 (t, J=9.1 Hz, 1H), 2.50 (m, 1H), 2.43 (brs, 1H), 2.26 (in, 4H), 2.03 (dd, J=12.2, 4.3 Hz, 1H), 1.78 (a, 3H), 1.78 (m, 1H), 1.49 (s, 3H), 1.46 (m, 5H), 1.26 (d, J=6.3 Hz, 3H), 1.13 (d, J=6.9 Hz, 3H), 0.92 (m, 9H), 0.91 (s, 9H), 0.87 (m, 1H), 0.12 (s, 6H)

$^{13}$C NMR (67.8 MHz, CDCl$_3$) δ (ppm): 174.0, 140.1, 137.5 (×2), 136.2, 135.1, 127.8, 124.8, 119.4, 118.3, 117.2, 95.7, 95.1, 81.9, 80.2, 80.1, 78.3, 76.1, 74.8, 69.4, 68.4, 68.3, 68.1, 67.9, 57.0, 45.8, 40.4, 39.6, 36.5, 35.1, 34.3, 33.9, 30.5, 27.5, 25.8 (×3), 20.2, 20.0, 18.4, 17.7, 16.3, 15.1, 12.9, 12.0, −4.6, −4.9

Reference Example 3

Intermediate 3 (ivermectin monosaccharide)

In the manner similar to that of Reference Example 1, Intermediate 3 (7.83 g, 93%) was obtained from ivermectin (10.0 g, 11.4 mmol).

HRFABMS: Calcd. for $C_{41}H_{62}O_{11}$ [M+Na]$^+$ 753.4190. Found 751.4186.

IR (KBr) $\lambda_{max}$(cm$^{-1}$): 3450, 2962, 2931, 1714, 1456, 1379, 1338, 1308, 1196, 1173, 1118, 1080, 1053, 989

$^1$H NMR (270 MHz, CDCl$_3$) δ (ppm): 5.87 (m, 1H), 5.72 (m, 2H), 5.43 (s, 1H), 5.9 (m, 1H), 4.98 (m, 1H), 4.82 (d, J=3.3 Hz, 1H), 4.71 (dd, J=14.2, 2.0 Hz, 1H), 4.64 (dd, J=14.2, 2.0 Hz, 1H), 4.29 (t, J=6.6 Hz, 1H), 4.09 (s, 1H), 3.97 (d, J=6.6 Hz, 1H), 3.96 (brs, 1H), 3.86 (dd, J=9.2, 6.3 Hz, 1H), 3.67 (m, 1H), 3.56 (ddd, J=11.6, 8.9, 4.3 Hz, 1H), 3.47 (s, 3H), 3.28 (q, J=2.3 Hz, 1H), 3.22 (d, J=8.3 Hz, 1H), 3.16 (t, J=9.2 Hz, 1H), 2.54 (m, 1H), 2.36 (m, 3H), 1.98 (m, 1H), 1.87 (s, 3H), 1.77 (m, 1H), 1.68-1.40 (m, 8H), 1.60 (s, 3H), 1.35 (m, 1H), 1.27 (d, J=6.3 Hz, 3H), 1.15 (d, J=6.9 Hz, 3H), 0.93 (t, J=7.3 Hz, 3H), 0.85 (d, J=6.6 Hz, 3H), 0.82 (m, 1H), 0.78 (d, J=5.2 Hz, 3H)

$^{13}$C NMR (67.8 MHz, CDCl$_3$) δ (ppm): 173.7, 139.6, 138.0, 137.9, 134.9, 124.7, 120.4, 118.3, 118.1, 97.5, 94.5, 81.6, 80.4, 79.1, 78.3, 76.6, 76.0, 68.6, 68.4, 68.1, 67.7, 67.2, 56.6, 45.7, 41.2, 39.7, 36.9, 35.7, 35.4, 34.1, 33.9, 31.2, 28.0, 27.4, 20.2, 19.9, 17.7, 17.4, 15.1, 12.4, 12.1

Reference Example 4

Intermediate 4

In the manner similar to that of Reference Example 2, Intermediate 4 (5.09 g, 74%) was obtained from Intermediate 3 (6.00 g, 8.20 mmol) obtained in Reference Example 3.

HRFABMS: Calcd. for $C_{47}H_{76}O_{11}Si$ [M+Na]$^+$ 867.5055. Found 867.5044.

IR (KBr) $\lambda_{max}$(cm$^{-1}$): 3477, 2960, 2931, 1712, 1462, 1379, 1338, 1250, 1196, 1173, 1120, 1082, 1051, 989

$^1$H NMR (270 MHz, CDCl$_3$) δ (ppm): 5.82 (m, 1H), 5.72 (m, 2H), 5.33 (brs, 1H), 5.32 (m, 1H), 4.98 (m, 1H), 4.82 (d, J=3.3 Hz, 1H), 4.68 (dd, J=14.5, 2.3 Hz, 1H), 4.57 (dd, J=14.5, 2.3 Hz, 1H), 4.43 (d, J=5.6 Hz, 1H), 4.17 (s, 1H), 3.95 (brs, 1H), 3.87 (m, 1H), 3.82 (d, J=5.6 Hz, 1H), 3.64 (m, 1H), 3.56 (ddd, J=11.5, 9.2, 4.6 Hz, 1H), 3.48 (s, 3H), 3.39 (q, J=2.3 Hz, 1H), 3.21 (m, 1H), 3.16 (t, J=9.2 Hz, 1H), 2.51 (m, 1H), 2.27 (m, 3H), 1.99 (dd, J=12.1, 4.0 Hz, 1H), 1.79 (a, 3H), 1.75 (m, 1H), 1.67-1.31 (m, 9H), 1.51 (s, 3H), 1.27 (d, J=6.3 Hz, 3H), 1.14 (d, J=6.9 Hz, 3H), 0.93 (s, 9 H), 0.93 (t, J=7.5 Hz, 3H), 0.85 (d, J=6.6 Hz, 1H), 0.78 (d, J=5.3 Hz, 3H), 0.13 (s, 6H)

$^{13}$C NMR (67.8 MHz, CDCl$_3$) δ (ppm): 174.0, 140.1, 137.5, 137.4, 134.9, 124.7, 119.4, 118.3, 117.3, 97.4, 94.9, 81.7, 80.2, 80.1, 78.3, 76.5, 76.0, 69.4, 68.7, 68.0, 67.9, 67.2, 56.5, 45.7, 41.2, 39.6, 36.8, 35.7, 35.4, 34.1, 33.9, 31.2, 28.0, 27.2, 25.8 (×3), 20.2, 20.0, 18.4, 17.7, 17.4, 15.1, 12.4, 12.1, −4.6, −4.9

Reference Example 5

Intermediate 5

Under nitrogen atmosphere, Intermediate 2 (5.00 g, 5.93 mmol) obtained in Reference Example 2 was dissolved in dimethyl sulfoxide (30 mL). Triethylamine (8.2 mL, 59.3 mmol) was added to the solution, then a solution of sulfur trioxide/pyridine complex (7.6 g, 29.6 mmol) in dimethyl sulfoxide (20 mL) was slowly added dropwise to the mixture, and the mixture was stirred at room temperature for 2 hours. After purified water (100 mL) was added to the reaction mixture, the reaction mixture was extracted with ethyl acetate (60 mL×3). The organic layer was washed successively with purified water (20 mL×3) and saturated brine (20 mL) and dried over anhydrous sodium sulfate. The solvent was evaporated under reduced pressure to give a crude product. The resulting crude product was purified by silica gel column chromatography with eluting solvents of hexane/ethyl acetate=5/1 to give Intermediate 5 (4.46 g, 89%).

HRFABMS: Calcd. for C$_{47}$H$_{72}$O$_{11}$Si [M+Na]$^+$ 863.4742. Found 863.4736.

IR (KBr) λ$_{max}$(cm$^{-1}$): 3473, 2962, 2931, 1741, 1712, 1628, 1461, 1379, 1338, 1251, 1184, 1160, 1124, 1079, 1051, 999

$^1$H NMR (270 MHz, CDCl$_3$, partial data) δ (ppm): 5.83 (m, 1H), 5.80 (m, 2H), 5.75 (dd, J=9.6, 2.0 Hz, 1H), 5.54 (dd, J=9.9, 2.3 Hz, 1H), 5.36 (m, 1H), 5.32 (d, J=1.4 Hz, 1H), 5.06 (m, 1H), 4.96 (d, J=2.0 Hz, 1H), 4.69 (dd, J=14.5, 2.0 Hz, 1H), 4.58 (dd, J=14.5, 2.0 Hz. 1H), 4.50 (q, J=6.6 Hz, 1H), 4.43 (brd, J=5.3 Hz, 1H), 4.25 (dd, J=12.0, 6.4 Hz, 1H), 4.12 (brs, 1H), 4.06 (brs, 1H), 3.87 (m, 1H), 3.82 (d, J=5.3 Hz, 1H), 3.55 (s, 3H), 3.48 (d, J=9.9 Hz, 1H), 3.39 (q, J=2.3 Hz, 1H), 2.54 (m, 1H), 2.49 (m, 1H), 2.28 (m, 3H), 2.13 (dt, J=12.0, 4.0 Hz, 1H), 2.02 (dd, J=11.6, 5.0 Hz, 1H), 1.78 (s, 3H), 1.77 (m, 1H), 1.64 (m, 2H), 1.63 (s, 3H), 1.47 (m, 2H), 1.27 (d, J=6.6 Hz, 3H), 1.16 (d, J=6.9 Hz, 3H), 0.93 (m, 10H), 0.92 (s, 9H), 0.12 (s, 6H)

$^{13}$C NMR (67.8 MHz, CDCl$_3$) δ (ppm): 205.7, 174.0, 140.6, 137.5, 136.8, 136.2, 134.8, 127.7, 125.2, 119.2, 118.7, 117.2, 95.8, 94.5, 82.3, 80.2, 80.1, 78.1, 74.8, 70.7, 69.4, 68.4, 68.2, 67.9, 58.5, 45.7, 40.4, 39.2, 39.0, 36.6, 35.1, 34.3, 30.5, 27.5, 25.8 (×3), 20.3, 20.0, 18.4, 16.4, 15.2, 13.9, 13.0, 12.0, −4.6, −4.9

Reference Example 6

Intermediate 6

In the manner similar to that of Reference Example 5, Intermediate 6 (4.11 g, 98%) was obtained from Intermediate 4 (4.21 g, 4.96 mmol) obtained in Reference Example 4.

HRFABMS: Calcd. for C$_{47}$H$_{74}$O$_{11}$Si [M+Na]$^+$ 865.4989. Found 865.4888.

IR (KBr) λ$_{max}$(cm$^{-1}$): 3473, 2960, 2931, 1740, 1713, 1461, 1379, 1336, 1250, 1182, 1120, 1078, 1053, 1012, 991

$^1$H NMR (270 MHz, CDCl$_3$, partial data) δ (ppm): 5.84 (m, 1H), 5.75 (m, 2H), 5.32 (s, 1H), 5.30 (m, 1H), 5.05 (m, 1H), 4.96 (d, J=2.3 Hz, 1H), 4.68 (dd, J=14.5, 2.0 Hz, 1H), 4.57 (dd, J=14.5, 2.0 Hz, 1H), 4.50 (q, J=6.6 Hz, 1H), 4.43 (brd, J=5.3 Hz, 1H), 4.25 (dd, J=12.0, 6.4 Hz, 1H), 4.21 (brs, 1H), 4.06 (brs, 1H), 3.82 (d, J=5.3 Hz, 1H), 3.68 (m, 1H), 3.56 (s, 3H), 3.38 (q, J=2.3 Hz, 1H), 3.21 (d, J=7.3 Hz, 1H), 2.60 (m, 1H), 2.50 (m, 1H), 2.33 (m, 2H), 2.11 (m, 1H), 1.99 (dd, J=12.4, 4.5 Hz, 1H), 1.79 (s, 3H), 1.54 (s, 3H), 1.28 (d, J=6.6 Hz, 3H), 1.17 (d, J=6.9 Hz, 3H), 0.94 (t, J=7.3 Hz, 3H), 0.92 (s, 9H), 0.85 (d, J=6.9 Hz, 3H), 0.78 (d, J=4.6 Hz, 3H), 0.13 (s, 6H)

$^{13}$C NMR (67.8 MHz, CDCl$_3$) δ (ppm): 205.7, 174.1, 140.7, 137.6, 136.8, 134.6, 125.2, 119.2, 118.7, 117.2, 97.5, 94.4, 82.3, 80.2, 80.0, 78.1, 76.7, 70.7, 69.5, 68.7, 67.9, 67.1, 58.5, 45.7, 41.2, 39.6, 39.1, 36.9, 35.7, 35.5, 34.1, 31.2, 28.1, 27.3, 25.9 (×3), 20.3, 20.0, 18.4, 17.5, 15.2, 13.9, 12.5, 12.1, −4.6, −4.9

Reference Example 7

Intermediate 7

Under nitrogen atmosphere, a 1.0 mol/L solution of lithium hexamethyldisilazane in tetrahydrofuran (2.4 mL, 2.36 mmol) was added to tetrahydrofuran (3 mL) at 0° C. Then, allyl diethylphosphonoacetate (0.50 mL, 2.36 mmol) was added to the mixture, and the mixture was stirred for 30 minutes at 0° C. Then, a solution of Intermediate 5 (1.00 g, 1.18 mmol) obtained in Reference Example 5 in tetrahydrofuran (9.0 mL) was slowly added dropwise to the mixture, and the mixture was further stirred at 0° C. for 1 hour. After purified water was added to the reaction mixture (20 mL), the reaction mixture was extracted with ethyl acetate (20 mL×3). The organic layer was washed successively with a saturated aqueous ammonium chloride solution (20 mL) and saturated brine (20 mL) and dried over anhydrous sodium sulfate. The solvent was evaporated under reduced pressure to give a crude product. The resulting crude product was purified by silica gel column chromatography with eluting solvents of hexane/ethyl acetate=10/1 to give Intermediate 7 (1.08 g, 100%).

HRFABMS: Calcd. for C$_{52}$H$_{78}$O$_{12}$Si [M+Na]$^+$ 945.5160. Found 945.5157.

IR (KBr) λ$_{max}$(cm$^{-1}$): 3500, 2962, 2931, 1724, 1655, 1459, 1377, 1336, 1250, 1186, 1159, 1124, 1084, 1035, 997

$^1$H NMR (270 MHz, CDCl$_3$, partial data) δ (ppm): 5.94 (ddt, J=17.2, 10.2, 5.6 Hz, 1H), 5.87 (s, 1H), 5.75 (dd, J=9.9, 1.7 Hz, 1H), 5.74 (m, 3H), 5.54 (dd, J=9.9, 2.3 Hz, 1H), 5.34 (dd, J=17.2, 1.3 Hz, 1H), 5.33 (m, 1H), 5.31 (s, 1H), 5.26 (dd, J=10.2, 1.3 Hz, 1H), 5.16 (t, J=3.1 Hz, 1H), 5.03 (m, 1H), 4.90 (t, J=6.3 Hz, 1H), 4.67 (dd, J=14.2, 2.3 Hz, 1H), 4.63 (d, J=5.6 Hz, 2H), 4.52 (m, 1H), 4.42 (d, J=5.6 Hz, 1H), 4.03 (brs, 1H), 3.84 (m, 1H), 3.80 (d, J=5.6 Hz, 1H), 3.48 (d, J=9.6 Hz, 1H), 3.36 (s, 3H), 1.78 (s, 3H), 1.48 (s, 3H), 1.39 (d, J=6.6 Hz, 3H), 1.10 (d, J=6.9 Hz, 3H), 0.92 (s, 9H), 0.12 (s, 6H)

$^{13}$C NMR (67.8 MHz, CDCl$_3$) δ (ppm): 173.9, 165.4, 157.4, 140.1, 137.8, 137.4, 136.2, 135.3, 132.0, 127.8, 124.6, 119.4, 118.5, 117.9, 117.3, 116.5, 95.7, 93.5, 81.3, 80.1 (×2), 74.7, 70.0, 69.5, 68.4, 68.3, 67.9, 67.1, 65.0, 56.5, 45.7, 40.5, 39.6, 36.4, 35.1, 34.3, 32.8, 30.5, 27.5, 25.8 (×3), 20.0, 19.5, 19.3, 18.4, 16.4, 14.9, 13.0, 12.0, −4.6, −4.9

Reference Example 8

Intermediate 8

Under nitrogen atmosphere, a 1.0 mol/L solution of lithium hexamethyldisilazane (9.5 mL, 9.50 mmol) in tetrahydrofuran was added to tetrahydrofuran (12 mL) at 0° C. Then, triethylphosphonoacetic acid (1.8 mL, 9.50 mmol) was added to the mixture, and the mixture was stirred for 30 minutes at 0° C. Then, a solution of Intermediate 5 (4.00 g, 4.75 mmol) obtained in Reference Example 5 in tetrahydrofuran (30 mL) was slowly added dropwise to the mixture, and the mixture was further stirred at 0° C. for 1 hour. After purified water (50 mL) was added to the reaction mixture, the reaction mixture was extracted with ethyl acetate (50 mL×3). The organic layer was washed successively with a saturated aqueous ammonium chloride solution (50 mL) and saturated brine (50 mL) and dried over anhydrous sodium sulfate. The solvent was evaporated under reduced pressure to give a crude product. The resulting crude product was purified by silica gel column chromatography with eluting solvents of hexane/ethyl acetate=15/1 to give Intermediate 8 (3.82 g, 86%).

HRFABMS: Calcd. for $C_{51}H_{78}O_{12}Si$ [M+Na]$^+$ 933.6160. Found 933.5152.

IR (KBr) $\lambda_{max}$(cm$^{-1}$): 3482, 2962, 2931, 1720, 1655, 1462, 1379, 1340, 1250, 1186, 1159, 1126, 1083, 1033, 997

Reference Example 9

Intermediate 9

Under nitrogen atmosphere, Intermediate 8 (2.80 g, 3.07 mmol) obtained in Reference Example 8 was dissolved in methylene chloride (30 mL). To this solution, a 0.95 mol/L solution of diisobutylaluminum hydride in n-hexane (15 mL, 15.3 mmol) was added dropwise at −78° C., and the mixture was stirred at −78° C. for 1 hour. The reaction mixture was diluted with methylene chloride (100 mL), and then methanol was added to the reaction mixture to terminate the reaction. Furthermore, sodium sulfate decahydrate (20 g) and Cerite® (20 g) were added to the reaction mixture, and the reaction mixture was stirred vigorously. After 1 hour, the reaction mixture was filtered, and the solvent was evaporated under reduced pressure to give a crude product. The resulting crude product was purified by silica gel column chromatography with eluting solvents of hexane/ethyl acetate=3/1 to give Intermediate 9 (1.83 g, 69%).

HRFABMS: Calcd. for $C_{49}H_{76}O_{11}Si$ [M+Na]$^+$ 891.5055. Found 891.5037.

IR (KBr) $\lambda_{max}$(cm$^{-1}$): 3448, 2966, 2933, 1720, 1655, 1460, 1379, 1340, 1244, 1186, 1159, 1116, 1082, 1034, 989

Reference Example 10

Intermediate 10

Sodium borohydride (36.0 mg, 967 μmol) was added to a solution of Intermediate 7 (596 mg, 645 μmol) obtained in Reference Example 7 in ethanol (6.5 mL) containing tetrakistriphenylphosphine palladium (1 mg, 6.45 μmol), and the mixture was stirred for 2 hours. After a saturated aqueous ammonium chloride solution (5 mL) was added to the reaction mixture, the reaction mixture was extracted with ethyl acetate (10 mL×3). The organic layer was washed with saturated brine (10 mL) and dried over anhydrous sodium sulfate. The solvent was evaporated under reduced pressure to give a crude product. The resulting crude product was purified by silica gel column chromatography with eluting solvents of hexane/ethyl acetate=5/1 to give Intermediate 10 (567 mg, 100%).

HRFABMS: Calcd. for $C_{49}H_{74}O_{12}Si$ [M+Na]$^+$ 905.4817. Found 905.4892.

IR (KBr) $\lambda_{max}$(cm$^{-1}$): 3448, 2962, 2931, 1716, 1460, 1379, 1342, 1251, 1186, 1161, 1124, 1084, 1038, 999

Reference Example 11

Intermediate 11

In the manner similar to that of Reference Example 7, Intermediate 11 (1.27 g, 97%) was obtained from Intermediate 6 (1.20 g, 1.42 mmol) obtained in Reference Example 6.

HRFABMS: Calcd. for $C_{42}H_{80}O_{12}Si$ [M+Na]$^+$ 947.5317. Found 947.5336.

IR (KBr) $\lambda_{max}$(cm$^{-1}$): 3473, 2960, 2931, 1724, 1649, 1460, 1379, 1338, 1248, 1197, 1163, 1120, 1088, 1037, 1012, 991

Reference Example 12

Intermediate 12

In the manner similar to that of Reference Example 8, Intermediate 12 (1.60 g, 70%) was obtained from Intermediate 6 (2.10 g, 2.49 mmol) obtained in Reference Example 6.

HRFABMS: Calcd. for $C_{51}H_{80}O_{12}Si$ [M+Na]$^+$ 936.6317. Found 935.5298.

IR (KBr) $\lambda_{max}$(cm$^{-1}$): 3448, 2960, 2931, 1720, 1462, 1379, 1338, 1248, 1198, 1163, 1120, 1090, 1036, 991

Reference Example 13

Intermediate 13

Under nitrogen atmosphere, a 1.0 mol/L solution of lithium hexamethyldisilazane in tetrahydrofuran (523 μL, 523 μmol) was added to tetrahydrofuran (1 mL) at 0° C. Then, diethylphosphonocyanomethyl (84 μL, 523 μmol) was added to the mixture, and the mixture was stirred for 30 minutes at 0° C. A solution of Intermediate 6 (210 mg, 249 μmol) obtained in Reference Example 6 in tetrahydrofuran (1.4 mL) was slowly added dropwise to the reaction mixture, and the reaction mixture was further stirred at 0° C. for 1 hour. After purified water (5 mL) was added to the reaction mixture, the reaction mixture was extracted with ethyl acetate (5 mL×3). The organic layer was washed successively with a saturated aqueous ammonium chloride solution (10 mL) and saturated brine (10 mL) and dried over anhydrous sodium sulfate. The solvent was evaporated under reduced pressure to give a crude product. The resulting crude product was purified by silica get column chromatography with eluting solvents of hexane/ethyl acetate=15/1 to give Intermediate 13 (206 mg, 96%).

Reference Example 14

Intermediate 14

Intermediate 9 (100 mg, 112 μmol) obtained in Reference Example 9 was dissolved in methylene chloride (1.1 mL). Diisopropylethylamine (77 μL, 448 μmol), 4-dimethylaminopyridine (20 mg, 168 μmol) and p-toluenesulfonyl chloride (85 mg, 448 μmol) were successively added to the solution, and the mixture was stirred at room temperature for 16 hours. After a saturated aqueous ammonium chloride solution (2 mL) was added to the reaction mixture, the reaction mixture was extracted with methylene chloride (5 mL×3). The organic layer was washed with saturated brine (5 mL) and dried over anhydrous sodium sulfate. The solvent was evaporated under reduced pressure to give a crude product. The resulting crude product was purified by silica gel column chromatography with eluting solvents of hexane/ethyl acetate=5/1 to give Intermediate 14 (97.8 mg, 96%).

HRFABMS: Calcd. for $C_{49}H_{76}ClO_{10}$ [M+Na]$^+$ 909.4716. Found 909.4748.

IR (KBr) $\lambda_{max}$(cm$^{-1}$): 3480, 2962, 2931, 1733, 1462, 1379, 1338, 1265, 1186, 1161, 1122, 1084, 1038, 997

Reference Example 15

Intermediate 15

In the manner similar to that of Reference Example 9, Intermediate 15 (862 mg, 65%) was obtained from Intermediate 12 (1.40 g, 1.35 mmol) obtained in Reference Example 12.

HRFABMS: Calcd. for $C_{49}H_{78}O_{11}Si$ [M+Na]$^+$ 893.5211. Found 893.5220.

IR (KBr) $\lambda_{max}$(cm$^{-1}$): 3477, 2960, 2931, 1735, 1712, 1678, 1458, 1379, 1338, 1252, 1196, 1174, 1119, 1086, 1038, 993

Reference Example 16

Intermediate 16

In the manner similar to that of Reference Example 10, Intermediate 16 (760 mg, 86%) was obtained from Intermediate 11 (924 mg, 999 μmol) obtained in Reference Example 11.

HRFABMS: Calcd. for $C_{49}H_{76}O_{12}Si$ [M+Na]$^+$ 907.5004. Found 907.5019.

IR (KBr) $\lambda_{max}$(cm$^{-1}$): 3464, 2960, 2931, 1714, 1460, 1377, 1340, 1250, 1184, 1172, 1120, 1088, 1036, 993

Reference Example 17

Intermediate 17

Under nitrogen atmosphere, Intermediate 2 (820 mg, 972 μmol) obtained in Reference Example 2 was dissolved in N,N-dimethylformamide (9 mL). Imidazole (463 mg, 6.80 mmol) and trimethylsilyl chloride (0.42 mL, 3.40 mmol) were successively added to the solution, and the mixture was stirred at room temperature for 20 hours. After purified water (50 mL) was added to the reaction mixture, the reaction mixture was extracted with ethyl acetate (50 mL×3). The organic layer was washed successively with purified water (100 mL×3) and saturated brine (50 mL) and dried over anhydrous sodium sulfate. The solvent was evaporated under reduced pressure to give a crude product. The crude product was purified by silica gel column chromatography with eluting solvents of hexane/ethyl acetate=5/1 to give Intermediate 17 (1.01 g, 100%).

HRFABMS: Calcd. for $C_{58}H_{90}O_{11}Si_3$ [M+Na]$^+$ 1009.5689. Found 1009.5690.

IR (KBr) $\lambda_{max}$(cm$^{-1}$): 2960, 2933, 1745, 1462, 1385, 1336, 1311, 1252, 1205, 1161, 1128, 1105, 1086, 991

Reference Example 18

Intermediate 18

Intermediate 17 (940 mg, 951 μmol) obtained in Reference Example 17 was dissolved in tetrahydrofuran (25 mL). A mixture of acetic acid (5 mL) and purified water (5 mL) was added to the solution, and the mixture was stirred at room temperature for 10 hours. The reaction mixture was poured into a saturated aqueous sodium hydrogencarbonate solution (100 mL), and then the mixture was extracted with ethyl acetate (50 mL×3). The organic layer was washed with saturated brine (50 mL) and dried over anhydrous sodium sulfate. The solvent was evaporated under reduced pressure to give a crude product. The crude product was purified by silica gel column chromatography with eluting solvents of hexane/ethyl acetate=5/1 to give Intermediate 18 (831 mg, 96%).

HRFABMS: Calcd. for $C_{50}H_{82}O_{11}Si_2$ [M+Na]$^+$ 937.5293. Found 937.5276.

IR (KBr) $\lambda_{max}$(cm$^{-1}$): 3450, 2960, 2933, 1743, 1458, 1381, 1336, 1251, 1160, 1130, 1086, 995

Reference Example 19

Intermediate 19

In the manner similar to that of Reference Example 14, Intermediate 19 (407 mg, 99%) was obtained from Intermediate 16 (400 mg, 459 μmol) obtained in Reference Example 15.

HRFABMS: Calcd. for $C_{49}H_{77}ClO_{10}Si$ [M+Na]$^+$ 888.4975. Found 888.5025.

IR (KBr) $\lambda_{max}$(cm$^{-1}$): 3483, 2960, 2931, 1712, 1460, 1377, 1338, 1250, 1172, 1120, 1087, 1038, 995

Reference Example 20

Intermediate 20

Under nitrogen atmosphere, Intermediate 18 (50.0 mg, 54.6 μmol) obtained in Reference Example 18 was dissolved in methylene chloride (1 mL), and rhodium acetate dimer (1 mg, 2.73 μmol) was added to the solution. To this solution, a solution of ethyl diazoacetate (12 μL, 109 μmol) in methylene chloride (1 mL) was added dropwise at room temperature. After the mixture was stirred at room temperature for 2 hours, the solvent was evaporated under reduced pressure to give a crude product. The resulting crude product was purified by silica gel column chromatography with eluting solvents of hexane/ethyl acetate=6/1 to give Intermediate 20 (20.4 mg, 87%).

HRFABMS: Calcd. for $C_{54}H_{88}O_{13}Si_2$ [M+Na]$^+$ 1023.5661. Found 1023.5696.

IR (KBr) $\lambda_{max}$(cm$^{-1}$): 3450, 2960, 2933, 1743, 1458, 1381, 1336, 1252, 1159, 1130, 1086, 997

Reference Example 21

Intermediate 21

Under nitrogen atmosphere, a 1.0 mol/L solution of super hydride in tetrahydrofuran (1.5 mL, 1.50 mmol) was added dropwise to a solution of Intermediate 20 (300 mg, 300 μmol) obtained in Reference Example 20 in tetrahydrofuran (21 mL) at −78° C., and the mixture was stirred for 30 minutes. After a 30% aqueous hydrogen peroxide solution (200 μL) was added to the mixture, the mixture was stirred at −78° C. for 30 minutes. Sodium sulfite (100 mg) was added to the reaction mixture, and the reaction mixture was extracted with ethyl acetate (10 mL×3). The organic layer was washed with saturated brine (10 mL) and dried over anhydrous sodium sulfate. The solvent was evaporated under reduced pressure to give a crude product. The crude product was purified by silica gel column chromatography (15 g) with eluting solvents of hexane/ethyl acetate=3/1 to give Intermediate 21 (90.7 mg, 32%).

HRFABMS: Calcd. for $C_{52}H_{86}O_{12}Si_2$ $[M+Na]^+$ 981.5556. Found 981.5597.

IR (KBr) $\lambda_{max}(cm^{-1})$: 3476, 2960, 2933, 1743, 1462, 1385, 1336, 1309, 1262, 1205, 1161, 1128, 1085, 989

Reference Example 22

Intermediate 22

Under nitrogen atmosphere, Intermediate 21 (84.5 mg, 82.7 μmol) obtained in Reference Example 21 was dissolved in methylene chloride (1.7 mL). Triphenylphosphine (54.2 mg, 0.207 mmol) and imidazole (68.5 mg, 0.207 mmol) were added to the solution, and the mixture was stirred at room temperature for 3 hours. A saturated ammonium chloride solution (3 mL) was added to the reaction mixture, and the reaction mixture was extracted with methylene chloride (10 mL×3). The organic layer was washed with saturated brine (10 mL) and dried over anhydrous sodium sulfate. The solvent was evaporated under reduced pressure to give a crude product. The resulting crude product was purified by silica gel column chromatography (15 g) with eluting solvents of hexane/ethyl acetate=5/1 to give Intermediate 22 (50.2 mg, 59%).

HRFABMS: Calcd. for $C_{52}H_{85}BrO_{11}Si_2$ $[M+Na]^+$ 1043.4712. Found 1043.4658.

IR (KBr) $\lambda_{max}(cm^{-1})$: 3465, 2960, 2933, 1743, 1462, 1381, 1336, 1309, 1252, 1205, 1161, 1128, 1095, 993

Reference Example 23

Intermediate 23

Under nitrogen atmosphere, Intermediate 4 (2.12 g, 2.51 mmol) obtained in Reference Example 4 was dissolved in N,N-dimethylformamide (25 mL). Imidazole (1.19 g, 17.5 mmol) and trimethylsilyl chloride (1.1 mL, 8.78 mmol) were successively added to the solution, and the mixture was stirred at room temperature for 20 hours. After purified water (200 mL) was added to the reaction mixture, the reaction mixture was extracted with ethyl acetate (100 mL×3). The organic layer was washed successively with purified water (200 mL×3) and saturated brine (100 mL) and dried over anhydrous sodium sulfate. The solvent was evaporated under reduced pressure to give a crude product. Then, from the resulting crude product, Intermediate 23 (1.89 g, 82%, for the two steps) was obtained in the manner similar to that of Reference Example 18.

HRFABMS: Calcd. for $C_{50}H_{84}O_{11}Si_2$ $[M+Na]^+$ 939.5450. Found 939.5452.

IR (KBr) $\lambda_{max}(cm^{-1})$: 3489, 2960, 2933, 1743, 1462, 1389, 1336, 1309, 1252, 1203, 1168, 1120, 1084, 1051, 1009, 989

Reference Example 24

Intermediate 24

In the manner similar to that of Reference Example 20, Intermediate 24 (443 mg, 21%) was obtained from Intermediate 23 (1.89 g, 2.07 mmol) obtained in Reference Example 23.

HRFABMS: Calcd. for $C_{54}H_{90}O_{13}Si_2$ $[M+Na]^+$ 1025.5818. Found 1025.5837.

IR (KBr) $\lambda_{max}(cm^{-1})$: 3455, 2960, 2931, 1759, 1741, 1462, 1379, 1336, 1308, 1252, 1203, 1169, 1132, 1088, 1035, 991

Reference Example 25

Intermediate 25

In the manner similar to that of Reference Example 21, Intermediate 25 (271 mg, 87%) was obtained from Intermediate 24 (326 mg, 324 μmol) obtained in Reference Example 24.

HRFABMS: Calcd. for $C_{52}H_{88}O_{12}Si_2$ $[M+Na]^+$ 983.5712. Found 983.5719.

IR (KBr) $\lambda_{max}(cm^{-1})$: 3456, 2958, 2931, 1743, 1458, 1380, 1336, 1309, 1251, 1205, 1169, 1128, 1088, 1010, 989

Reference Example 26

Intermediate 26

In the manner similar to that of Reference Example 22, Intermediate 26 (94.3 mg, 74%) was obtained from Intermediate 25 (76.8 mg, 79.8 μmol) obtained in Reference Example 25.

HRFABMS: Calcd. for $C_{52}H_{87}BrO_{11}Si_2$ $[M+Na]^+$ 1045.4868. Found 1045.4890.

IR (KBr) $\lambda_{max}(cm^{-1})$: 3488, 2960, 2931, 1743, 1462, 1379, 1336, 1309, 1252, 1205, 1169, 1128, 1088, 1009, 989

The intermediates obtained in the above reference examples and the starting materials are shown in Table 6.

TABLE 6

| Intermediate No. | $Z^A$ | 4' | $R^{2A}$ | $R^{7A}$ |
|---|---|---|---|---|
| Avermectin B1a | —O—[sugar with OCH₃, OH, CH₃] | OCH₃ | Single bond | OH | OH |
| 1 | OH | | Single bond | OH | OH |
| 2 | OH | | Single bond | OTBDMS | OH |
| 5 | O | | Double bond | OTBDMS | OH |

TABLE 6-continued

| | | | | |
|---|---|---|---|---|
| 7 | CHCO$_2$CH$_2$CH=CH$_2$ | Double bond | OTBDMS | OH |
| 8 | CHCO$_2$CH$_2$CH$_3$ | Double bond | OTBDMS | OH |
| 9 | CHCH$_2$OH | Double bond | OTBDMS | OH |
| 10 | CHCO$_2$H | Double bond | OTBDMS | OH |
| 14 | CHCH$_2$Cl | Double bond | OTBDMS | OH |
| 17 | OSi(CH$_3$)$_3$ | Single bond | OTBDMS | OSi(CH$_3$)$_3$ |
| 18 | OH | Single bond | OTBDMS | OSi(CH$_3$)$_3$ |
| 20 | OCH$_2$CO$_2$CH$_2$CH$_3$ | Single bond | OTBDMS | OSi(CH$_3$)$_3$ |
| 21 | OCH$_2$CH$_2$OH | Single bond | OTBDMS | OSi(CH$_3$)$_3$ |
| 22 | OCH$_2$CH$_2$Br | Single bond | OTBDMS | OSi(CH$_3$)$_3$ |

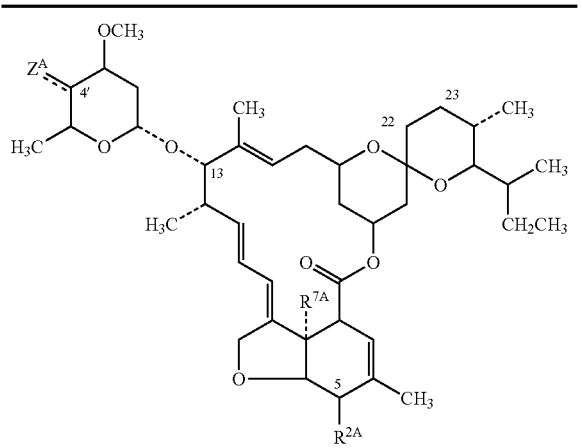

| Intermediate No. | $Z^A$ | 4' | $R^{2A}$ | $R^{7A}$ |
|---|---|---|---|---|
| Ivermectin | (sugar group with OCH$_3$) | Single bond | OH | OH |
| 3 | OH | Single bond | OH | OH |
| 4 | OH | Single bond | OTBDMS | OH |
| 6 | O | Double bond | OTBDMS | OH |
| 11 | CHCO$_2$CH$_2$CH=CH$_2$ | Double bond | OTBDMS | OH |
| 12 | CHCO$_2$CH$_2$CH$_3$ | Double bond | OTBDMS | OH |
| 13 | CHCN | Double bond | OTBDMS | OH |
| 15 | CHCH$_2$OH | Double bond | OTBDMS | OH |
| 16 | CHCO$_2$H | Double bond | OTBDMS | OH |
| 19 | CHCH$_2$Cl | Single bond | OTBDMS | OH |
| 23 | OH | Single bond | OTBDMS | OSi(CH$_3$)$_3$ |
| 24 | OCH$_2$CO$_2$CH$_2$CH$_3$ | Single bond | OTBDMS | OSi(CH$_3$)$_3$ |
| 25 | OCH$_2$CH$_2$OH | Single bond | OTBDMS | OSi(CH$_3$)$_3$ |
| 26 | OCH$_2$CH$_2$Br | Single bond | OTBDMS | OSi(CH$_3$)$_3$ |

* OTBDMS: O-tert-Butyldimethylsilyl

Test Example 1

Methods for determining antiparasitic effects of the compounds disclosed according to the present invention are explained below.

As model insects for simple determination of antiparasitic and insecticidal activities, those insects are desired which can be easily obtained and bred in laboratories, and have no pathogenicity to a human. *Caenorhabditis elegans*, an unparasitic eelworm widely used in experiments of genetics, was used as a typical steam worm, and *artemia salina* used as feed for tropical fish and named Brine shrimp, was used instead of insects.

Preparation of *Caenorhabditis elegans* Used for Evaluation

*Escherichia coli* for the feed of *caenorhabditis elegans* (mutant having uracil requirement) was inoculated in a seed medium for *E. coli* to which a small amount of uracil was added, and cultured with shaking at 27° C. for 1 day. A petri dish of 6 cm diameter was filled with 10 mL of an agar medium for eelworm proliferation, and the medium was solidified. Then 0.5 mL of the culture of *E. coli* was spread over the medium in the dish, and the dish was incubated at 37° C. to proliferate *E. coli*. A piece of the agar was collected with a platinum loop from a petri dish in which *caenorhabditis elegans* successfully proliferated, and inoculated in petri dishes in which *E. coli* was proliferated. The petri dishes were incubated at 20° C. to proliferate *caenorhabditis elegans*. Since the life of eelworm is about 2 weeks, subculture was carried out every once a week. The eelworms grown with spread on the surface of the petri dish after 3 to 5 days from subculture were used for the experiments.

<Preparation of *Artemia salina* Used for Evaluation>

To a buffer for *artemia salina* (obtained by dissolving 0.24% of Tris, 2.57% of sodium chloride, 0.47% of magnesium chloride, 0.07% of potassium chloride, 0.02% of sodium carbonate, 0.64% of magnesium sulfate and 0.11% of calcium chloride in distilled water and adjusting the pH to 7.1 with hydrochloric acid), dried eggs of *artemia salina* [Tetra Brine Shrimp Eggs, Warner Lambert Co.] were added. The noprius larvae 1 or 2 days after hatching were used for the experiments.

<Preparation of Agar Medium for Eelworm Proliferation>

Solution A was obtained by dissolving 0.3% of sodium chloride, 1.7% of bact-agar (DIFCO Co.), 0.5% of bact-peptone (DIFCO Co.) and 1.0% of yeast extract (DIFCO Co.) in distilled water.

Solution B was obtained by dissolving 0.5% of cholesterol in ethanol.

Solution C was obtained by dissolving 13.9% of calcium chloride in distilled water.

Solution D was obtained by dissolving 30.8% of magnesium sulfate heptahydrate in distilled water.

Solution E was obtained by dissolving 13.54% of KH$_2$PO$_4$ and 4.45% of K$_2$HPO$_4$ in distilled water.

The aforementioned Solutions A, C and D were sterilized in an autoclave at 121° C. for 20 minutes, and each solution was stored at 4° C.

The agar medium for eelworm proliferation was prepared by mixing the solutions in the following proportion: Solution A: 100 mL, Solution B: 0.1 mL, Solution C: 0.05 mL, Solution D: 0.1 mL and Solution E: 2.5 mL (without pH adjustment), and dispensing each 10 mL portion into petri dishes of 60×15 mm.

<Preparation of *E. coli* Seed Medium>

In distilled water, 2.0% of bact-trypton (DIFCO Co.), 0.55% of sodium chloride and 0.001% of uracil (SIGMA Co., pH 7.4) were dissolved, and the solution was sterilized in an autoclave at 121° C. for 20 minutes.

<Experimental Procedure>

Each well of a 96 well microplate was filled with the solution of the test compound (methanol as a solvent), and the solvent was removed using a vacuum pump, then 250 μl of the assay medium was added to each wells (the assay medium was prepared by dissolving 7.5 mM sodium hydrogencarbonate, 7.5 mM potassium chloride, 7.5 mM calcium chloride dihydrate and 7.5 mM magnesium sulfate heptahydrate in distilled water and adding 0.01% of lecithin to the solution), and then the microplate was shaken using a microplate mixer for 15 minutes. To each well, a few individuals of *caenorhabditis elegans* were added by softly rubbing the surface of the agar using a toothpick, or a few individuals of *artemia salina* were added together with 50 μl of the buffer. The microplate was incubated at 20° C., and then the insects were observed after 24 and 48 hours under a microscope (magnification of 40×). The results were compared to those obtained without addition of the test compound, and evaluated by 4 grades.

The evaluation results were shown by indications of 4 grades from 0 to 3.

3: No movement
2: Between 1 and 3
1: A little week movements
0: Active movements Of the 4 grades, Indications 3 and 2 were judged as effective, and Indications 1 and 0 as ineffective. The results are shown in Table 7. In Table 7, the values for each compound are minimum inhibitory concentrations (MIC) which were required to give Indication 2 (or 3) for *caenorhabditis elegans* or *artemia salina*. In Table 7, *caenorhabditis elegans* and *artemia salina* are abbreviated as C.E. and A.S., respectively.

TABLE 7

| Compound No. | C.E. (ng/mL) | A.S. (ng/mL) |
|---|---|---|
| Avermectin B1a | 2 | 0.5 |
| Ivermectin | 2 | 2 |
| Avermectin B1a monosaccharide | 2 | 2 |
| Ivermectin monosaccharide | 2 | 2 |
| 6 | 2 | 2 |
| 22 | 2 | 2 |
| 28 | 2 | 2 |
| 34 | 2 | 0.5 |
| 35 | 1 | 2 |
| 36 | 2 | 2 |
| 38 | 2 | 0.5 |
| 41 | 2 | 0.5 |

INDUSTRIAL APPLICABILITY

According to the present invention, avermectin derivatives having antiparasitic activity and salts thereof are provided. The aforementioned derivatives and salts thereof are useful as active ingredients of antiparasitic agents.

What is claimed is:
1. A compound represented by the general formula (I) or a salt thereof:

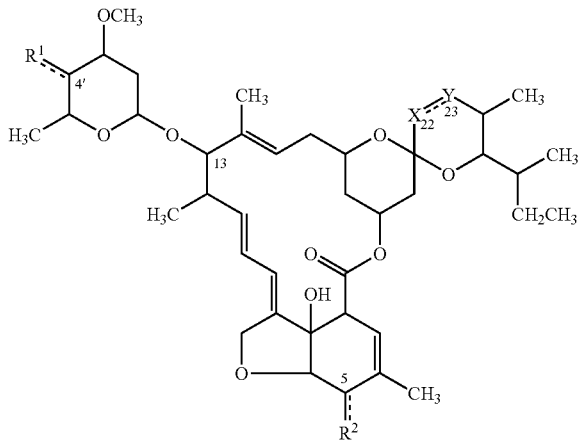

wherein,

—X═Y— represents —CH═CH—, —CH$_2$C(═O)—, —CH$_2$—CH$_2$—, or —CH$_2$—CH(R$^{13}$)— (wherein R$^{13}$ represents a hydroxyl group or a lower alkylcarbonyloxy group,

- - - - - between R$^1$ and the carbon atom at 4'-position represents a single bond or a double bond,

- - - - - between R$^2$ and the carbon atom at 5-position represents a single bond or a double bond, and
1) when

—X═Y— represents —CH═CH— or —CH$_2$—CH$_2$—, and

- - - - - between R$^1$ and the carbon atom at 4'-position represents a double bond,
R$^1$ represents ═C(R$^{11}$)(R$^{12}$) <wherein R$^{11}$ represents a substituted or unsubstituted lower alkyl group, a formyl group, a lower alkoxycarbonyl group (wherein a lower alkyl moiety of said lower alkoxycarbonyl group may be substituted with a 5- or 6-membered aromatic or aliphatic heterocyclic group), —CH=N—OR³ (wherein R³ represents a hydrogen atom or a lower alkyl group), a lower alkenylcarbonyl group, —CH=N—NH—CONH₂, a cyano group, —COR⁴ {wherein R⁴ represents a hydroxyl group, a lower alkenyloxy group, or —N(R⁵)(R⁶) (wherein R⁵ and R⁶ are combined together with the adjacent nitrogen atom to form a nitrogen-containing 5- or 6-membered aromatic or aliphatic heterocyclic group)}, a vinyl group substituted with a lower alkenyloxycarbonyl group, —CO—S—CH²—CH₂—NH—CO—R^X (wherein R^X represents a lower alkyl group), or —CH=CH—COOH, and R¹² represents a hydrogen atom, provided that when R¹¹ represents a cyano group, R¹² represents a hydrogen atom or a lower alkyl group>, or is combined together with the carbon atom at 4'-position to form a carbonyl group, and when

----- between R² and the carbon atom at 5-position represents a single bond, R² represents a hydroxyl group, a lower alkoxyl group, or a lower alkenyloxycarbonyloxy group, and
when

----- between R² and the carbon atom at 5-position represents a double bond, R² is combined together with the carbon atom at 5-position to form a carbonyl group or a hydroxime group (—C(=NOH)—);

2) when

—X≡Y— represents —CH=CH— or —CH₂—CH₂—, and

----- between R¹ and the carbon atom at 4'-position represents a single bond,
R¹ represents a hydroxyl group, —OCH(R¹ᵃ)(R¹ᵇ) <wherein R¹ᵃ represents a substituted lower alkyl group, a formyl group, a carboxyl group, a lower alkoxycarbonyl group (wherein a lower alkyl moiety of said lower alkoxycarbonyl group may be substituted with a 5- or 6-membered aromatic or aliphatic heterocyclic group), —CH=N—OR⁷ (wherein R⁷ represents a hydrogen atom or a lower alkyl group), a lower alkenyloxycarbonyl group, —CH=N—NH—CONH₂, a cyano group, —COR⁸ {wherein R⁸ represents an arylalkyloxy group (wherein the aryl group may contain one or more heteroatoms as ring-constituting atoms) or —N(R⁹)(R¹⁰) (wherein R⁹ and R¹⁰ are combined together with the adjacent nitrogen atom to form a nitrogen-containing 5- or 6-membered aromatic or aliphatic heterocyclic group)}, a vinyl group substituted with a lower alkenyloxycarbonyl group, —CO—S—CH₂—CH₂—NH—CO—R^Y (wherein R^Y represents a lower alkyl group), —CH=CH—COOH, or a substituted or unsubstituted aryl group, and R¹ᵇ represents a hydrogen atom, provided that when R¹ᵃ represents a carboxyl group or a lower alkoxycarbonyl group (wherein a lower alkyl moiety of said lower alkoxycarbonyl group may be substituted with a 5- or 6-membered aromatic or aliphatic heterocyclic group), R¹ᵇ may further represents a lower alkoxycarbonyl group (wherein a lower alkyl moiety of said lower alkoxycarbonyl group may be substituted with a 5- or 6-membered aromatic or aliphatic heterocyclic group), a carboxyl group, a cyano group, or an aryl group>, a carboxymethyl group, or a cyanomethyl group, and when

----- between R² and the carbon atom at 5-position represents a single bond, R² represents a hydroxyl group, a lower alkoxyl group, or a lower alkenyloxycarbonyloxy group, and
when

----- between R² and the carbon atom at 5-position represents a double bond, R² is combined together with the carbon atom at 5-position to form a carbonyl group or a hydroxime group (—C(=NOH)—);

3) when

—X≡Y— represents —CH₂—C(=O)—, and

----- between R¹ and the carbon atom at 4'-position represents a double bond,
R¹ represents =C(R¹¹ᵃ)(R¹²ᵃ) {wherein R¹¹ᵃ represents a lower alkoxycarbonyl group (wherein a lower alkyl moiety of said lower alkoxycarbonyl group may be substituted with a 5- or 6-membered aromatic or aliphatic heterocyclic group) or —COOCH₂CH=CH₂, and R¹²ᵃ represents a hydrogen atom}, or is combined together with the carbon atom at 4'-position to form carbonyl group,

----- between R² and the carbon atom at 5-position represents a single bond, and R² represents a hydroxyl group, a lower alkoxyl group, or a lower alkenyloxycarbonyloxy group;

4) when

—X═Y— represents —$CH_2$—C(═O)—, and

----- between $R^1$ and the carbon atom at 4'-position represents a single bond, $R^1$ represents —OCH($R^{1aa}$)($R^{1ba}$) <wherein $R^{1aa}$ represents a substituted lower alkyl group, a formyl group, a carboxyl group, a lower alkoxycarbonyl group (wherein a lower alkyl moiety of said lower alkoxycarbonyl group may be substituted with a 5- or 6-membered aromatic or aliphatic heterocyclic group), —CH═N—$OR^{7a}$ (wherein $R^{7a}$ represents a hydrogen atom or a lower alkyl group), a lower alkenyloxycarbonyl group, —CH═N—NH—$CONH_2$, a cyano group, —$COR^{8a}$ {wherein $R^{8a}$ represents an arylalkyloxy group (wherein the aryl group may contain one or more heteroatoms as ring-constituting atoms), or —N($R^{9a}$)($R^{10a}$) (wherein $R^{9a}$ and $R^{10a}$ are combined together with the adjacent nitrogen atom to form a nitrogen-containing 5- or 6-membered aromatic or aliphatic heterocyclic group)}, a vinyl group substituted with a lower alkenyloxycarbonyl group, —CO—S—$CH^2$—$CH_2$—NH—CO—$R^{Ya}$ (wherein $R^{Ya}$ represents a lower alkyl group), —CH═CH—COOH, or a substituted or unsubstituted aryl group, and $R^{1ba}$ represents a hydrogen atom, provided that when $R^{1aa}$ represents a carboxyl group or a lower alkoxycarbonyl group (wherein a lower alkyl moiety of said lower alkoxycarbonyl group may be substituted with a 5- or 6-membered aromatic or aliphatic heterocyclic group), $R^{1ba}$ may further represent a lower alkoxycarbonyl group (wherein a lower alkyl moiety of said lower alkoxycarbonyl group may be substituted with a 5- or 6-membered aromatic or aliphatic heterocyclic group), a carboxyl group, a cyano group, or an aryl group>, and when

----- between $R^2$ and the carbon atom at 5-position represents a single bond, $R^2$ represents a hydroxyl group, a lower alkoxyl group, or a lower alkenyloxycarbonyloxy group, and when

----- between $R^2$ and the carbon atom at 5-position represents a double bond, $R^2$ is combined together with the carbon atom at 5-position to form a carbonyl group or a hydroxime group (—C(═NOH)—);

5) when

—X═Y— represents —$CH_2$—CH($R^{13}$)— (wherein $R^{13}$ has the same meaning as that defined above), and

----- between $R^1$ and the carbon atom at 4'-position represents a double bond, $R^1$ represents ═C($R^{11b}$)($R^{12b}$) (wherein $R^{11b}$ represents a cyano group, a carboxyl group, a lower alkoxycarbonyl group, or a lower alkenyloxycarbonyl group, or is combined together with the carbon atom at 4'-position to form a carbonyl group, and $R^{12b}$ represents a hydrogen atom),

----- between $R^2$ and the carbon atom at 5-position represents a single bond, and $R^2$ represents a hydroxyl group, a lower alkoxyl group, or a lower alkenyloxycarbonyloxy group; and 6) when

—X═Y— represents —$CH_2$—CH($R^{13}$)— (wherein $R^{13}$ has the same meaning as that defined above), and

----- between $R^1$ and the carbon atom at 4'-position represents a single bond, $R^1$ represents —OCH($R^{1ab}$)($R^{1bb}$) <wherein $R^{1ab}$ represents a substituted lower alkyl group, a formyl group, a carboxyl group, a lower alkoxycarbonyl group (wherein a lower alkyl moiety of said lower alkoxycarbonyl group may be substituted with a 5- or 6-membered aromatic or aliphatic heterocyclic group), —CH═N—$OR^{7b}$ (wherein $R^{7b}$ represents a hydrogen atom or a lower alkyl group), a lower alkenyloxycarbonyl group, —CH═N—NH—$CONH_2$, a cyano group, —$COR^{8b}$ {wherein $R^{8b}$ represents an arylalkyloxy group (wherein the aryl group may contain one or more heteroatoms as ring-constituting atoms), or —N($R^{9b}$)($R^{10b}$) (wherein $R^{9b}$ and $R^{10b}$ are combined together with the adjacent nitrogen atom to form a nitrogen-containing 5- or 6-membered aromatic or aliphatic heterocyclic group)}, a vinyl group substituted with a lower alkenyloxycarbonyl group, —CO—S—$CH^2$—$CH_2$—NH—CO—$R^{Yb}$ (wherein $R^{Yb}$ represents a lower alkyl group), —CH═CH—COOH, or a substituted or unsubstituted aryl group, and $R^{1bb}$ represents a hydrogen atom, provided that when $R^{1ab}$ represents a carboxyl group or a lower alkoxycarbonyl group (wherein a lower alkyl moiety of said lower alkoxycarbonyl group may be substituted with a 5- or 6-membered aromatic or aliphatic heterocyclic group), $R^{1bb}$ may further represents a lower alkoxycarbonyl group (wherein a lower alkyl moiety of said lower alkoxycarbonyl group may be substituted with a 5- or 6-membered aromatic or aliphatic heterocyclic group), a carboxyl group, a cyano group, or an aryl group>, and when

----- between $R^2$ and the carbon atom at 5-position represents a single bond, $R^2$ represents a hydroxyl group, a lower alkoxyl group, or a lower alkenyloxycarbonyloxy group, and when

----- between $R^2$ and the carbon atom at 5-position represents a double bond, $R^2$ is combined together with the carbon atom at 5-position to form a carbonyl group or a hydroxinre group (—C(=NOH)—).

2. The compound or the salt according to claim 1, wherein

—X≡Y— is —CH=CH—.

3. The compound or the salt according to claim 1, wherein

—X≡Y— is —CH$_2$—CH$_2$—.

4. The compound or the salt according to claim 1, wherein $R^{11}$ is a substituted or unsubstituted lower alkyl group, a formyl group, a lower alkoxycarbonyl group, a lower alkenylcarbonyl group, a cyano group, or —COR$^4$.

5. The compound or the salt according to claim 1, wherein $R^1$ is a hydroxyl group or —OCH$_2$R$^{1ac}$ {wherein R$^{1ac}$ represents a substituted lower alkyl group, a carboxyl group, or a lower alkoxycarbonyl group (wherein a lower alkyl moiety of said lower alkoxycarbonyl group may be substituted with a 5- or 6-membered aromatic or aliphatic heterocyclic group)}.

6. The compound or the salt according to claim 1, wherein $R^2$ is a hydroxyl group or a lower alkenyloxycarbonyloxy group.

7. A medicament which comprises the compound according to claim 1 or a physiologically acceptable salt thereof as an active ingredient and a pharmaceutically acceptable additive.

8. A method for therapeutic treatment of parasitosis which comprises the step of administering to a mammal in need thereof a therapeutically effective amount of the compound according to claim 1 or a physiologically acceptable salt thereof.

9. A medicament for therapeutic treatment of parasitosis which comprises the compound according to claim 1 or a physiologically acceptable salt thereof as an active ingredient.

10. A method for therapeutic treatment of parasitosis which comprises the step of administering to a human in need thereof a therapeutically effective amount of the compound according to claim 1 or a physiologically acceptable salt thereof.

11. A method for the manufacture of the medicament of claim 7 comprising mixing the compound or a pharmaceutically acceptable salt thereof with the pharmaceutically acceptable additive.

\* \* \* \* \*

UNITED STATES PATENT AND TRADEMARK OFFICE
CERTIFICATE OF CORRECTION

PATENT NO.       : 7,250,402 B2
APPLICATION NO.  : 10/997869
DATED            : July 31, 2007
INVENTOR(S)      : Satoshi Omura et al.

It is certified that error appears in the above-identified patent and that said Letters Patent is hereby corrected as shown below:

On the Title Page, Item (75)

"Toshiaki Sunazuka, Funabashi (JP)" should read -- Toshiaki Sunazuka, Chiba (JP) --.

On the Title Page, Item (56)
"Shin et al., "Cleavage of the Spiroketal Portion of Avermectin $B_{2p}$"" should read --
Shin et al., "Cleavage of the Spiroketal Portion of Avermectin $B_{2a}$" --.

in column 65 line 11, "$-CO-S-CH^2-CH_2-NH-CO-R^X$" should read
-- $-CO-S-CH_2-CH_2-NH-CO-R^X$ --, in column 66 line 56, "heterocylie group" should read -- heterocyclic group --, in column 67 lines 33-34, "$-CO-S-CH^2-CH_2-NH-CO-R^{Ya}$" should read
-- $-CO-S-CH_2-CH_2-NH-CO-R^{Ya}$ --, in column 68 lines 62-63, "$-CO-S-CH^2-CH_2-NH-CO-R^{Yb}$" should read
-- $-CO-S-CH_2-CH_2-NH-CO-R^{Yb}$ --.

Signed and Sealed this

Eighth Day of July, 2008

JON W. DUDAS
*Director of the United States Patent and Trademark Office*